(12) United States Patent
Guckian et al.

(10) Patent No.: US 10,273,234 B2
(45) Date of Patent: Apr. 30, 2019

(54) COMPOUNDS THAT ARE S1P MODULATING AGENTS AND/OR ATX MODULATING AGENTS

(71) Applicant: BIOGEN MA INC., Cambridge, MA (US)

(72) Inventors: Kevin Guckian, Northborough, MA (US); Gnanasambandam Kumaravel, Lexington, MA (US); Bin Ma, Arlington, MA (US); Lihong Sun, Lexington, MA (US); Zhili Xin, Lexington, MA (US); Lei Zhang, Westford, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/420,020

(22) PCT Filed: Aug. 5, 2013

(86) PCT No.: PCT/US2013/053668
§ 371 (c)(1),
(2) Date: Feb. 6, 2015

(87) PCT Pub. No.: WO2014/025708
PCT Pub. Date: Feb. 13, 2014

(65) Prior Publication Data
US 2015/0203493 A1    Jul. 23, 2015

Related U.S. Application Data

(60) Provisional application No. 61/679,984, filed on Aug. 6, 2012.

(51) Int. Cl.
| C07D 471/08 | (2006.01) |
| A61K 31/122 | (2006.01) |
| C07C 229/48 | (2006.01) |
| C07D 223/06 | (2006.01) |
| C07D 205/04 | (2006.01) |
| C07D 207/16 | (2006.01) |
| C07D 209/52 | (2006.01) |
| C07D 211/62 | (2006.01) |
| A61K 45/06 | (2006.01) |
| A61K 31/397 | (2006.01) |
| A61K 31/403 | (2006.01) |
| A61K 31/44 | (2006.01) |
| A61K 31/55 | (2006.01) |
| A61K 31/196 | (2006.01) |
| A61K 31/40 | (2006.01) |
| A61K 31/439 | (2006.01) |
| A61K 31/445 | (2006.01) |
| C07C 211/38 | (2006.01) |
| C07D 207/08 | (2006.01) |

(52) U.S. Cl.
CPC .......... *C07D 471/08* (2013.01); *A61K 31/122* (2013.01); *A61K 31/196* (2013.01); *A61K 31/397* (2013.01); *A61K 31/40* (2013.01); *A61K 31/403* (2013.01); *A61K 31/439* (2013.01); *A61K 31/44* (2013.01); *A61K 31/445* (2013.01); *A61K 31/55* (2013.01);

*A61K 45/06* (2013.01); *C07C 211/38* (2013.01); *C07C 229/48* (2013.01); *C07D 205/04* (2013.01); *C07D 207/08* (2013.01); *C07D 207/16* (2013.01); *C07D 209/52* (2013.01); *C07D 211/62* (2013.01); *C07D 223/06* (2013.01); *C07B 2200/07* (2013.01); *C07C 2601/04* (2017.05); *C07C 2601/14* (2017.05)

(58) Field of Classification Search
CPC ... C07C 229/14; C07C 229/46; C07C 229/48; C07C 237/08; C07C 237/52; C07C 309/14; C07C 311/51; C07D 205/04; C07D 207/16; C07D 209/08; C07D 211/60; C07D 211/62; C07D 215/20; C07D 217/24; C07D 257/04; C07D 403/06; C07D 417/06
USPC ........ 514/114, 171, 210.17, 266.1, 312, 319, 514/423, 507, 538, 567, 700, 717; 544/283, 284; 546/157, 326; 548/531, 548/953; 560/39, 212; 562/444; 568/441, 634
See application file for complete search history.

(56) References Cited

U.S. PATENT DOCUMENTS

| 8,278,442 | B2* | 10/2012 | Bloxham | ............. | C07D 213/62 |
| | | | | | 544/131 |
| 8,802,659 | B2* | 8/2014 | Thomas | ............... | C07C 229/14 |
| | | | | | 514/114 |
| 9,186,367 | B2* | 11/2015 | Thomas | ............... | C07C 229/14 |
| 2003/0236270 | A1 | 12/2003 | Jacobsen et al. | | |
| 2010/0160258 | A1 | 6/2010 | Caldwell et al. | | |
| 2010/0240617 | A1 | 9/2010 | Lynch et al. | | |
| 2012/0190649 | A1* | 7/2012 | Thomas | ............... | C07C 229/14 |
| | | | | | 514/114 |
| 2015/0203515 | A1 | 1/2015 | Guckian et al. | | |
| 2015/0210647 | A1 | 7/2015 | Guckian et al. | | |
| 2015/0246063 | A1* | 9/2015 | Guckian | ................ | A61K 45/06 |
| | | | | | 514/119 |
| 2015/0361029 | A1 | 12/2015 | Guckian et al. | | |

FOREIGN PATENT DOCUMENTS

WO  WO-2007/092638 A1  8/2007
WO  WO-2008/064315 A1  5/2008
(Continued)

OTHER PUBLICATIONS

Exhibit I (2015).*
(Continued)

*Primary Examiner* — Heidi Reese
(74) *Attorney, Agent, or Firm* — McCarter & English, LLP; Steven G. Davis; Xin Zhang

(57) ABSTRACT

Compounds of formula (I) can modulate the activity of one or more S1P receptors and/or the activity of autotaxin (ATX).

14 Claims, No Drawings

(56) References Cited

FOREIGN PATENT DOCUMENTS

| WO | WO-2010/051031 A1 | 5/2010 |
| WO | WO-2011/017561 A1 | 2/2011 |
| WO | WO-2012/109108 A1 | 8/2012 |
| WO | WO-2014/025709 A1 | 2/2014 |

OTHER PUBLICATIONS

Choi et al. "Preparation of . . . " CA144:88080 (2005).*
Fulkerson et al. "Binding of Autotaxin . . . " J. Biol. Chem. vol. 286(40) 34654-34663 (2011).*
Gyermek et al. "Preparation of bis . . . , Fed. Reg. v.76(27) p;" CA130:325090 (1999).*
Improper Markush, Fed. Reg. vol. 76(27) 7165-7175, slide 1, 64-67 (2011).*
Jankowski et al. "Synthesis and propert . . . " CA86:89701 (1977).*
Sekiguchi et al. "Preparation of . . . " CA148:426746 (2008).*
Shibata et al. "Preparaion of cyanobenayl . . . " CA122:265379 (1995).*
Sharma et al.; "Synthesis and Bioactivity of Sphingosine Kinase Inhibitors and Their Novel Aspirinyl Conjugated Analogs"; European Journal of Medicinal Chemistry; 45:4149-4156 (2010).

* cited by examiner

COMPOUNDS THAT ARE S1P MODULATING AGENTS AND/OR ATX MODULATING AGENTS

CLAIM OF PRIORITY RELATED APPLICATIONS

This application is a 35 U.S.C. § 371 national stage filing of International Application No. PCT/US2013/053668, filed on Aug. 5, 2013, which claims priority to U.S. Provisional Application No. 61/679,984, filed on Aug. 6, 2012, the entire contents of which are incorporated herein by reference in their entirety.

TECHNICAL FIELD

This invention relates to compounds that are S1P modulating agents and/or ATX modulating agents, and methods of making and using such compounds.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulating agent, FTY720 (2-amino-2-[2-(4-octylphenyl)ethyl]propane 1,3-diol), that following phosphorylation, is an agonist at 4 of 5 S1P receptors, revealed that affecting S1P receptor activity influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds. S1P type 4 receptors ($S1P_4$) are expressed mainly in leukocytes, and specifically $S1P_4$ mediates immunosuppressive effects of S1P by inhibiting proliferation and secretion of effector cytokines, while enhancing secretion of the suppressive cytokine IL-10. See, for example, Wang, W. et. al., (2005) *FASEB J.* 19(12): 1731-3, which is incorporated by reference in its entirety. S1P type 5 receptors ($S1P_5$) are exclusively expressed in oligodendrocytes and oligodendrocyte precursor cells (OPCs) and are vital for cell migration. Stimulation of $S1P_5$ inhibits OPC migration, which normally migrate considerable distances during brain development. See, for example, Novgorodov, A. et al., (2007) *FASEB J,* 21: 1503-1514, which is incorporated by reference in its entirety.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing, tumor growth inhibition, and autoimmune diseases.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDGE and EDGE). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine-1-phosphate phosphohydrolases. Irreversible degradation of S1P is catalyzed by S1P lyase yielding ethanolamine phosphate and hexadecenal.

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxa13, NFAT-1 and v-jun), results in four alternatively spliced isoforms (α, β, γ, and δ). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Charaterization of a Novel Autotaxin Isoform, ATXδ," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activation of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/ phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 µM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA, the product of ATX action on LPC, is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. (See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in *Xenopus* oocytes and neurite retraction in PC12 pheochromocytoma cells. J Biol Chem 267, 21360-21367 (1992); each of which is incorporated by reference in its entirety.)

LPA is also found in other biofluids, such as saliva and follicular fluid, and has been implicated in a wide array of functions, such as wound heeling, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$ which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in $atx^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One particularly successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

SUMMARY

A compound of formula (I), or a pharmaceutically acceptable salt thereof, can be an S1P modulating agent and/or an ATX modulating agent, e.g., an S1P4 antagonist or ATX inhibitor.

In one aspect, a compound is represented by formula (I):

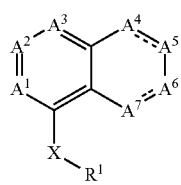

(I)

or a pharmaceutically acceptable salt thereof.

X can be O, S(O)$_r$, NR$^{12}$, C(O) or CH$_2$.

$A^1$, $A^2$, and $A^3$ can each independently be CR$^2$ or N.

$A^6$ and $A^7$ can each independently be CR$^2$, C(R$^2$)$_2$, N, or NR$^{19}$.

One of $A^4$ or $A^5$ can be CR$^2$, C(R$^2$)$_2$, N, or NR$^{19}$, and the other can be CR$^4$, provided that at least three of $A^1$, $A^2$, $A^3$, $A^4$, $A^5$, $A^6$ and $A^7$ can independently be CR$^2$ or C(R$^2$)$_2$.

"------" can indicate a double or a single bond.

R$^1$ can be a C$_{6-20}$alkyl, a C$_{3-14}$carbocyclyl, a 3- to 15-membered heterocyclyl, or a five- to 14-membered heteroaryl, wherein the heterocyclyl and the heteroaryl comprising from 1 to 10 heteroatoms independently selected from N, S or O, and wherein R$^1$ may be optionally substituted with from one to six independently selected R$^6$.

R$^2$, for each occurrence, can be independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido.

R$^4$ can be a group represented by the following formula:

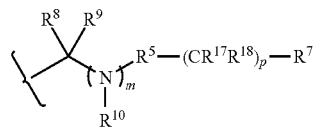

"{" can represent the point of attachment.

R$^5$ can be a C$_{1-6}$alkylene, C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members; or a bicyclic ring system represented by the following formula:

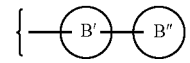

where B' and B" can be independently selected from the group consisting of monocyclic C$_{3-8}$carbocyclyl, a monocyclic 3- to 8-membered heterocyclyl, phenyl or a 5- to 6-membered heteroaryl; where R$^5$ may be optionally substituted with from 1 to 4 independently selected R$^{11}$.

R$^6$, for each occurrence, can be independently selected from the group consisting of halo, C$_{1-6}$alkyl, C$_{1-6}$alkoxy, C$_{1-6}$haloalkyl, C$_{3-8}$cycloalkyl, C$_{6-10}$aryl, C$_{1-6}$alkoxy-C$_{1-6}$alkyl, and tri-(C$_{1-6}$alkyl)silyl; or two R$^6$ that are attached to the same carbon atom may form C$_{3-8}$spirocycloalkyl or 3- to 8-membered spiroheterocycloalkyl.

R$^7$ can be —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

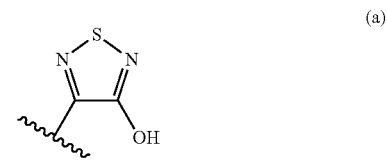

(a)

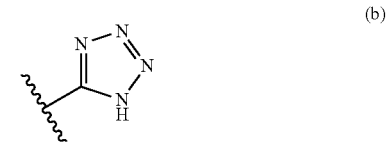

(b)

(c)

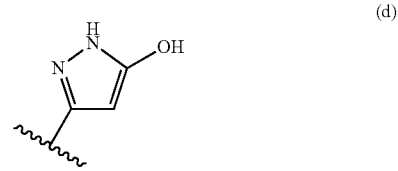

(d)

-continued
(e)
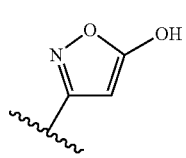
(f)
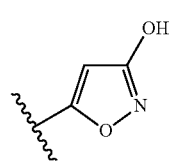
(g)
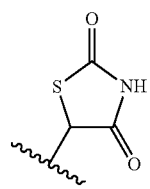
(h)
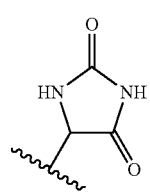
(i)
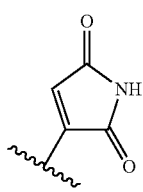
(j)
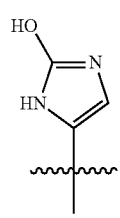
(k)
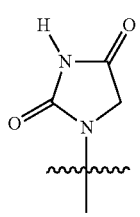
(l)
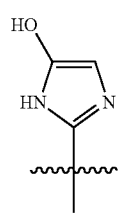
-continued
(m)
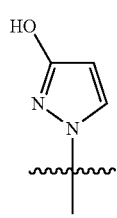
(n)
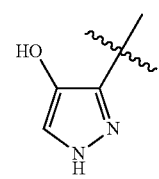
(o)
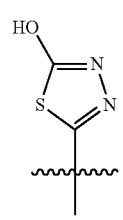
(p)
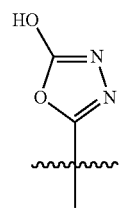
(q)
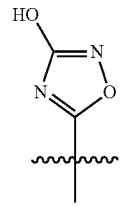
(r)
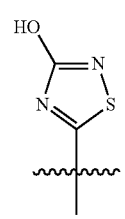
(s)
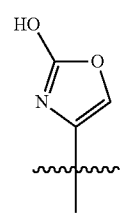

-continued
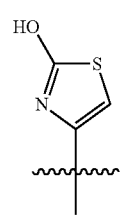 (t)
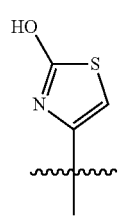 (u)
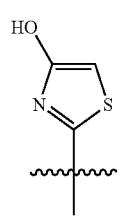 (v)
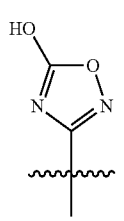 (w)
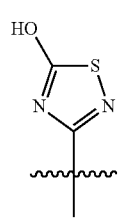 (x)
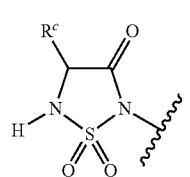 (y)
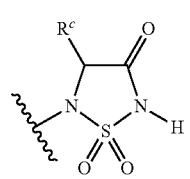 (z)
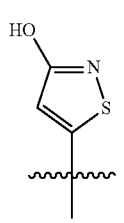 (a')
-continued
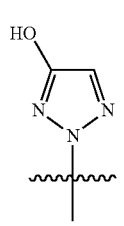 (b')
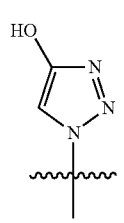 (c')
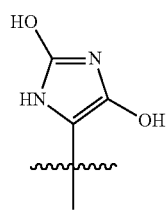 (d')
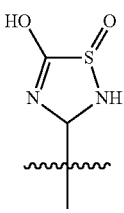 (e')
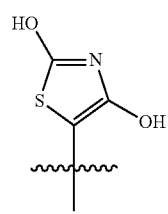 (f')
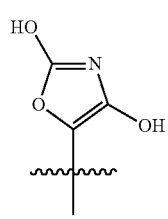 (g')
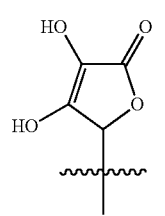 (h')
and

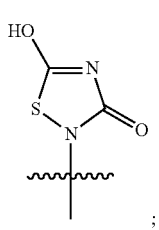

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each, independently, be hydrogen or a $C_{1-6}$alkyl.

$R^{11}$, for each occurrence, can independently be halo, hydroxyl, nitro, cyano, $C_{1-6}$alkyl, $C_{1-6}$haloalkyl, $C_{1-6}$alkoxy, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$.

$R^{15}$ for each occurrence can be independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; where the heteroaryl or heterocyclyl can comprise from 1 to 10 heteroatoms independently selected from O, N, or S; and where $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached form a 5 to 14 membered heteroaryl or a 3 to 15 membered heterocyclyl, where the heteroaryl or heterocyclyl can comprise from 1 to 10 heteroatoms independently selected from O, N, or S; and where the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can each independently be hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can independently be hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen of a $C_{1-4}$alkyl.

m can be 0 or 1, provided that when m is 0, $R^5$ can comprise at least one nitrogen.

p can be 0 or an integer from 1 to 6.

r, for each occurrence, can independently be 0, 1, or 2.

In some embodiments, $R^5$ can be substituted by —(CR$^{17}$R$^{18}$)$_p$—R$^7$ and can be optionally substituted by from 1 to 3 independently selected $R^{11}$.

In some embodiments, the compound can be represented by structural formula (II):

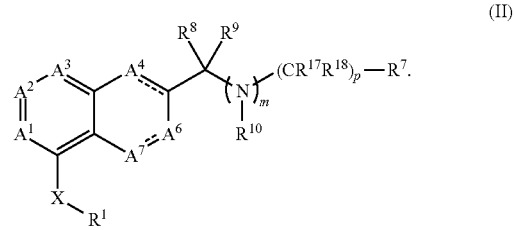

In some embodiments, the compound can be represented by structural formula (III):

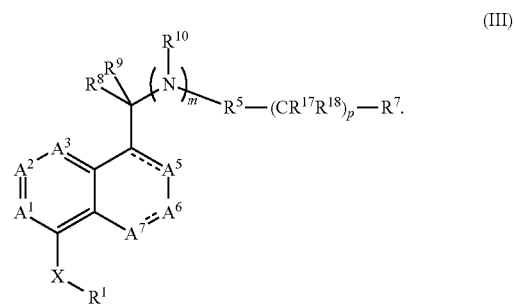

In some embodiments, $R^1$ can be a cyclohexyl which is optionally substituted with from one to three independently selected $R^6$.

In some embodiments, m can be 0; and $R^5$ can be selected from the group consisting of:

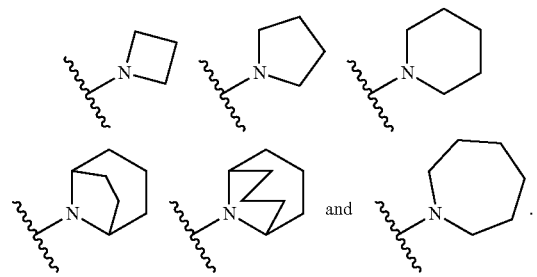

In some embodiments, m can be 1; and $R^5$ can be cyclobutyl, cyclopentyl or cyclohexyl each of which may be optionally substituted with from 1 to 3 independently selected $R^{11}$.

In some embodiments, $R^7$ can be COOH.

In some embodiments, $A^1$, $A^2$, and $A^3$ can each independently be CR$^2$.

In some embodiments, $A^4$ can be CR$^4$, $A^5$ can be CR$^2$, and $A^7$ can be CR$^2$; or $A^5$ can be CR$^4$, and $A^7$ can be CR$^2$.

In some embodiments, $A^1$, $A^2$, $A^3$, $A^6$, and $A^7$ can each independently be $CR^2$, and one of $A^4$ or $A^5$ can be $CR^2$ and the other can be $CR^4$.

In some embodiments, X can be O.

In another aspect, a compound can be selected from the group consisting of:
8-((5-((trans-4-(tert-butyl)cyclohexyl)oxy)naphthalen-2-yl)methyl)-8-azabicyclo[3.2.1]octane-3-carboxylic acid;
9-((5-((trans-4-(tert-butyl)cyclohexyl)oxy)naphthalen-2-yl)methyl)-9-azabicyclo[3.3.1]nonane-3-carboxylic acid;
3-(((5-((trans-4-(tert-butyl)cyclohexyl)oxy)naphthalen-2-yl)methyl)amino)-2,2-dimethylcyclobutanecarboxylic acid;
1-((5-((trans-4-(tert-butyl)cyclohexyl)oxy)naphthalen-2-yl)methyl)azetidine-3-carboxylic acid;
2-((5-((trans-4-(tert-butyl)cyclohexyl)oxy)naphthalen-2-yl)methyl)octahydrocyclopenta[c]pyrrole-5-carboxylic acid;
1-((5-((trans-4-(tert-butyl)cyclohexyl)oxy)naphthalen-2-yl)methyl)pyrrolidine-3-carboxylic acid;
3-(((5-((trans-4-(tert-butyl)cyclohexyl)oxy)naphthalen-2-yl)methyl)amino)cyclobutanecarboxylic acid;
1-((5-((trans-4-(tert-butyl)cyclohexyl)oxy)naphthalen-2-yl)methyl)azepane-4-carboxylic acid;
1-((5-((trans-4-(trifluoromethyl)cyclohexyl)oxy)naphthalen-2-yl)methyl)piperidine-4-carboxylic acid;
1-((5-((cis-4-(trifluoromethyl)cyclohexyl)oxy)naphthalen-2-yl)methyl)piperidine-4-carboxylic acid;
1-((5-((cis-4-isopropylcyclohexyl)oxy)naphthalen-2-yl)methyl)piperidine-4-carboxylic acid;
1-((5-((cis-4-ethylcyclohexyl)oxy)naphthalen-2-yl)methyl)piperidine-4-carboxylic acid;
1-((5-((trans-4-isopropylcyclohexyl)oxy)naphthalen-2-yl)methyl)piperidine-4-carboxylic acid;
1-((5-((trans-4-ethylcyclohexyl)oxy)naphthalen-2-yl)methyl)piperidine-4-carboxylic acid;
1-((5-((trans-4-methylcyclohexyl)oxy)naphthalen-2-yl)methyl)piperidine-4-carboxylic acid;
1-((5-((4,4-dimethylcyclohexyl)oxy)naphthalen-2-yl)methyl)piperidine-4-carboxylic acid;
1-((5-((trans-4-methylcyclohexyl)oxy)naphthalen-2-yl)methyl)azetidine-3-carboxylic acid;
1-((5-((trans-4-phenylcyclohexyl)oxy)naphthalen-2-yl)methyl)azetidine-3-carboxylic acid;
1-((5-((trans-4-ethylcyclohexyl)oxy)naphthalen-2-yl)methyl)azetidine-3-carboxylic acid;
1-((5-((trans-4-(trifluoromethyl)cyclohexyl)oxy)naphthalen-2-yl)methyl)azetidine-3-carboxylic acid;
1-((5-((trans-4-isopropylcyclohexyl)oxy)naphthalen-2-yl)methyl)azetidine-3-carboxylic acid;
1-((5-((trans-4-butylcyclohexyl)oxy)naphthalen-2-yl)methyl)azetidine-3-carboxylic acid;
1-((5-((trans-4-cyclopentylcyclohexyl)oxy)naphthalen-2-yl)methyl)azetidine-3-carboxylic acid;
1-((5-((trans-4-(tert-butyl)cyclohexyl)oxy)naphthalen-2-yl)methyl)piperidine-4-carboxylic acid;
1-((5-(heptyloxy)naphthalen-2-yl)methyl)piperidine-4-carboxylic acid;
9-((5-((cis-4-methylcyclohexyl)oxy)naphthalen-2-yl)methyl)-9-azabicyclo[3.3.1]nonane-3-carboxylic acid;
8-((5-((cis-4-methylcyclohexyl)oxy)naphthalen-2-yl)methyl)-8-azabicyclo[3.2.1]octane-3-carboxylic acid;
1-((5-((cis-4-methylcyclohexyl)oxy)naphthalen-2-yl)methyl)piperidine-4-carboxylic acid;
1-((5-(heptyloxy)naphthalen-1-yl)methyl)piperidine-4-carboxylic acid; and
1-((5-((trans-4-(tert-butyl)cyclohexyl)oxy)naphthalen-1-yl)methyl)piperidine-4-carboxylic acid;
or a pharmaceutically acceptable salt thereof.

In another aspect, a pharmaceutical composition includes a pharmaceutically acceptable carrier or excipient and a compound of formula (I), or a pharmaceutically acceptable salt thereof.

In another aspect, a method of preventing, treating, or reducing symptoms of a condition mediated by S1P activity or ATX activity in a mammal includes administering to said mammal an effective amount of a compound of formula (I), or a pharmaceutically acceptable salt thereof.

The condition can be selected from the group consisting of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, non-insulin dependent diabetes, a fibrosis of the lung, or a malignancy of the lung in a mammal.

In some embodiments, the condition can be multiple sclerosis.

In some embodiments, the condition can be rheumatoid arthritis.

The method can further include administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

In another aspect, a method of preventing, treating, or reducing chronic pain in a mammal includes administering to said mammal an effective amount of a compound of formula (I), or a pharmaceutically acceptable salt thereof.

The chronic pain can be inflammatory pain.

The chronic pain can be neuropathic pain.

Other features or advantages will be apparent from the following detailed description of several embodiments, and also from the appended claims.

DETAILED DESCRIPTION

The disclosed compounds can be S1P modulating agents and/or ATX modulating agents. In other words, the disclosed compounds can have activity as receptor agonists or receptor antagonists at one or more S1P receptors, or as an ATX modulating agent. In particular, the compounds can be S1P4 antagonists, or ATX inhibitors. A given compound can be an S1P modulating agent with little or substantially no ATX activity; or can be an ATX modulating agent with little or substantially no S1P activity; or, in some cases, can simultaneously be an S1P modulating agent and an ATX modulating agent. Preferably, a given compound is either an S1P modulating agent with little or substantially no ATX activity; or is an ATX modulating agent with little or substantially no S1P activity.

A compound, or a pharmaceutically acceptable salt thereof, can be represented by formula (I):

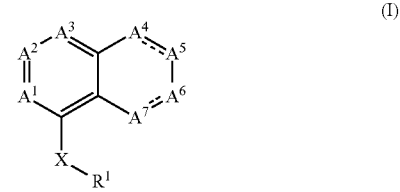

or a pharmaceutically acceptable salt thereof.

X can be O, S(O)$_r$, NR$^{12}$, C(O) or CH$_2$.

A$^1$, A$^2$, and A$^3$ can each independently be CR$^2$ or N.

A$^6$ and A$^7$ can each independently be CR$^2$, C(R$^2$)$_2$, N, or NR$^{19}$.

One of A$^4$ or A$^5$ can be CR$^2$, C(R$^2$)$_2$, N, or NR$^{19}$, and the other can be CR$^4$, provided that at least three of A$^1$, A$^2$, A$^3$, A$^4$, A$^5$, A$^6$ and A$^7$ can independently be CR$^2$ or C(R$^2$)$_2$.

"------" can indicate a double or a single bond.

R$^1$ can be a C$_{6-20}$alkyl, a C$_{3-14}$carbocyclyl, a 3- to 15-membered heterocyclyl, or a five- to 14-membered heteroaryl, wherein the heterocyclyl and the heteroaryl comprising from 1 to 10 heteroatoms independently selected from N, S or O, and wherein R$^1$ may be optionally substituted with from one to six independently selected R$^6$.

R$^2$, for each occurrence, can be independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido.

R$^4$ can be a group represented by the following formula:

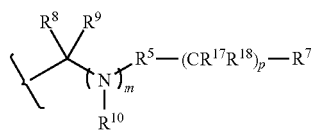

"{" can represent the point of attachment.

R$^5$ can be a C$_{1-6}$alkylene, C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members; or a bicyclic ring system represented by the following formula:

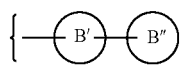

where B' and B" can be independently selected from the group consisting of monocyclic C$_{3-8}$carbocyclyl, a monocyclic 3- to 8-membered heterocyclyl, phenyl or a 5- to 6-membered heteroaryl; where R$^5$ may be optionally substituted with from 1 to 4 independently selected R$^{11}$.

R$^6$, for each occurrence, can be independently selected from the group consisting of halo, C$_{1-6}$alkyl, C$_{1-6}$alkoxy, C$_{1-6}$haloalkyl, C$_{3-8}$cycloalkyl, C$_{6-10}$aryl, C$_{1-6}$alkoxy-C$_{1-6}$alkyl, and tri-(C$_{1-6}$alkyl)silyl; or two R$^6$ that are attached to the same carbon atom may form C$_{3-8}$spirocycloalkyl or 3- to 8-membered spiroheterocycloalkyl.

R$^7$ can be —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

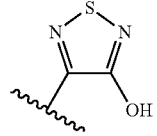 (a)

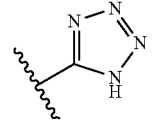 (b)

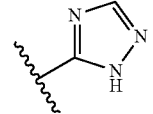 (c)

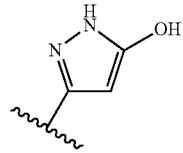 (d)

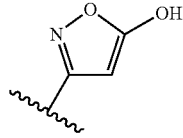 (e)

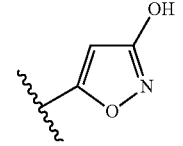 (f)

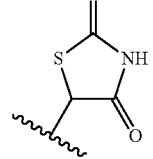 (g)

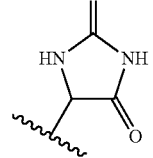 (h)

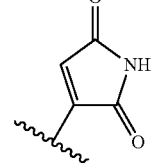 (i)

-continued
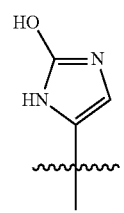 (j)
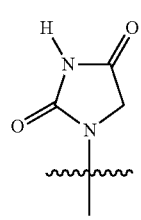 (k)
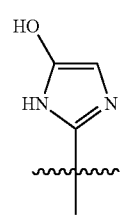 (l)
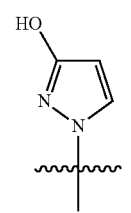 (m)
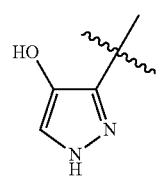 (n)
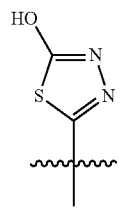 (o)
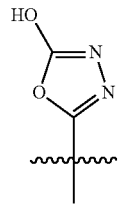 (p)
-continued
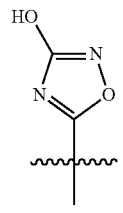 (q)
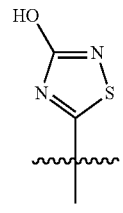 (r)
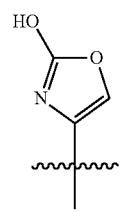 (s)
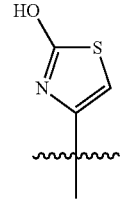 (t)
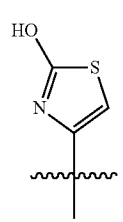 (u)
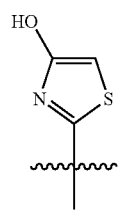 (v)
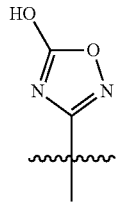 (w)

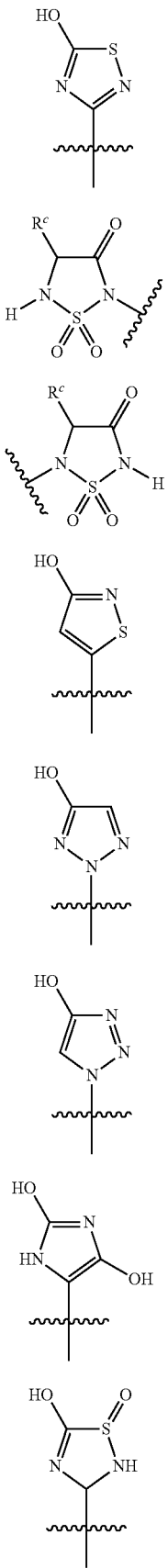

(x)
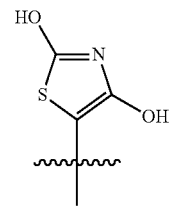

(y)
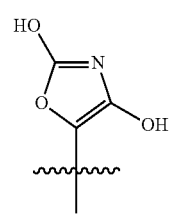

(z)
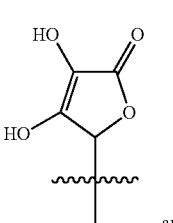

(a')

(b')

(c')

(d')

(e')
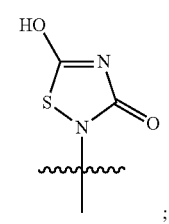

(f')

(g')

(h')

and (i')

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each, independently, be hydrogen or a $C_{1-6}$alkyl.

$R^{11}$, for each occurrence, can independently be halo, hydroxyl, nitro, cyano, $C_{1-6}$alkyl, $C_{1-6}$haloalkyl, $C_{1-6}$alkoxy, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —C(O)$NR^aR^b$, —N($R^a$)C(O)$R^b$, —C(O)$R^a$, —S(O)$_rR^a$, or —N($R^a$)S(O)$_2R^b$.

$R^{15}$ for each occurrence can be independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; where the heteroaryl or heterocyclyl can comprise from 1 to 10 heteroatoms independently selected from O, N, or S; and where $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)sulfamoyl.

R¹⁶ can be R¹⁵; or two R¹⁶ together with the nitrogen atom to which they are attached form a 5 to 14 membered heteroaryl or a 3 to 15 membered heterocyclyl, where the heteroaryl or heterocyclyl can comprise from 1 to 10 heteroatoms independently selected from O, N, or S; and where the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can each independently be hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can independently be hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ can comprise at least one nitrogen.

p can be 0 or an integer from 1 to 6.

r, for each occurrence, can independently be 0, 1, or 2.

In some embodiments, $R^5$ can be substituted by —$(CR^{17}R^{18})_p$—$R^7$ and can be optionally substituted by from 1 to 3 independently selected $R^{11}$.

In some embodiments, the compound can be represented by structural formula (II):

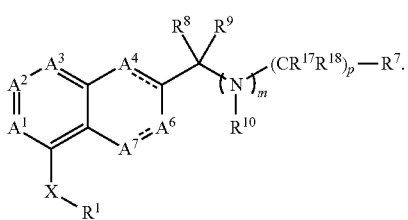

(II)

In some embodiments, the compound can be represented by structural formula (III):

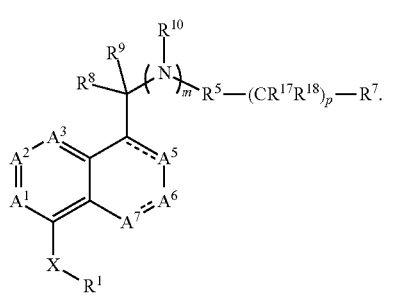

(III)

In some embodiments, $R^1$ can be a cyclohexyl which is optionally substituted with from one to three independently selected $R^6$.

In some embodiments, m can be 0; and $R^5$ can be selected from the group consisting of:

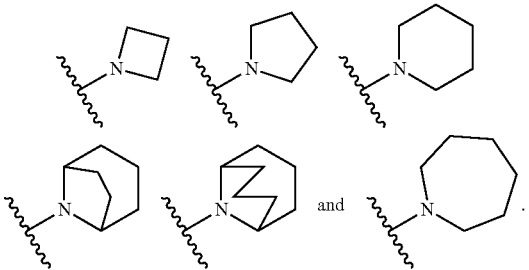

In some embodiments, m can be 1; and $R^5$ can be cyclobutyl, cyclopentyl or cyclohexyl each of which may be optionally substituted with from 1 to 3 independently selected $R^{11}$.

In some embodiments, $R^7$ can be COOH.

In some embodiments, $A^1$, $A^2$, and $A^3$ can each independently be $CR^2$.

In some embodiments, $A^4$ can be $CR^4$, $A^5$ can be $CR^2$, and $A^7$ can be $CR^2$; or $A^5$ can be $CR^4$, and $A^7$ can be $CR^2$.

In some embodiments, $A^1$, $A^2$, $A^3$, $A^6$, and $A^7$ can each independently be $CR^2$, and one of $A^4$ or $A^5$ can be $CR^2$ and the other can be $CR^4$.

In some embodiments, X can be O.

A compound can be selected from the group consisting of:
8-((5-((trans-4-(tert-butyl)cyclohexyl)oxy)naphthalen-2-yl)methyl)-8-azabicyclo[3.2.1]octane-3-carboxylic acid;
9-((5-((trans-4-(tert-butyl)cyclohexyl)oxy)naphthalen-2-yl)methyl)-9-azabicyclo[3.3.1]nonane-3-carboxylic acid;
3-(((5-((trans-4-(tert-butyl)cyclohexyl)oxy)naphthalen-2-yl)methyl)amino)-2,2-dimethylcyclobutanecarboxylic acid;
1-((5-((trans-4-(tert-butyl)cyclohexyl)oxy)naphthalen-2-yl)methyl)azetidine-3-carboxylic acid;
2-((5-((trans-4-(tert-butyl)cyclohexyl)oxy)naphthalen-2-yl)methyl)octahydrocyclopenta[c]pyrrole-5-carboxylic acid;
1-((5-((trans-4-(tert-butyl)cyclohexyl)oxy)naphthalen-2-yl)methyl)pyrrolidine-3-carboxylic acid;
3-(((5-((trans-4-(tert-butyl)cyclohexyl)oxy)naphthalen-2-yl)methyl)amino)cyclobutanecarboxylic acid;
1-((5-((trans-4-(tert-butyl)cyclohexyl)oxy)naphthalen-2-yl)methyl)azepane-4-carboxylic acid;
1-((5-((trans-4-(trifluoromethyl)cyclohexyl)oxy)naphthalen-2-yl)methyl)piperidine-4-carboxylic acid;
1-((5-((cis-4-(trifluoromethyl)cyclohexyl)oxy)naphthalen-2-yl)methyl)piperidine-4-carboxylic acid;
1-((5-((cis-4-isopropylcyclohexyl)oxy)naphthalen-2-yl)methyl)piperidine-4-carboxylic acid;
1-((5-((cis-4-ethylcyclohexyl)oxy)naphthalen-2-yl)methyl)piperidine-4-carboxylic acid;
1-((5-((trans-4-isopropylcyclohexyl)oxy)naphthalen-2-yl)methyl)piperidine-4-carboxylic acid;
1-((5-((trans-4-ethylcyclohexyl)oxy)naphthalen-2-yl)methyl)piperidine-4-carboxylic acid;
1-((5-((trans-4-methylcyclohexyl)oxy)naphthalen-2-yl)methyl)piperidine-4-carboxylic acid;
1-((5-((4,4-dimethylcyclohexyl)oxy)naphthalen-2-yl)methyl)piperidine-4-carboxylic acid;
1-((5-((trans-4-methylcyclohexyl)oxy)naphthalen-2-yl)methyl)azetidine-3-carboxylic acid;
1-((5-((trans-4-phenylcyclohexyl)oxy)naphthalen-2-yl)methyl)azetidine-3-carboxylic acid;

1-((5-((trans-4-ethylcyclohexyl)oxy)naphthalen-2-yl)
methyl)azetidine-3-carboxylic acid;
1-((5-((trans-4-(trifluoromethyl)cyclohexyl)oxy)naphthalen-2-yl)methyl)azetidine-3-carboxylic acid;
1-((5-((trans-4-isopropylcyclohexyl)oxy)naphthalen-2-yl)
methyl)azetidine-3-carboxylic acid;
1-((5-((trans-4-butylcyclohexyl)oxy)naphthalen-2-yl)
methyl)azetidine-3-carboxylic acid;
1-((5-((trans-4-cyclopentylcyclohexyl)oxy)naphthalen-2-yl)
methyl)azetidine-3-carboxylic acid;
1-((5-((trans-4-(tert-butyl)cyclohexyl)oxy)naphthalen-2-yl)
methyl)piperidine-4-carboxylic acid;
1-((5-(heptyloxy)naphthalen-2-yl)methyl)piperidine-4-carboxylic acid;
9-((5-((cis-4-methylcyclohexyl)oxy)naphthalen-2-yl)
methyl)-9-azabicyclo[3.3.1]nonane-3-carboxylic acid;
8-((5-((cis-4-methylcyclohexyl)oxy)naphthalen-2-yl)
methyl)-8-azabicyclo[3.2.1]octane-3-carboxylic acid;
1-((5-((cis-4-methylcyclohexyl)oxy)naphthalen-2-yl)
methyl)piperidine-4-carboxylic acid;
1-((5-(heptyloxy)naphthalen-1-yl)methyl)piperidine-4-carboxylic acid; and
1-((5-((trans-4-(tert-butyl)cyclohexyl)oxy)naphthalen-1-yl)
methyl)piperidine-4-carboxylic acid;
or a pharmaceutically acceptable salt thereof.

The term "fused ring system," as used herein, is a ring system that has two or three rings (preferably two rings) independently selected from carbocyclyl, heterocyclyl, aryl or heteroaryl rings that share one side. A fused ring system may have from 4-15 ring members, preferably from 5-10 ring members. Examples of fused ring systems include octahydroisoquinolin-2(1H)-yl, 2,3-dihydro-1H-indenyl, octahydro-1H-pyrido[1,2-a]pyrazinyl, and decahydroisoquinolinyl).

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system can have more than one bridge within the ring system (e.g., adamantyl). A bridged ring system may have from 6-10 ring members, preferably from 7-10 ring members. Examples of bridged ring systems include adamantyl, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R, 5S)-bicyclo[3.2.1]octanyl, 3-azabicyclo[3.3.1]nonanyl, and bicyclo[2.2.1]heptanyl. More preferably, the bridged ring system is selected from the group consisting of 9-azabicyclo [3.3.1]nonan-9-yl, 8-azabicyclo[3.2.1]octanyl, and bicyclo [2.2.2]octanyl.

The term "spiro ring system," as used herein, is a ring system that has two rings each of which are independently selected from a carbocyclyl or a heterocyclyl, wherein the two ring structures having one atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl and 2,8-diazaspiro[4.5]decanyl.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6 carbon atoms, more preferably about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. Preferably, haloalkoxy groups have about 1-6 carbon atoms, more preferably about 1-4 carbon atoms.

As used herein, the term "alkylthio" refers to alkyl-S—, wherein alkyl is defined herein above.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

The term "spirocycloalkyl" as used herein, is a cycloalkyl that has one ring atom in common with the group to which it is attached. Spirocycloalkyl groups may have from 3 to 14 ring members. In a preferred embodiment, the spirocycloalkyl has from 3 to 8 ring carbon atoms and is monocyclic.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

The term "alkanoyl" refers to alkyl-C(O)— wherein the alkyl is defined as above.

The term "alkoxycarbonyl" refers to alkoxy-C(O)—, wherein the alkoxy group is defined as above.

The term "alkanoyloxy" refers to alkyl-C(O)O—, wherein the alkyl is defined as above.

A carbamoyl is a group having the formula $NH_2C(O)$—. The term N-alkylcarbamoyl is a carbamoyl group in which one of the hydrogen atoms is replaced with an alkyl group. The term N,N-dialkylcarbamoyl is a carbamoyl group in which each hydrogen atoms is replaced with an alkyl group which may be the same or different.

The term "alkylamido" refers to a group having the formula alkyl-C(O)—NH—. As used herein, the term "alkylsulfonyl" refers to a group having the formula alkyl-$SO_2$—.

A sulfamoyl is a group having the formula $NH_2S(O)_2$—. The term N-alkylsulfamoyl is a sulfamoyl group in which one of the hydrogen atoms is replaced with an alkyl group. The term N,N-dialkylsulfamoyl is a sulfamoyl group in which each hydrogen atoms is replaced with an alkyl group which may be the same or different.

The term "alkylsulfonamido" refers to a group having the formula alkyl-$S(O)_2$—NH—.

The term "trialkylsilyl" refers to $(alkyl)_3$-Si—, wherein each of the alkyl groups may be the same or different.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$aryl is an aryl group which has from 6 to 10 carbon atoms; $C_{1-4}$haloalkyl is a haloalkyl group which has from 1 to 4 carbon atoms; and N,N-di-$C_{1-6}$ alkylamino is a N,N-dialkylamino group in which the nitrogen is substituted with two alkyl groups each of which is independently from 1 to 6 carbon atoms.

The phrase "compound of the invention," as used herein, refers to compounds represented by formulae (I), (II), and (III), and any of the specific examples disclosed herein.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

By way of clarity, compounds of the invention included all isotopes of the atoms present in formulae (I), (II), and (III), and any of the examples or embodiments disclosed herein. For example, H (or hydrogen) represents any isotopic form of hydrogen including $^1H$, $^2H$ (D), and $^3H$ (T); C represents any isotopic form of carbon including and $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formulae (I), (II), and (III), and any of the examples or embodiments disclosed herein comprises isotopes of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formula (I), when, for example, hydrogen is enriched in the deuterium isotope, the symbol "D" may be used to represent the enrichment in deuterium. In one embodiment, when a compound of the invention is enriched in a radioactive isotope, for example $^3H$ and $^{14}C$, they may be useful in drug and/or substrate tissue distribution assays. It is to be understood that the invention encompasses all such isotopic forms which modulate ATX activity.

Compounds of the invention can modulate the activity of S1P receptors. A compound of the invention can have S1P receptor agonist or antagonist activity. The compound can be selective for the S1P4 receptor. The compound can be a selective S1P4 antagonist. Being selective can mean that the compound binds to the receptor (or relatively small group of related molecules or proteins) in a complex mixture, or in other words, when exposed to a variety of closely related receptor types, the compound can bind preferentially to just one of the receptor types.

The compound can have a greater affinity for the S1P4 receptor, by at by at least 100-fold, by at least 50-fold, by at least 10-fold, by at least 5-fold or by at least 2-fold, than for S1P1 receptor, S1P2 receptor, S1P3 receptor, or S1P5 receptor.

An inhibitor of S1P4 mediated activity can block S1P interaction with an S1P4 receptor. For example, the inhibitor can be an antagonist of an S1P4 receptor. An antagonist can be a molecule that has affinity for the receptor but does not induce activity or a specific activity from the receptor. The antagonist can bind with an S1P4 receptor with an $IC_{50}$ value of less than 1 µM, less than 750 nM, less than 500 nM, less than 250 nM or less than 100 nM. The antagonist can bind with an S1P4 receptor with an $IC_{50}$ value in a range between 1 nM and 1 µM, between 1 nM and 500 nM, between 10 nM and 250 nM, between 25 nm and 100 nM, or between 50 nM and 100 nM.

The compounds can also promote oligodendrocyte progenitor cell differentiation. The compounds can promote myelination or remyelination.

An "S1P modulating agent" refers a compound or composition that is capable of inducing a detectable change in S1P receptor activity in vivo or in vitro (e.g., at least 10% increase or decrease in S1P activity as measured by a given assay such as the assays described in the examples and known in the art. "S1P receptor," refers to all of the S1P receptor subtypes (for example, the S1P receptors S1P1, S1P2, S1P3, S1P4, or S1P5), unless the specific subtype is indicated. It is well known in the art how to determine S1P agonist or antagonist activity using the standard tests described herein, or using other similar tests which are well known in the art. In some cases, depending on the cell type and conditions used, an S1P modulating agent can have agonist or antagonist activity, even at the same receptor subtype.

The biological effects of an S1P modulating agent vary depending on whether the compound has S1P receptor agonist or antagonist activity. Potential uses of an S1P modulating agent include, but are not limited to, prevention or treatment of a pathological condition or symptom in a mammal. For example, the condition can include asthma, an inflammatory neuropathies, arthritis, lupus erythematosis, psoriasis, an ischemia reperfusion injury, a solid tumor, a tumor metastasis, a disease associated with angiogenesis, a vascular disease, a pain condition, an acute viral disease, or insulin-dependent diabetes, and non-insulin dependent diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), multiple sclerosis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P receptor agonists are described in provisional U.S. Application No. 60/956,111, filed Aug. 15, 2007, and PCT/US2008/073378, filed Aug. 15, 2008, each of which is incorporated by reference in its entirety. See also provisional U.S. Application No. 61/231,539, filed Aug. 5, 2009, and PCT/US2010/44607, filed Aug. 5, 2010, each of which is incorporated by reference in its entirety. See also provisional U.S. Application No. 61/440,254, filed Feb. 7, 2011, and PCT/US2012/23799 filed Feb. 6, 2012, each of which is incorporated by reference in its entirety.

Additional potential uses of an S1P modulating agent include, but are not limited to, prevention or treatment of a pathological condition or symptom in a mammal. For example, the condition can include inhibited cell migration of oligodendrocyte precursor cells (OPCs).

Potential uses of an S1P receptor antagonist, and S1P4 receptor type selective antagonists particularly, include, but are not limited to, prevention or treatment of a pathological condition or symptom in a mammal.

LPA has been shown to be involved in lymphocyte trafficking and helps promote entry of lymphocytes into secondary lymphoid organs (see Kanda, et al., Nat. Immunology (2008), 9:415-423). Therefore, the disclosed compounds are expected to be useful for altering lymphocyte trafficking as a method for prolonging allograft survival, for example transplantation including solid organ transplants, treatment of graft vs. host disease, bone marrow transplantation, and the like.

An "ATX modulating agent" refers a compound or composition that is capable of inducing a detectable change in ATX activity in vivo or in vitro (e.g., at least 10% increase or decrease in ATX activity as measured by a given assay such as the assays described in the examples and known in the art. A compound of the invention be an ATX modulating agent, i.e., it can modulate the activity of ATX. For example, a compound of the invention can be an ATX inhibitor. The compound can be a selective ATX modulating agent. Being selective can mean that the compound binds to ATX preferentially when exposed to a variety of potential binding partners. The compound can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Potential uses of an ATX modulating agent include, but are not limited to, prevention or treatment of a pathological condition or symptom in a mammal. The pathological disorder can be an inflammatory disorder, an autoimmune disorder, a fibrosis of the lung, or a malignancy of the lung. Prevention or treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. In one embodiment, the inflammatory disorder is rheumatoid arthritis (RA). In another embodiment, the autoimmune disorder is multiple sclerosis (MS). A particular example of lung fibrosis is an interstitial lung disease, for instance, pulmonary fibrosis. See, for example, WO 2011/151461, which is incorporated by reference in its entirety.

In some embodiments, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes dorsalis due to untreated syphilis, demyelination due to exposure to an organophosphates, demyelination due to vitamin B12 deficiency or copper deficiency.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Neurological Disorders

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). CNS neurons can have the inherent potential to regenerate after injury, but they can be inhibited from doing so by inhibitory proteins present in myelin (Brittis et al., 2001, *Neuron* 30:11-14; Jones et al., 2002, J. *Neurosci.* 22:2792-2803; Grimpe et al., 2002, *J. Neurosci.:* 22:3144-3160, each of which is incorporated by reference in its entirety).

Several myelin inhibitory proteins found on oligodendrocytes have been characterized. Known examples of myelin inhibitory proteins can include NogoA (Chen et al., Nature, 2000, 403, 434-439; Grandpre et al., *Nature* 2000, 403, 439-444, each of which is incorporated by reference in its entirety), myelin associated glycoprotein (MAG) (McKerracher et al., 1994, *Neuron* 13:805-811; Mukhopadhyay et al., 1994, *Neuron* 13:757-767, each of which is incorporated by reference in its entirety) or oligodendrocyte glycoprotein (OM-gp), Mikol et al., 1988, *J. Cell. Biol.* 106:1273-1279, each of which is incorporated by reference in its entirety). Each of these proteins can be a ligand for the neuronal Nogo receptor-1 (NgR1 (Wang et al., *Nature* 2002, 417, 941-944; Grandpre et al., *Nature* 2000, 403, 439-444; Chen et al., *Nature,* 2000, 403, 434-439; Domeniconi et al., *Neuron* 2002, published online Jun. 28, 2002, each of which is incorporated by reference in its entirety).

Nogo receptor-1 (NgR1) is a GPI-anchored membrane protein that contains 8 leucine rich repeats (Fournier et al., 2001, *Nature* 409:341-346, which is incorporated by reference in its entirety). Upon interaction with inhibitory proteins (e.g., NogoA, MAG and OM-gp), the NgR1 complex can transduce signals that lead to growth cone collapse and inhibition of neurite outgrowth.

There is a need for molecules and methods for inhibiting NgR1-mediated growth cone collapse and the resulting inhibition of neurite outgrowth. Additionally, there is a need for molecules which increase neuronal survival and axon regeneration, particularly for the treatment of disease, disorders or injuries that involve axonal injury, neuronal or oligodendrocyte cell death, demyelination or dymyelination or generally relate to the nervous system.

Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

Various disease-modifying treatments may be available for MS, including the use of corticosteroids and immunomodulating agents such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346: 165-73 (2002), each of which is incorporated by reference in its entirety. However, there remains an urgent need to devise additional therapies for MS and other demyelination and dismyelination disorders.

A compound of the invention, or a pharmaceutically acceptable salt thereof, can promote myelination or remyelination. A method can include administering a compound of the invention, or a pharmaceutically acceptable salt thereof, to cells. A method of promoting oligodendrocyte progenitor cell differentiation can include administering a compound of the invention, or a pharmaceutically acceptable salt thereof, to cells. A method of treating multiple sclerosis can include administering a compound of the invention, or a pharmaceutically acceptable salt thereof, to a subject.

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomeningeal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was been detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety.

Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, ei al, Edg8/S1 P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and S1P5 are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA. As demyelination and deregulated cerebrospinal fluid homeostasis are the hallmarks of multiple sclerosis, a role of ATX and LPA signaling in the pathophysiology of multiple sclerosis seems very likely.

The S1P modulating agents and/or ATX modulating agents of the invention can be used to various forms of MS including relapsing-remitting, secondary-progressive, primary-progressive, and progressive-relapsing forms. In addition, S1P modulating agents and/or ATX modulating agents of the invention can be used alone or in conjunction with other agents to treat or prevent MS. In a preferred embodiment, the compounds of the invention can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, *Nature Chemical Biology* (January 2012), 8:22-23).

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient ($Lpar1^{-/-}$) mice (Nagai, et al., *Molecular Pain* (2010), 6:78).

Thus compounds of the invention are useful in treating or preventing chronic pain such as inflammatory pain and neuropathic pain in mammals.

Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well-established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment a method for treating an individual with RA or the individual at risk of suffering thereof comprises administering to said individual an S1P modulating agent and/or ATX modulating agent of the invention in conjunction with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Pulmonary Fibrosis

Evidence also suggests a role for ATX in pulmonary fibrosis. Mice lacking lysophosphatidic acid (LPA) receptor 1 (LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models.

Therefore, we hypothesized that genetic or pharmacologic inhibition of ATX activity would reduce local or circulating LPA levels and hence attenuate disease pathogenesis.

Lung Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers.

See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85. 1372-1382 (2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

In cases where a compound of the invention can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

Pharmaceutical compositions can include a compound of the invention, or a pharmaceutically acceptable salt thereof. More particularly, such compounds can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, is used to administer the appropriate compound to a subject.

The compounds of the invention, or a pharmaceutically acceptable salt thereof, are useful for treating a disease or disorder associated with S1P receptor mediated activity, and/or ATX activity. In one embodiment, a therapeutically effective amount of a compound of the invention, or a pharmaceutically acceptable salt thereof, is administered to a subject in need thereof. In another embodiment, a pharmaceutical composition comprising a therapeutically effective amount of a compound of the invention, or a pharmaceutically acceptable salt thereof, and a pharmaceutically-acceptable carrier is administered to a subject in need thereof.

The compounds of the invention can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxyl)ethyl-rapamycin etc.); corticosteroids; cyclophosphamide; azathioprine; mitoxanthrone, methotrexate; leflunomide; mizoribine;

mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulating agenty compounds, e.g. CTLA41g, or other adhesion molecule inhibitors, e.g. mAbs or low molecular weight inhibitors including Selectin antagonists and VLA-4 antagonists (such as Tysabri®); remyelinating agents such as BIIB033. Compounds of the invention can also be used in combination with agents which treat the symptoms of multiple sclerosis such as fampridine.

The dose of a compound of the invention, or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of the invention. Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds of the invention are expected to be useful in treating demyelination disorders.

Since LPA is a proinflammatory factor reducing the amount of LPA produced by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance.

A compound of the invention, or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes. In addition, the term "administer" or "administering" encompasses delivering a compound of the invention as a prodrug which is converted or metabolized in the body of the mammal into a compound of the invention. In one embodiment, a compound of the invention is administered in a non-prodrug form. In another embodiment, the compound is administered as a prodrug which is metabolized to a compound of the invention in the body of a mammal.

Thus, a compound of the invention, or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of the invention may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of a compound(s) of the invention in a liquid composition, such as a lotion, can be from about 0.1 to about 25 weight percent, preferably from about 0.5-10 weight percent. The concentration in a semisolid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 µM to about 75 µM, preferably, about 1 µM to 50 µM, or about 2 µM to about 30 µM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of the invention and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

Example 1: 8-((5-((trans-4-(tert-butyl)cyclohexyl)oxy)naphthalen-2-yl)methyl)-8-azabicyclo[3.2.1]octane-3-carboxylic acid Step 1: 5-((trans-4-(tert-butyl)cyclohexyl)oxy)naphthalen-2-amine

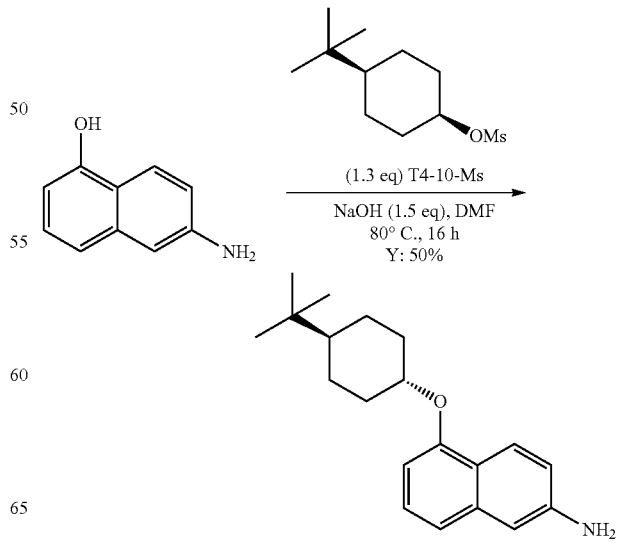

Into a solution of 6-aminonaphthalen-1-ol (1.59 g, 10 mmol, 1.0 eq) in DMF (20 mL) were added cis-4-(tert-butyl) cyclohexyl methanesulfonate (3.04 g, 13 mmol, 1.3 eq) and NaOH (0.60 g, 15 mmol, 1.5 eq). The mixture was stirred at 80° C. for 16 h. After cooling down to rt, the mixture was diluted with brine (50 mL) and extracted with EtOAc (60 mL×3). The combined organic phase was dried over Na$_2$SO$_4$ and concentrated under reduced pressure. The residue was purified by silica gel plate (EtOAc/petroleum ether=1:10) to give 5-((trans-4-(tert-butyl)cyclohexyl)oxy)naphthalen-2-amine as brown oil (1.48 g, Y: 50%).

$^1$H NMR (400 MHz, CDCl$_3$) δ: 8.08 (d, J=8.8 Hz, 1H), 7.23 (d, J=8.0 Hz, 1H), 7.15 (d, J=8.4 Hz, 1H), 6.95 (s, 1H), 6.90 (dd, J=2.0 Hz, 8.8 Hz, 1H), 6.63 (d, J=7.6 Hz, 1H), 4.32-4.23 (m, 1H), 3.00 (br, 2H), 2.31-2.78 (m, 2H), 2.16-2.11 (m, 2H), 1.89-1.84 (m, 2H), 1.65-1.11 (m, 3H), 0.89 (s, 9H); ESI-MS (M+H)$^+$: 298.1.

Step 2: 1-((trans-4-(tert-butyl)cyclohexyl)oxy)-6-iodonaphthalene

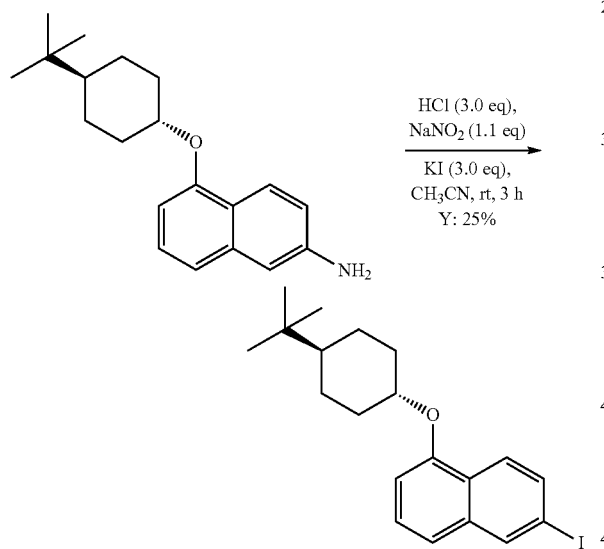

Into a solution of 5-((trans-4-(tert-butyl)cyclohexyl)oxy) naphthalen-2-amine (900 mg, 3.03 mmol, 1.0 eq) in acetonitrile (50 mL) was added 1N HCl (9 mL, 9 mmol, 3.0 eq) at 0° C. Then a solution of NaNO$_2$ (228 mg, 3.3 mmol, 1.1 eq) in 10 mL water was added. After stirring at 0° C. for 0.5 h, KI (1.5 g, 9.0 mmol, 3.0 eq) was added. The mixture was stirred at rt for another 3 h and diluted with brine (50 mL). The mixture was extracted with EtOAc (80 mL×2). The combined organic phase was dried over Na$_2$SO$_4$ and concentrated under reduced pressure. The residue was purified by column chromatography on silica gel (petroleum ether) to give 1-((trans-4-(tert-butyl)cyclohexyl)oxy)-6-iodonaphthalene as brown oil (310 mg, Y: 25%).

$^1$H NMR (400 MHz, CDCl$_3$) δ: 8.05 (s, 1H), 7.87 (d, J=9.2 Hz, 1H), 7.55 (dd, J=1.6 Hz, 8.8 Hz, 1H), 7.21 (d, J=8.0 Hz, 1H), 7.12 (d, J=8.0 Hz, 1H), 6.73 (d, J=8.0 Hz, 1H), 4.21-4.13 (m, 1H), 2.19-2.16 (m, 2H), 1.78-1.75 (m, 2H), 1.43-1.33 (m, 2H), 1.05-0.98 (m, 3H), 0.80 (s, 9H); ESI-MS (M+H)$^+$: 409.1.

Step 3: 5-((trans-4-(tert-butyl)cyclohexyl)oxy)-2-naphthaldehyde

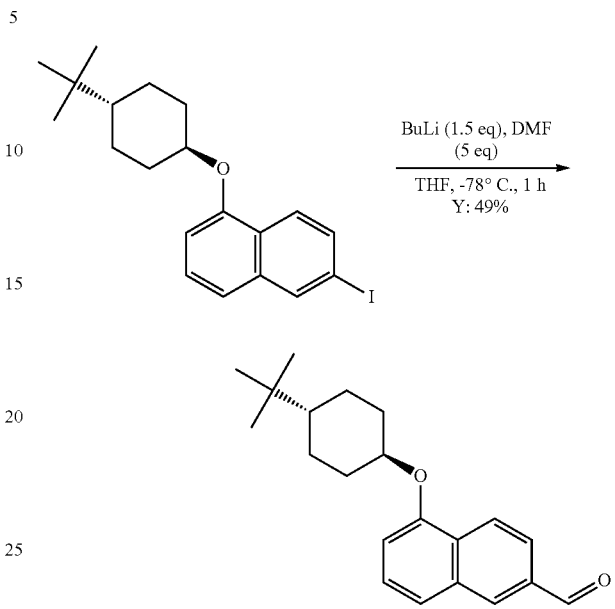

Into a solution of 1-((trans-4-(tert-butyl)cyclohexyl)oxy)-6-iodonaphthalene (200 mg, 0.49 mmol) in dry THF (5 mL) at −78° C. was added n-BuLi (0.38 mL, 2 M in hexane, 1.5 eq). After stirring for 5 min, dry DMF (180 mg, 2.5 mmol, 5.0 eq) was added via a syringe. The reaction was allowed to warm to −20° C. and stirred for 30 min. The reaction was quenched with sat. aq. NH$_4$Cl (10 mL) and extracted with EtOAc (10 mL×2). The combined organics were dried and concentrated. The residue was purified by column chromatography on silica gel (petroleum ether) to give compound 5-((trans-4-(tert-butyl)cyclohexyl)oxy)-2-naphthaldehyde (80 mg Y: 49%) as a white solid.

$^1$H NMR (400 MHz, CDCl$_3$) δ: 10.16 (s, 1H), 8.37 (d, J=8.8 Hz, 1H), 8.28 (s, J=1.6 Hz, 1H), 7.90 (dd, J=1.6 Hz, 8.8 Hz, 1H), 7.55 (d, J=8.0 Hz, 1H), 7.48-7.45 (m, 1H), 7.02 (d, J=7.6 Hz, 1H), 4.37-4.31 (m, 1H), 2.33-2.30 (m, 2H), 1.93-1.90 (m, 2H), 1.59-1.54 (m, 2H), 1.28-1.13 (m, 3H), 0.90 (s, 9H); ESI-MS (M+H)$^+$: 311.2.

Step 4: methyl 8-((5-((trans-4-(tert-butyl)cyclohexyl)oxy)naphthalen-2-yl)methyl)-8-azabicyclo[3.2.1]octane-3-carboxylate

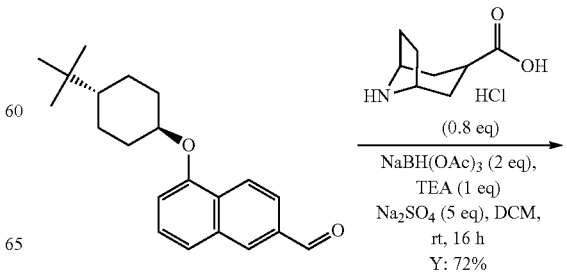

-continued

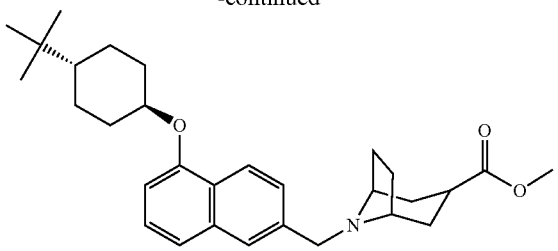

A mixture of 5-((trans-4-(tert-butyl)cyclohexyl)oxy)-2-naphthaldehyde (93 mg, 0.3 mmol), methyl 8-aza-bicyclo[3.2.1]octane-3-carboxylate hydrochloride (75 mg, 0.24 mmol, 0.8 eq), TEA (30 mg, 0.3 mmol, 1 eq), Na$_2$SO$_4$ (210 mg, 1.5 mmol, 5 eq) and NaBH(OAc)$_3$ (127 mg, 0.6 mmol, 2 eq) in DCM (5 mL) was stirred at rt for 16 h. The mixture was partitioned between water (50 mL) and EtOAc (50 mL). The organic layer was washed with brine (100 mL), dried over Na$_2$SO$_4$ and concentrated to give methyl 8-((5-((trans-4-(tert-butyl)cyclohexyl)oxy)naphthalen-2-yl)methyl)-8-azabicyclo[3.2.1]octane-3-carboxylate as a white solid (100 mg, Y: 72%).

$^1$H NMR (400 MHz, CDCl$_3$) δ: 8.33 (d, J=8.4 Hz, 1H), 7.84 (s, 1H), 7.53 (d, J=8.4 Hz, 1H), 7.44-7.38 (m, 2H), 6.92 (d, J=6.4 Hz, 1H), 4.34-4.29 (m, 3H), 3.94-3.93 (m, 2H), 3.67 (s, 3H), 2.77-2.70 (m, 1H), 2.48-2.28 (m, 6H), 2.00-1.86 (m, 6H), 1.57-1.48 (m, 2H), 1.22-1.12 (m, 3H), 0.90 (s, 9H); ESI-MS (M+H)$^+$: 464.3

Step 5: 8-((5-((trans-4-(tert-butyl)cyclohexyl)oxy)naphthalen-2-yl)methyl)-8-azabicyclo[3.2.1]octane-3-carboxylic acid

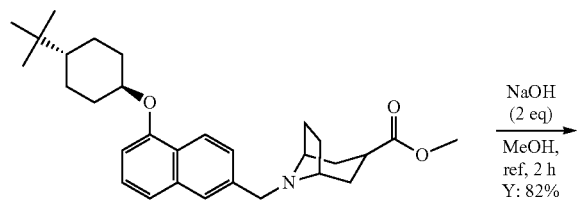

NaOH (2 eq)
MeOH, ref, 2 h
Y: 82%

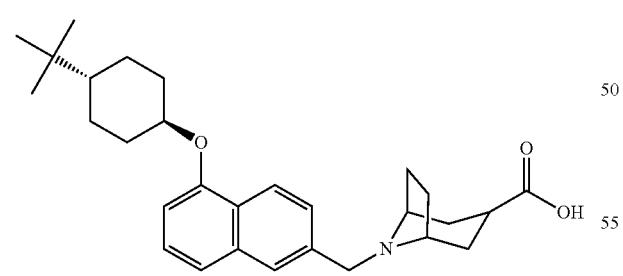

Into a solution of methyl 8-((5-((trans-4-(tert-butyl)cyclohexyl)oxy)naphthalen-2-yl)methyl)-8-azabicyclo[3.2.1]octane-3-carboxylate (100 mg, 0.22 mmol, 1.0 eq) in MeOH (10 mL) was added NaOH (17 mg, 0.43 mmol, 2.0 eq). The mixture was stirred at reflux for 1 h. After cooling down to rt, the mixture was concentrated and the residue was acidified to pH=6 with 1 N HCl. The solid was collected by filtration and washed with water. After dried under vacuum, 8-((5-((trans-4-(tert-butyl)cyclohexyl)oxy)naphthalen-2-yl)methyl)-8-azabicyclo[3.2.1]octane-3-carboxylic acid was obtained as a white solid (80 mg, Y: 82%).

$^1$H NMR (400 MHz, CDCl$_3$) δ: 8.34 (d, J=9.2 Hz, 1H), 7.99 (s, 1H), 7.56 (dd, J=1.6 Hz, 8.8 Hz, 1H), 7.49-7.46 (m, 2H), 7.06 (t, J=4.4 Hz, 1H), 4.46-4.36 (m, 3H), 4.03-4.01 (m, 2H), 3.00-2.96 (m, 1H), 2.52-2.50 (m, 2H), 2.34-2.32 (m, 2H), 2.16-2.10 (m, 5H), 1.96-1.93 (m, 2H), 1.58-1.49 (m, 2H), 1.33-1.14 (m, 4H), 0.93 (s, 9H); ESI-MS (M+H)$^+$: 450.0, HPLC: 100.00%-100.00%.

Example 2: 9-((5-((trans-4-(tert-butyl)cyclohexyl)oxy)naphthalen-2-yl)methyl)-9-azabicyclo[3.3.1]nonane-3-carboxylic acid Step 1: methyl 9-((5-((trans-4-(tert-butyl)cyclohexyl)oxy)naphthalen-2-yl)methyl)-9-azabicyclo[3.3.1]nonane-3-carboxylate

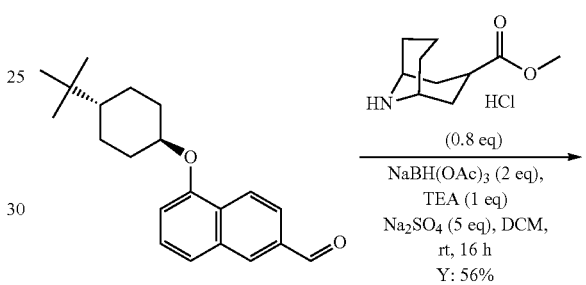

NaBH(OAc)$_3$ (2 eq),
TEA (1 eq)
Na$_2$SO$_4$ (5 eq), DCM,
rt, 16 h
Y: 56%

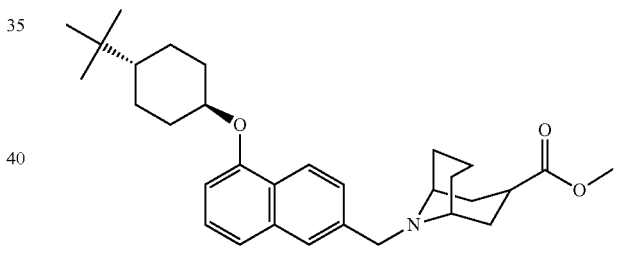

Methyl 9-((5-((trans-4-(tert-butyl)cyclohexyl)oxy)naphthalen-2-yl)methyl)-9-azabicyclo[3.3.1]nonane-3-carboxylate was obtained following the same procedure as synthesis of methyl 8-((5-((trans-4-(tert-butyl)cyclohexyl)oxy)naphthalen-2-yl)methyl)-8-azabicyclo[3.2.1]octane-3-carboxylate as yellow solid, 80 mg, Y: 56%. ESI-MS (M+H)$^+$: 478.3.

Step 2: 9-((5-((trans-4-(tert-butyl)cyclohexyl)oxy)naphthalen-2-yl)methyl)-9-azabicyclo[3.3.1]nonane-3-carboxylic acid

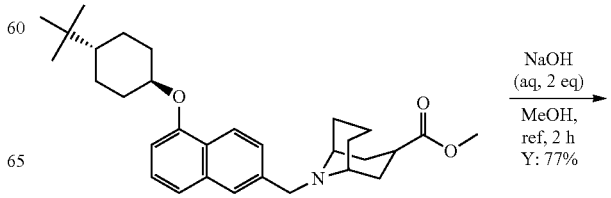

NaOH (aq, 2 eq)
MeOH, ref, 2 h
Y: 77%

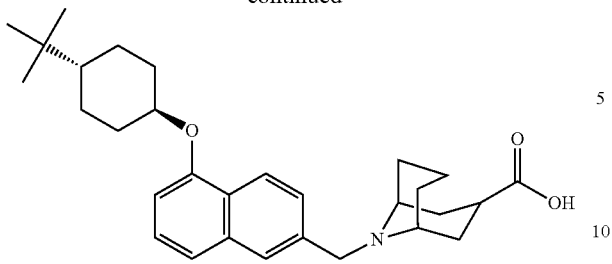

9-((5-((trans-4-(tert-butyl)cyclohexyl)oxy)naphthalen-2-yl)methyl)-9-azabicyclo[3.3.1]nonane-3-carboxylic acid was obtained following the same procedure as synthesis of 8-((5-((trans-4-(tert-butyl)cyclohexyl)oxy)naphthalen-2-yl)methyl)-8-azabicyclo[3.2.1]octane-3-carboxylic acid as yellow solid, 55 mg, Y: 77%.

$^1$H NMR (400 MHz, CDCl$_3$) δ: 8.32 (d, J=8.4 Hz, 1H), 8.04 (s, 1H), 7.61 (d, J=8.8 Hz, 1H), 7.47-7.46 (m, 2H), 7.04 (t, J=4.4 Hz, 1H), 4.66 (s, 2H), 4.45-4.40 (m, 1H), 3.57-3.56 (m, 2H), 3.14-3.07 (m, 1H), 2.40-2.31 (m, 6H), 2.15-2.08 (m, 3H), 1.96-1.75 (m, 5H), 1.58-1.48 (m, 2H), 1.33-1.14 (m, 3H), 0.93 (s, 9H); ESI-MS (M+H)$^+$: 464.0.

Example 3: 3-(((5-((trans-4-(tert-butyl)cyclohexyl)oxy)naphthalen-2-yl)methyl)amino)-2,2-dimethylcyclobutanecarboxylic acid Step 1: 5-hydroxy-2-naphthaldehyde

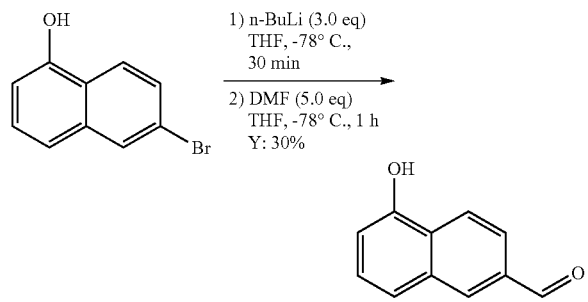

5-hydroxy-2-naphthaldehyde was obtained following the same procedure as synthesis of 5-((trans-4-(tert-butyl)cyclohexyl)oxy)-2-naphthaldehyde as yellow solid, 600 mg, Y: 30%.

$^1$H NMR (400 MHz, CDCl$_3$) δ: 10.17 (s, 1H), 8.33-8.30 (m, 2H), 7.95 (d, J=8.8 Hz, 1H), 7.60 (d, J=8.0 Hz, 1H), 7.42 (t, J=8.0 Hz, 1H), 6.99 (d, J=7.6 Hz, 1H), 5.50 (br s, 1H); ESI-MS (M+H)$^+$: 173.1.

Step 2: 5-((trans-4-(tert-butyl)cyclohexyl)oxy)-2-naphthaldehyde

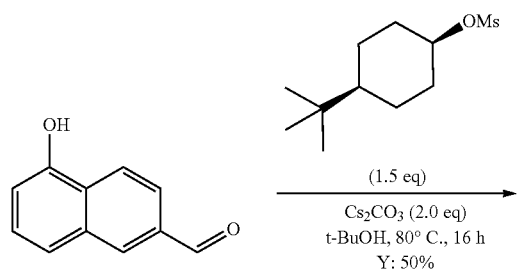

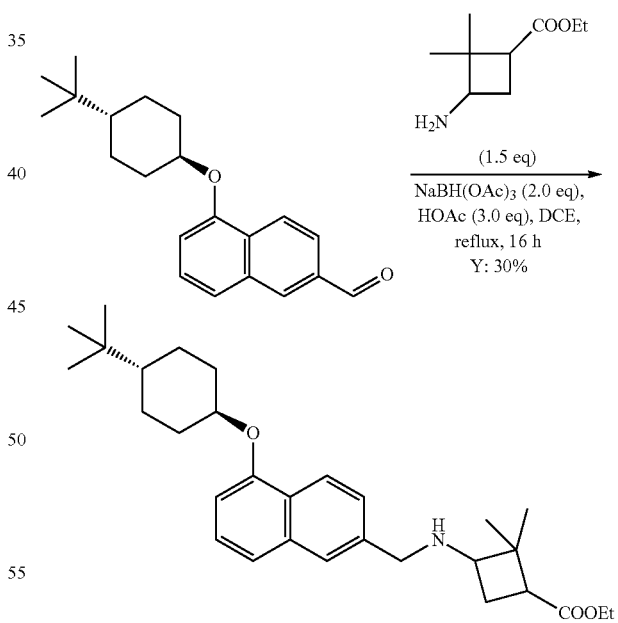

A mixture of 5-hydroxy-2-naphthaldehyde (340 mg, 2.0 mmol, 1.0 eq), cis-4-tert-butylcyclohexyl methanesulfonate (700 mg, 3.0 mmol, 1.5 eq) and Cs$_2$CO$_3$ (1.30 g, 4.0 mmol, 2.0 eq) in t-BuOH (5 mL) was heated at 80° C. for 16 h and cooled to rt. The mixture was partitioned between EtOAc (20 mL) and water (20 mL). The organic was dried and concentrated. The residue was purified by pre-TLC (petroleum ether/EtOAc=20:1) to give 5-((trans-4-(tert-butyl)cyclohexyl)oxy)-2-naphthaldehyde (300 mg, Y: 50%) as a yellow oil.

$^1$H NMR (400 MHz, CDCl$_3$) δ: 10.16 (s, 1H), 8.38 (d, J=8.8 Hz, 1H), 8.28 (d, J=1.6 Hz, 1H), 7.90 (dd, J=1.6 Hz, 8.8 Hz, 1H), 7.55 (d, J=8.0 Hz, 1H), 7.47 (t, J=8.0 Hz, 1H), 7.02 (d, J=8.0 Hz, 1H), 4.38-4.30 (m, 1H), 2.33-2.30 (m, 2H), 1.93-1.90 (m, 2H), 1.58-1.51 (m, 2H), 1.21-1.13 (m, 3H), 0.90 (s, 9H); ESI-MS (M+Na)$^+$: 333.2.

Step 3: ethyl 3-(((5-((trans-4-(tert-butyl)cyclohexyl)oxy)naphthalen-2-yl)methyl)amino)-2,2-dimethylcyclobutanecarboxylate A mixture of 5-((trans-4-(tert-butyl)cyclohexyl)oxy)-2-naphthaldehyde (62 mg, 0.2 mmol, 1.0 eq), ethyl 3-amino-2,2-dimethylcyclobutanecarboxylate (50 mg, 0.3 mmol, 1.5 eq), HOAc (36 mg, 0.6 mmol, 3.0 eq) and NaBH(OAc)$_3$ (85 mg, 0.4 mmol, 2.0 eq) in DCM (3 mL) was heated at reflux for 16 h. The mixture was partitioned between water (20 mL) and EtOAc (20 mL). The organic layer was washed with brine (20 mL) and concentrated to give a crude product, which was purified by pre-TLC (petroleum ether/EtOAc=2:1) to give ethyl 3-(((5-((trans-4-(tert-butyl)cyclohexyl)oxy)

naphthalen-2-yl)methyl)amino)-2,2-dimethylcyclobutanecarboxylate as a yellow oil (30 mg, Y: 30%). ESI-MS (M+H)⁺: 466.4.

Step 4: 3-(((5-((trans-4-(tert-butyl)cyclohexyl)oxy)naphthalen-2-yl)methyl)amino)-2,2-dimethylcyclobutanecarboxylic acid

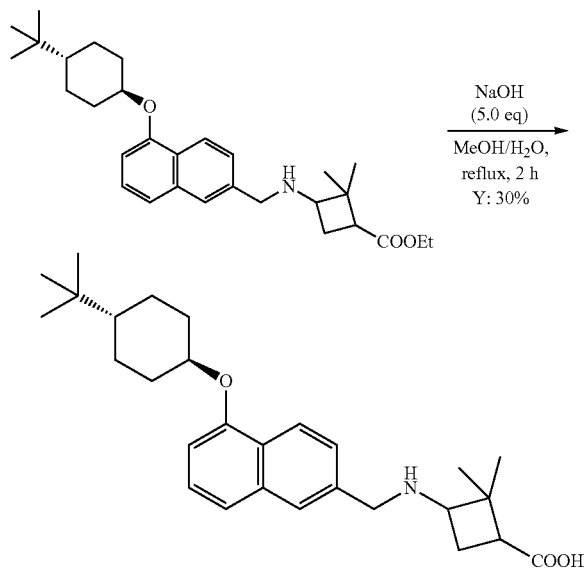

Into a solution of ethyl 3-(((5-((trans-4-(tert-butyl)cyclohexyl)oxy)naphthalen-2-yl)methyl)amino)-2,2-dimethylcyclobutanecarboxylate (30 mg, 0.08 mmol, 1.0 eq) in MeOH/H₂O (4:1, 2 mL) was added NaOH (16 mg, 0.40 mmol, 5.0 eq). The mixture was heated at reflux for 2 h. After cooling to rt, the mixture was concentrated and the residue was adjusted to pH=6 with 1 N HCl. The solid was purified by pre-HPLC (ACN and H₂O as mobile phase) to give 3-(((5-((trans-4-(tert-butyl)cyclohexyl)oxy)naphthalen-2-yl)methyl)amino)-2,2-dimethylcyclobutanecarboxylic acid as a white solid (8 mg, Y: 30%).

¹H NMR (400 MHz, CD₃OD) δ: 8.16 (d, J=8.4 Hz, 1H), 7.78 (s, 1H), 7.40 (dd, J=1.6 Hz, 8.4 Hz, 1H), 7.33-7.31 (m, 2H), 6.90-6.87 (m, 1H), 4.31-4.25 (m, 1H), 4.09 (AB, 2H), 3.17 (t, J=6.8 Hz, 1H), 2.44 (t, J=7.6 Hz, 1H), 2.28-2.19 (m, 3H), 2.12-2.05 (m, 1H), 1.82-1.80 (m, 2H), 1.45-1.36 (m, 2H), 1.23 (s, 3H), 1.20-1.10 (m, 3H), 1.05 (s, 3H), 0.81 (s, 9H); ESI-MS (M+H)⁺: 438.3.

Example 4: 1-((5-((trans-4-(tert-butyl)cyclohexyl)oxy)naphthalen-2-yl)methyl)azetidine-3-carboxylic acid Step 1: methyl 1-((5-((trans-4-(tert-butyl)cyclohexyl)oxy)naphthalen-2-yl)methyl)azetidine-3-carboxylate

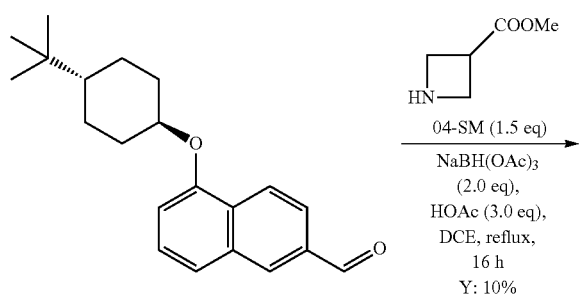

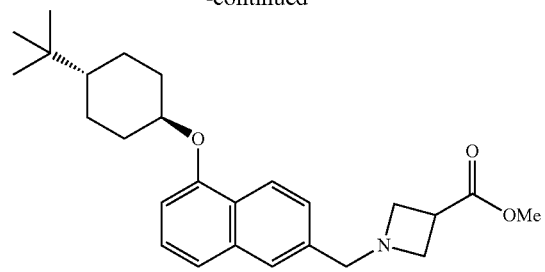

Methyl 1-((5-((trans-4-(tert-butyl)cyclohexyl)oxy)naphthalen-2-yl)methyl)azetidine-3-carboxylate was obtained following the same procedure as ethyl 3-(((5-((trans-4-(tert-butyl)cyclohexyl)oxy)naphthalen-2-yl)methyl)amino)-2,2-dimethylcyclobutanecarboxylate as a yellow oil (10 mg, Y: 10%). ESI-MS (M+H)⁺: 410.3.

Step 2: 1-((5-((trans-4-(tert-butyl)cyclohexyl)oxy)naphthalen-2-yl)methyl)azetidine-3-carboxylic acid

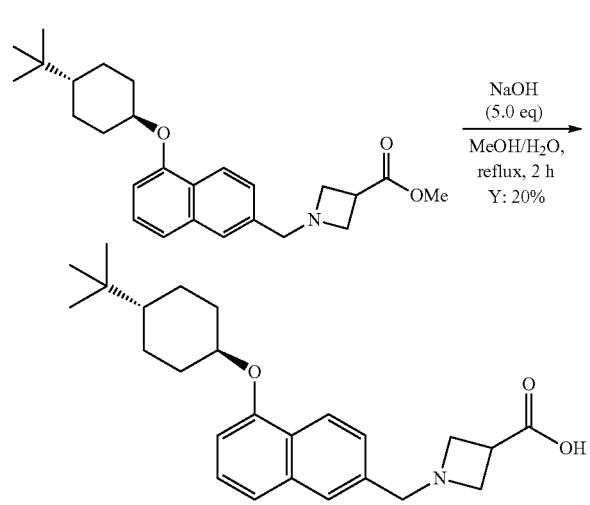

1-((5-((trans-4-(tert-butyl)cyclohexyl)oxy)naphthalen-2-yl)methyl)azetidine-3-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow oil (4 mg, Y: 20%).

¹H NMR (400 MHz, CD₃OD) δ: 8.16 (d, J=8.8 Hz, 1H), 7.77 (s, 1H), 7.34-7.32 (m, 3H), 6.93-6.88 (m, 1H), 4.34-4.27 (m, 3H), 4.00-3.98 (m, 4H), 3.29-3.25 (m, 1H), 2.22-2.20 (m, 2H), 1.83-1.80 (m, 2H), 1.45-1.36 (m, 2H), 1.20-1.05 (m, 3H), 0.82 (s, 9H); ESI-MS (M+H)⁺: 396.1.

Example 5: 2-((5-((trans-4-(tert-butyl)cyclohexyl)oxy)naphthalen-2-yl)methyl)octahydrocyclopenta[c]pyrrole-5-carboxylic acid Step 1: methyl 2-((5-((trans-4-(tert-butyl)cyclohexyl)oxy)naphthalen-2-yl)methyl)octahydrocyclopenta[c]pyrrole-5-carboxylate

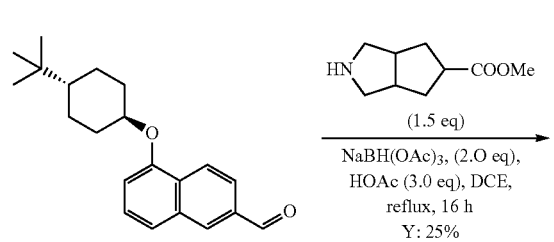

51

-continued

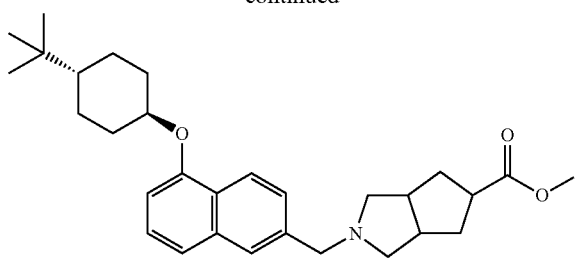

methyl 2-((5-((trans-4-(tert-butyl)cyclohexyl)oxy)naphthalen-2-yl)methyl)octahydrocyclopenta[c]pyrrole-5-carboxylate was obtained following the same procedure as ethyl 3-(((5-((trans-4-(tert-butyl)cyclohexyl)oxy)naphthalen-2-yl)methyl)amino)-2,2-dimethylcyclobutanecarboxylate as a yellow oil (30 mg, Y: 25%). ESI-MS (M+H)+: 464.4.

Step 2: -((5-((trans-4-(tert-butyl)cyclohexyl)oxy)naphthalen-2-yl)methyl)octahydrocyclopenta[c]pyrrole-5-carboxylic acid

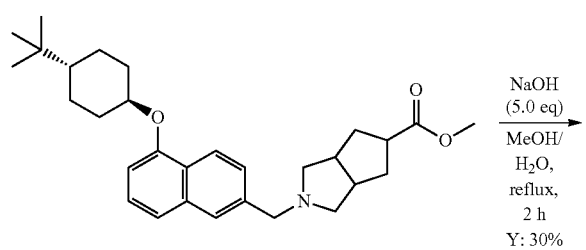

2-((5-((trans-4-(tert-butyl)cyclohexyl)oxy)naphthalen-2-yl)methyl)octahydrocyclopenta[c]pyrrole-5-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow solid (10 mg, Y: 30%).

$^1$H NMR (400 MHz, CD$_3$OD) δ: 8.10 (d, J=8.8 Hz, 1H), 7.69 (s, 1H), 7.39 (dd, J=1.6 Hz, 8.8 Hz, 1H), 7.31-7.25 (m, 2H), 6.84 (dd, J=1.6 Hz, 6.4 Hz, 1H), 4.30-4.23 (m, 1H), 3.92 (s, 2H), 2.78-2.54 (m, 7H), 2.22-2.18 (m, 2H), 2.07-2.00 (m, 2H), 1.82-1.78 (m, 2H), 1.65-1.59 (m, 2H), 1.45-1.35 (m, 2H), 1.19-1.00 (m, 3H), 0.81 (s, 9H); ESI-MS (M+H)+: 450.3.

52

Example 6: 1-((5-((trans-4-(tert-butyl)cyclohexyl)oxy)naphthalen-2-yl)methyl)pyrrolidine-3-carboxylic acid Step 1: methyl 1-((5-((trans-4-(tert-butyl)cyclohexyl)oxy)naphthalen-2-yl)methyl)pyrrolidine-3-carboxylate

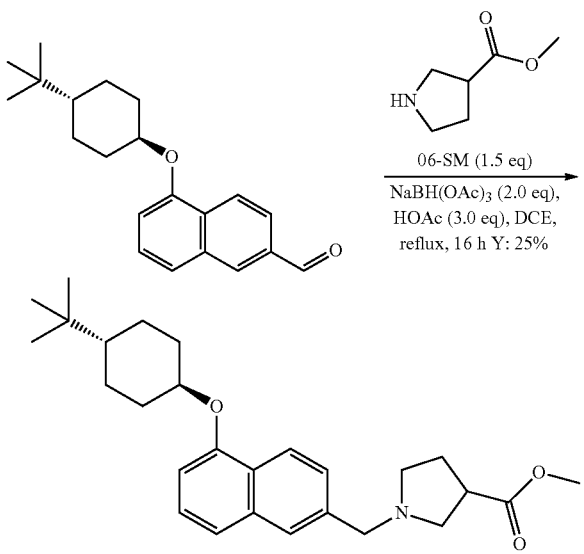

Methyl 1-((5-((trans-4-(tert-butyl)cyclohexyl)oxy)naphthalen-2-yl)methyl)pyrrolidine-3-carboxylate was obtained following the same procedure as ethyl 3-(((5-((trans-4-(tert-butyl)cyclohexyl)oxy)naphthalen-2-yl)methyl)amino)-2,2-dimethylcyclobutanecarboxylate as a yellow oil (20 mg, Y: 25%). ESI-MS (M+H)+: 424.4.

Step 2: 1-((5-((trans-4-(tert-butyl)cyclohexyl)oxy)naphthalen-2-yl)methyl)pyrrolidine-3-carboxylic acid

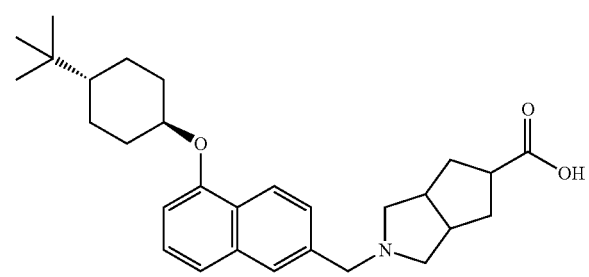

1-((5-((trans-4-(tert-butyl)cyclohexyl)oxy)naphthalen-2-yl)methyl)pyrrolidine-3-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow solid (6 mg, Y: 30%).

$^1$H NMR (400 MHz, CD$_3$OD) δ: 8.15 (d, J=8.4 Hz, 1H), 7.78 (s, 1H), 7.39 (dd, J=1.6 Hz, 8.4 Hz, 1H), 7.32-7.31 (m, 2H), 6.89-6.87 (m, 1H), 4.31-4.15 (m, 3H), 3.22-3.20 (m, 2H), 3.10-3.06 (m, 2H), 2.99-2.91 (m, 1H), 2.22-2.10 (m, 4H), 1.83-1.80 (m, 2H), 1.45-1.36 (m, 2H), 1.20-1.01 (m, 3H), 0.81 (s, 9H); ESI-MS (M+H)$^+$: 410.3.

Example 7: 3-(((5-((trans-4-(tert-butyl)cyclohexyl)oxy)naphthalen-2-yl)methyl)amino)cyclobutanecarboxylic acid Step 1: ethyl 3-(((5-((trans-4-(tert-butyl)cyclohexyl)oxy)naphthalen-2-yl)methyl)amino)cyclobutanecarboxylate

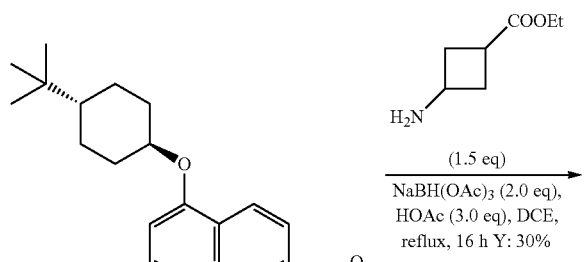

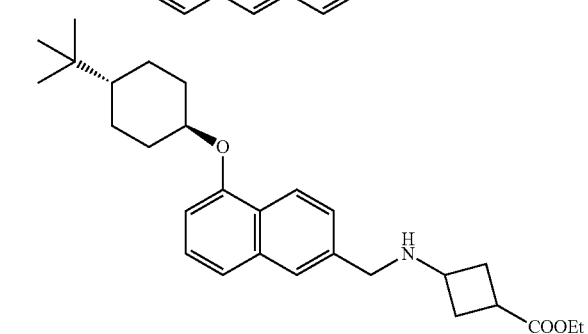

Ethyl 3-(((5-((trans-4-(tert-butyl)cyclohexyl)oxy)naphthalen-2-yl)methyl)amino)cyclobutanecarboxylate was obtained following the same procedure as ethyl 3-(((5-((trans-4-(tert-butyl)cyclohexyl)oxy)naphthalen-2-yl)methyl)amino)-2,2-dimethylcyclobutanecarboxylate as a yellow oil (30 mg, Y: 35%). ESI-MS (M+H)$^+$: 438.4.

Step 2: 3-(((5-((trans-4-(tert-butyl)cyclohexyl)oxy)naphthalen-2-yl)methyl)amino)cyclobutanecarboxylic acid

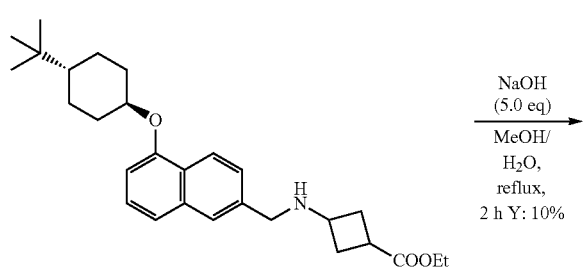

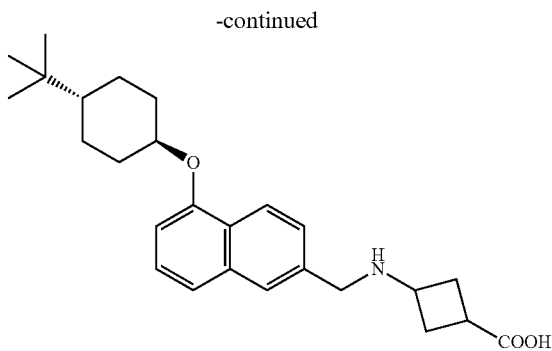

3-(((5-((trans-4-(tert-butyl)cyclohexyl)oxy)naphthalen-2-yl)methyl)amino)cyclobutanecarboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow solid (2 mg, Y: 10%).

$^1$H NMR (400 MHz, CD$_3$OD) δ: 8.16 (d, J=8.8 Hz, 1H), 7.76 (s, 1H), 7.38 (dd, J=1.6 Hz, 8.8 Hz, 1H), 7.33-7.31 (m, 2H), 6.91-6.86 (m, 1H), 4.34-4.26 (m, 1H), 4.05 (s, 2H), 3.51-3.47 (m, 1H), 2.74-2.67 (m, 1H), 2.49-2.42 (m, 2H), 2.23-2.09 (m, 4H), 1.84-1.82 (m, 2H), 1.46-1.37 (m, 2H), 1.18-1.02 (m, 3H), 0.82 (s, 9H); ESI-MS (M+H)$^+$: 410.3.

Example 8: 1-((5-((trans-4-(tert-butyl)cyclohexyl)oxy)naphthalen-2-yl)methyl)azepane-4-carboxylic acid Step 1: methyl 1-((5-((trans-4-(tert-butyl)cyclohexyl)oxy)naphthalen-2-yl)methyl)azepane-4-carboxylate

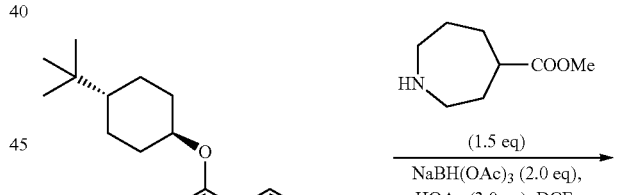

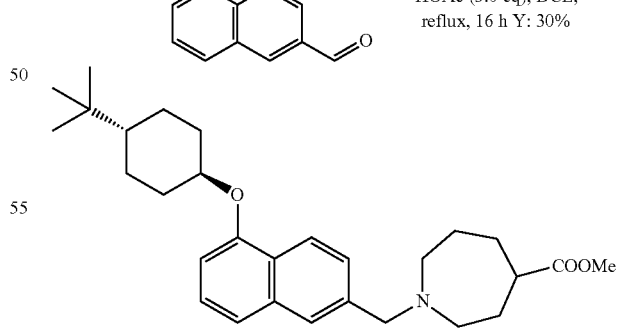

Methyl 1-((5-((trans-4-(tert-butyl)cyclohexyl)oxy)naphthalen-2-yl)methyl)azepane-4-carboxylate was obtained following the same procedure as ethyl 3-(((5-((trans-4-(tert-butyl)cyclohexyl)oxy)naphthalen-2-yl)methyl)amino)-2,2-dimethylcyclobutanecarboxylate as a yellow oil (30 mg, Y: 30%). ESI-MS (M+H)$^+$: 452.4.

Step 2: 1-((5-((trans-4-(tert-butyl)cyclohexyl)oxy)naphthalen-2-yl)methyl)azepane-4-carboxylic acid

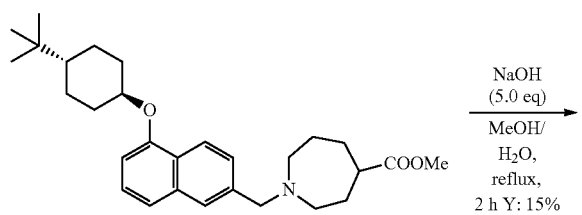

1-((5-((trans-4-(tert-butyl)cyclohexyl)oxy)naphthalen-2-yl)methyl)azepane-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow solid (5 mg, Y: 15%).

$^1$H NMR (400 MHz, CD$_3$OD) δ: 8.13 (d, J=8.8 Hz, 1H), 7.74 (s, 1H), 7.41 (d, J=8.4 Hz, 1H), 7.32-7.30 (m, 2H), 6.87 (d, J=5.6 Hz, 1H), 4.32-4.26 (m, 1H), 4.08 (AB, 2H), 3.16-2.86 (m, 4H), 2.58-2.55 (m, 1H), 2.22-2.19 (m, 2H), 2.01-1.68 (m, 8H), 1.46-1.37 (m, 2H), 1.20-0.97 (m, 3H), 0.82 (s, 9H); ESI-MS (M+H)$^+$: 438.2.

Example 9: 1-((5-((trans-4-(trifluoromethyl)cyclohexyl)oxy)naphthalen-2-yl)methyl)piperidine-4-carboxylic acid Step 1: ethyl 1-((5-hydroxynaphthalen-2-yl)methyl)piperidine-4-carboxylate

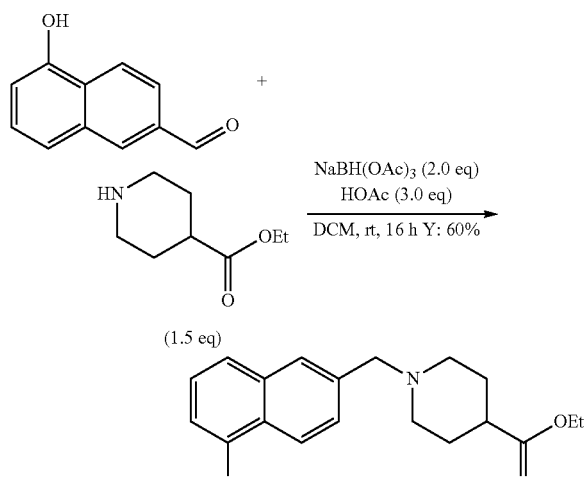

A mixture of 5-hydroxy-2-naphthaldehyde (500 mg, 3.0 mmol, 1.0 eq), ethyl piperidine-4-carboxylate (700 mg, 4.5 mmol, 1.5 eq), HOAc (540 mg, 9.0 mmol, 3.0 eq) and NaBH(OAc)$_3$ (1.2 g, 6.0 mmol, 2.0 eq) in DCM (15 mL) was stirred at rt for 16 h. The mixture was partitioned between water (200 mL) and EtOAc (200 mL). The organic layer was washed with brine (100 mL), dried over Na$_2$SO$_4$ and concentrated to yield a crude product, which was used for next step without further purification (420 mg, Y: 60%). ESI-MS (M+H)$^+$: 314.2.

Step 2: ethyl 1-((5-((trans-4-(trifluoromethyl)cyclohexyl)oxy)naphthalen-2-yl)methyl)piperidine-4-carboxylate

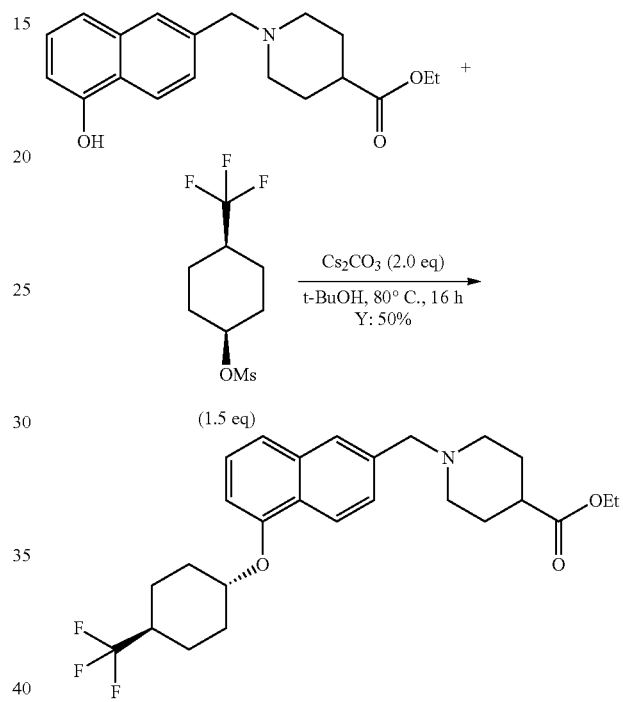

A mixture of ethyl 1-((5-hydroxynaphthalen-2-yl)methyl)piperidine-4-carboxylate (93 mg, 0.3 mmol, 1.0 eq), cis-4-(trifluoromethyl)cyclohexyl methanesulfonate (120 mg, 0.5 mmol, 1.5 eq) and Cs$_2$CO$_3$ (200 mg, 0.6 mmol, 2.0 eq) in t-BuOH (2 mL) was heated at 80° C. for 16 h and cooled to rt. The mixture was filtered and the filtrate was purified by pre-TLC (petroleum ether/EtOAc=5:1) to give ethyl 1-((5-((trans-4-(trifluoromethyl)cyclohexyl)oxy)naphthalen-2-yl)methyl)piperidine-4-carboxylate (50 mg, Y: 50%) as a yellow oil. ESI-MS (M+H)$^+$: 464.3.

Step 3: 1-((5-((trans-4-(trifluoromethyl)cyclohexyl)oxy)naphthalen-2-yl)methyl)piperidine-4-carboxylic acid

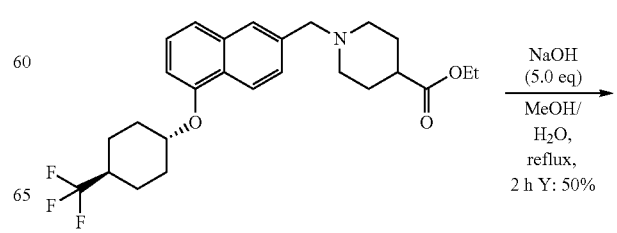

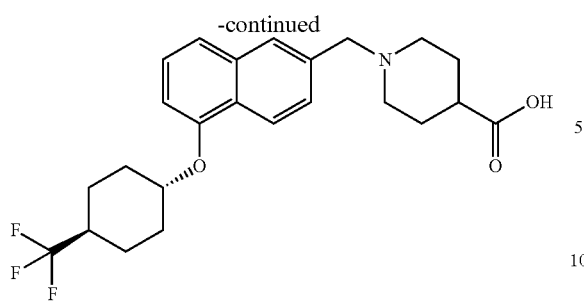

1-((5-(((trans-4-(trifluoromethyl)cyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (20 mg, Y: 50%).

$^1$H NMR (400 MHz, CD$_3$OD) δ: 8.12 (d, J=8.8 Hz, 1H), 7.74 (s, 1H), 7.38 (d, J=8.4 Hz, 1H), 7.34-7.29 (m, 2H), 6.90 (dd, J=2.0 Hz, 6.4 Hz, 1H), 4.38-4.32 (m, 1H), 3.97 (s, 2H), 3.10-3.07 (m, 2H), 2.56-2.53 (m, 2H), 2.23-2.10 (m, 4H), 1.94-1.74 (m, 6H), 1.52-1.37 (m, 4H); ESI-MS (M+H)$^+$: 436.2.

Example 10: 1-((5-(((cis-4-(trifluoromethyl)cyclohexyl)oxy)naphthalen-2-yl)methyl)piperidine-4-carboxylic acid Step 1: ethyl 1-((5-(((cis-4-(trifluoromethyl)cyclohexyl)oxy)naphthalen-2-yl)methyl)piperidine-4-carboxylate

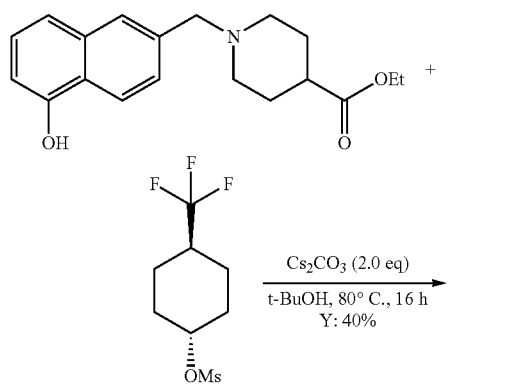

ethyl 1-((5-(((cis-4-(trifluoromethyl)cyclohexyl)oxy)naphthalen-2-yl)methyl)piperidine-4-carboxylate was obtained following the same procedure as ethyl 1-((5-(((trans-4-(trifluoromethyl)cyclohexyl)oxy)naphthalen-2-yl)methyl)piperidine-4-carboxylate as a yellow oil (40 mg, Y: 40%). ESI-MS (M+H)$^+$: 464.3.

Step 2: 1-((5-(((cis-4-(trifluoromethyl)cyclohexyl)oxy)naphthalen-2-yl)methyl)piperidine-4-carboxylic acid

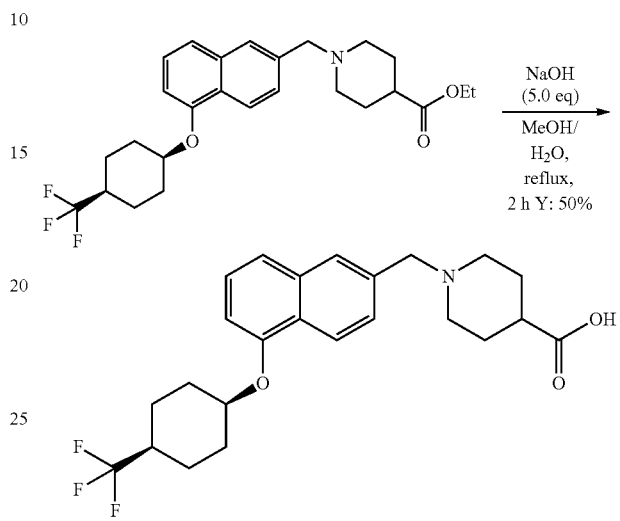

1-((5-(((cis-4-(trifluoromethyl)cyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (20 mg, Y: 50%).

$^1$H NMR (400 MHz, CD$_3$OD) δ: 8.22 (d, J=8.8 Hz, 1H), 7.82 (s, 1H), 7.44 (dd, J=1.2 Hz, 8.4 Hz, 1H), 7.36-7.34 (m, 2H), 6.92-6.89 (m, 1H), 4.80-4.78 (m, 1H), 4.17 (s, 2H), 3.26-3.20 (m, 2H), 2.82-2.77 (m, 2H), 2.26-2.14 (m, 4H), 1.96-1.92 (m, 2H), 1.83-1.62 (m, 8H); ESI-MS (M+H)$^+$: 436.2.

Example 11: 1-((5-(((cis-4-isopropylcyclohexyl)oxy)naphthalen-2-yl)methyl)piperidine-4-carboxylic acid Step 1: ethyl 1-((5-(((cis-4-isopropylcyclohexyl)oxy)naphthalen-2-yl)methyl)piperidine-4-carboxylate

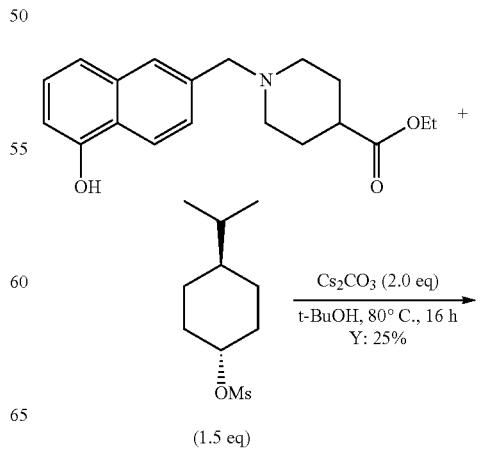

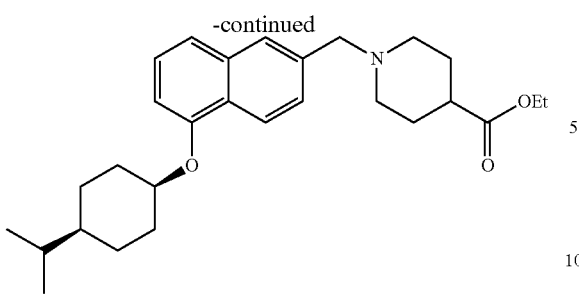

ethyl 1-((5-((cis-4-isopropylcyclohexyl)oxy)naphthalen-2-yl)methyl)piperidine-4-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (30 mg, Y: 25%). ESI-MS (M+H)⁺: 438.4.

Step 2: 1-((5-((cis-4-isopropylcyclohexyl)oxy)naphthalen-2-yl)methyl)piperidine-4-carboxylic acid

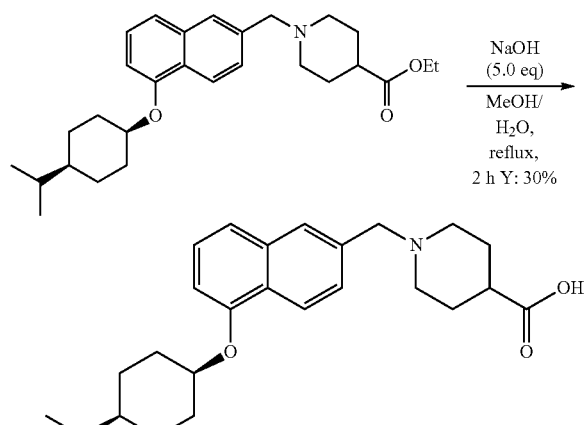

1-((5-((cis-4-isopropylcyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (13 mg, Y: 30%).
¹H NMR (400 MHz, CD₃OD) δ: 8.23 (d, J=8.8 Hz, 1H), 7.81 (s, 1H), 7.42 (dd, J=1.6 Hz, 8.4 Hz, 1H), 7.33-7.30 (m, 2H), 6.86-6.84 (m, 1H), 4.70 (s, 1H), 4.16 (s, 2H), 3.24-3.21 (m, 2H), 2.81-2.76 (m, 2H), 2.39-2.35 (m, 1H), 2.17-1.88 (m, 6H), 1.67-1.45 (m, 7H), 1.24-1.19 (m, 1H), 0.91 (d, J=6.8 Hz, 6H); ESI-MS (M+H)⁺: 410.3.

Example 12: 1-((5-((cis-4-ethylcyclohexyl)oxy)naphthalen-2-yl)methyl)piperidine-4-carboxylic acid Step 1: ethyl 1-((5-((cis-4-ethylcyclohexyl)oxy)naphthalen-2-yl)methyl)piperidine-4-carboxylate

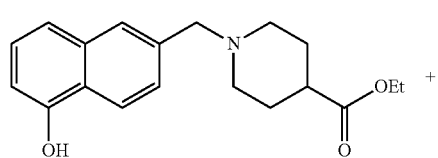 +

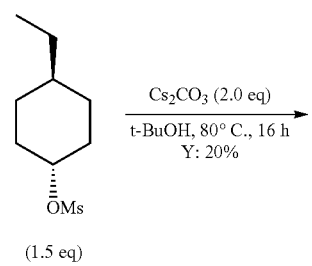

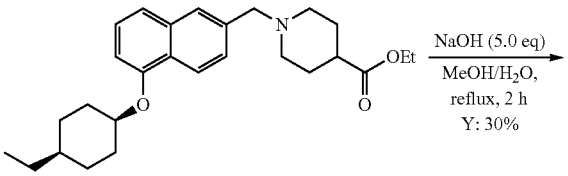

Ethyl 1-((5-((cis-4-ethylcyclohexyl)oxy)naphthalen-2-yl)methyl)piperidine-4-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (20 mg, Y: 20%). ESI-MS (M+H)⁺: 424.3.

Step 2: 1-((5-((cis-4-ethylcyclohexyl)oxy)naphthalen-2-yl)methyl)piperidine-4-carboxylic acid

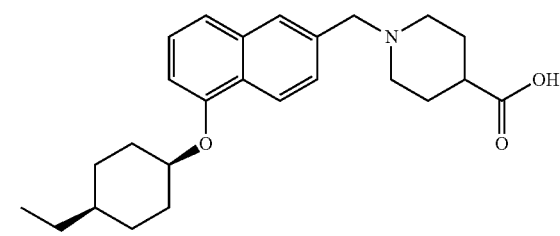

1-((5-((cis-4-ethylcyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (6 mg, Y: 30%).
¹H NMR (400 MHz, CD₃OD) δ: 8.19 (d, J=8.4 Hz, 1H), 7.72 (s, 1H), 7.39 (dd, J=1.6 Hz, 8.4 Hz, 1H), 7.33-7.27 (m, 2H), 6.86-6.81 (m, 1H), 4.72 (s, 1H), 3.91 (s, 2H), 3.08-3.05 (m, 2H), 2.48-4.42 (m, 2H), 2.18-2.03 (m, 4H), 1.89-1.69 (m, 4H), 1.62-1.51 (m, 4H), 1.43-1.34 (m, 2H), 1.25-1.22 (m, 2H), 0.84 (t, J=7.2 Hz, 3H); ESI-MS (M+H)⁺: 396.3.

Example 13: 1-((5-((trans-4-isopropylcyclohexyl)oxy)naphthalen-2-yl)methyl)piperidine-4-carboxylic acid

Step 1: ethyl 1-((5-((trans-4-isopropylcyclohexyl)oxy)naphthalen-2-yl)methyl)piperidine-4-carboxylate

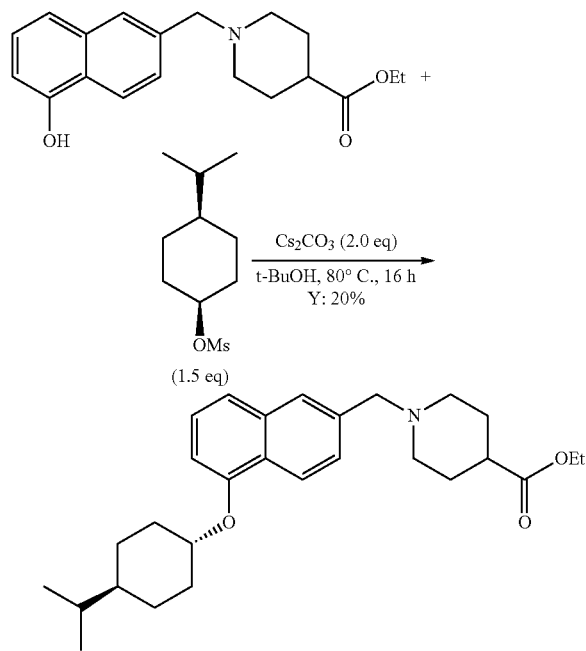

Ethyl 1-((5-((trans-4-isopropylcyclohexyl)oxy)naphthalen-2-yl)methyl)piperidine-4-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (20 mg, Y: 20%). ESI-MS (M+H)$^+$: 438.3.

Step 2: 1-((5-((trans-4-isopropylcyclohexyl)oxy)naphthalen-2-yl)methyl)piperidine-4-carboxylic acid

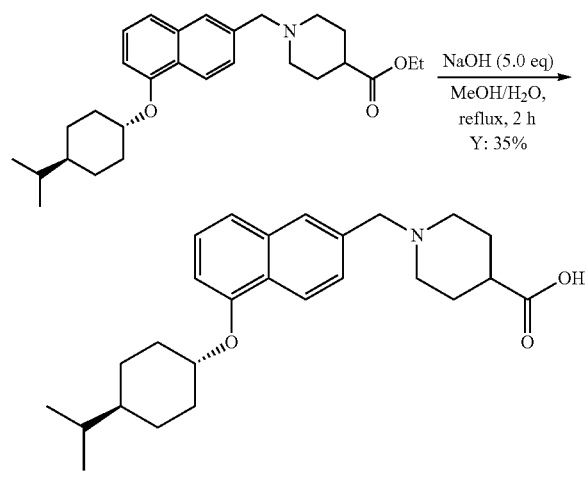

1-((5-((trans-4-isopropylcyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (7 mg, Y: 35%).

$^1$H NMR (400 MHz, CD$_3$OD) δ: 8.16 (d, J=8.4 Hz, 1H), 7.78 (s, 1H), 7.38 (dd, J=1.2 Hz, 8.8 Hz, 1H), 7.33-7.30 (m, 2H), 6.92-6.87 (m, 1H), 4.33-4.26 (m, 1H), 4.14 (s, 2H), 3.23-3.20 (m, 2H), 2.80-2.75 (m, 2H), 2.28-2.16 (m, 3H), 1.95-1.74 (m, 6H), 1.45-1.36 (m, 3H), 1.18-1.04 (m, 3H), 0.82 (d, J=6.8 Hz, 6H); ESI-MS (M+H)$^+$: 410.3.

Example 14: 1-((5-((trans-4-ethylcyclohexyl)oxy)naphthalen-2-yl)methyl)piperidine-4-carboxylic acid

Step 1: ethyl 1-((5-((trans-4-ethylcyclohexyl)oxy)naphthalen-2-yl)methyl)piperidine-4-carboxylate

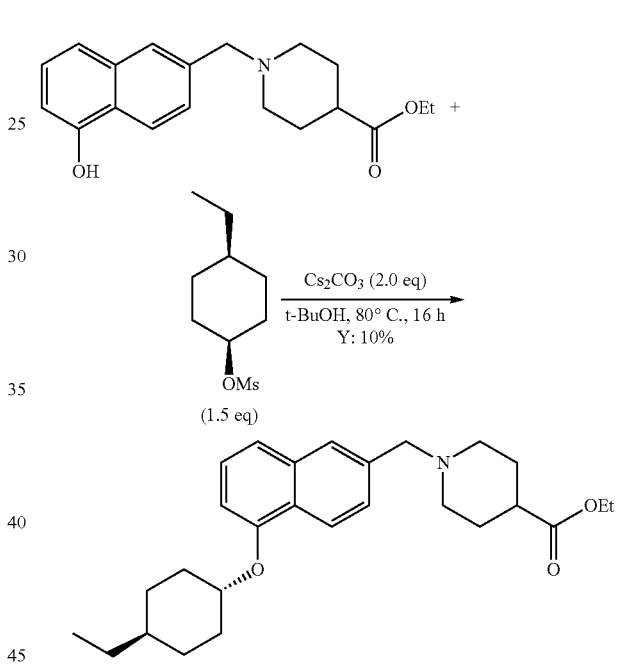

Ethyl 1-((5-((trans-4-ethylcyclohexyl)oxy)naphthalen-2-yl)methyl)piperidine-4-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (20 mg, Y: 10%). ESI-MS (M+H)$^+$: 424.3.

Step 2: 1-((5-((trans-4-ethylcyclohexyl)oxy)naphthalen-2-yl)methyl)piperidine-4-carboxylic acid

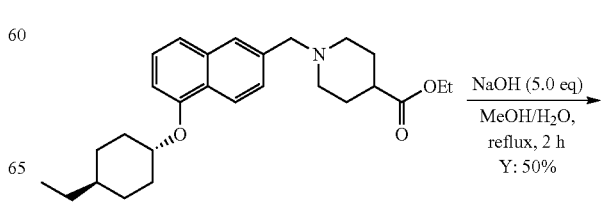

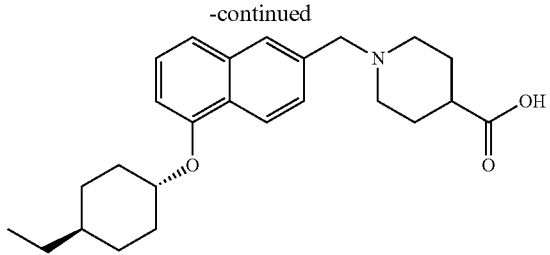

1-((5-((trans-4-ethylcyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acias a white solid (10 mg, Y: 50%).

$^1$H NMR (400 MHz, CD$_3$OD) δ: 8.13 (d, J=8.4 Hz, 1H), 7.73 (s, 1H), 7.36 (dd, J=1.6 Hz, 8.8 Hz, 1H), 7.31-7.28 (m, 2H), 6.89-6.86 (m, 1H), 4.35-4.27 (m, 1H), 3.97 (s, 2H), 3.11-3.09 (m, 2H), 2.58-2.52 (m, 2H), 2.16-2.13 (m, 3H), 1.89-1.71 (m, 6H), 1.48-1.38 (m, 2H), 1.21-0.96 (m, 5H), 0.83 (t, J=7.2 Hz, 3H); ESI-MS (M+H)$^+$: 396.3.

Example 15: 1-((5-((trans-4-methylcyclohexyl)oxy)naphthalen-2-yl)methyl)piperidine-4-carboxylic acid Step 1: ethyl 1-((5-((trans-4-methylcyclohexyl)oxy)naphthalen-2-yl)methyl)piperidine-4-carboxylate

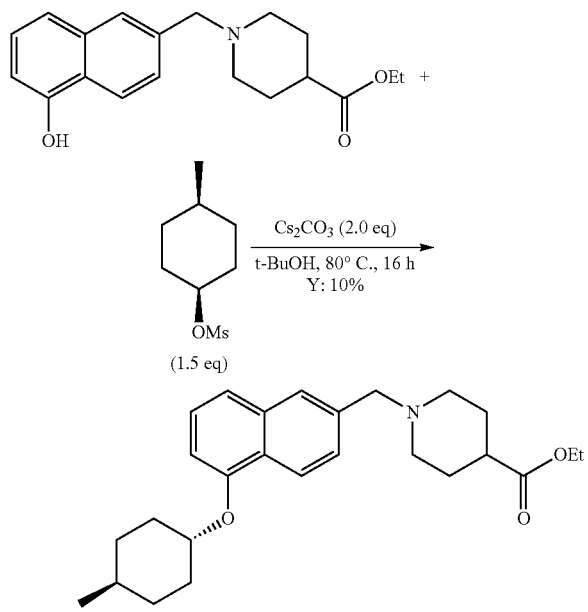

Ethyl 1-((5-((trans-4-methylcyclohexyl)oxy)naphthalen-2-yl)methyl)piperidine-4-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (20 mg, Y: 10%). ESI-MS (M+H)$^+$: 410.3.

Step 2: 1-((5-((trans-4-methylcyclohexyl)oxy)naphthalen-2-yl)methyl)piperidine-4-carboxylic acid

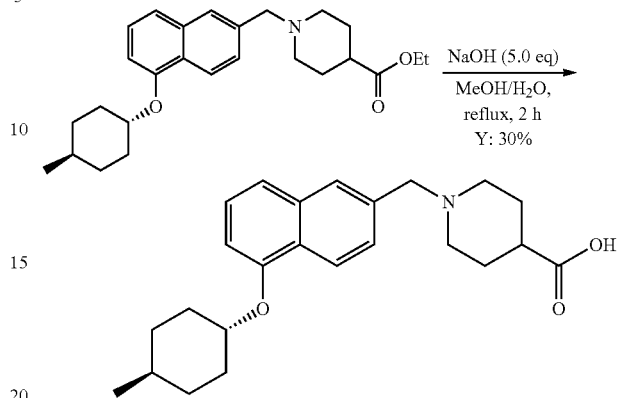

1-((5-((trans-4-methylcyclohexyl)oxy)naphthalen-2-yl)methyl)piperidine-4-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (6 mg, Y: 30%).

$^1$H NMR (400 MHz, CDCl$_3$) δ: 8.23 (d, J=8.4 Hz, 1H), 7.73 (s, 1H), 7.45 (d, J=8.8 Hz, 1H), 7.36-7.34 (m, 2H), 6.86-6.84 (m, 1H), 4.35-4.30 (m, 1H), 4.03 (s, 2H), 3.24-3.20 (m, 2H), 2.40-2.20 (m, 5H), 2.04-1.80 (m, 6H), 1.60-1.44 (m, 3H), 1.14-1.03 (m, 2H), 0.93 (d, J=6.4 Hz, 3H); ESI-MS (M+H)$^+$: 382.2.

Example 16: 1-((5-((4,4-dimethylcyclohexyl)oxy)naphthalen-2-yl)methyl)piperidine-4-carboxylic acid Step 1: ethyl 1-((5-((4,4-dimethylcyclohexyl)oxy)naphthalen-2-yl)methyl)piperidine-4-carboxylate

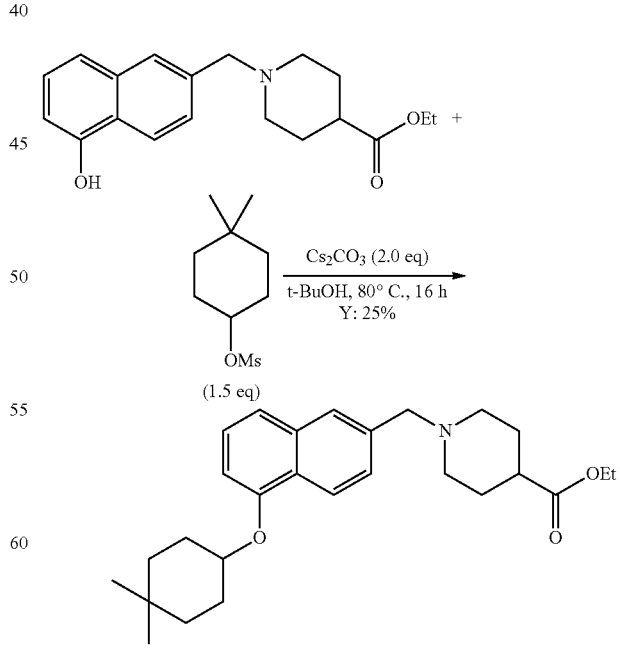

Ethyl 1-((5-((4,4-dimethylcyclohexyl)oxy)naphthalen-2-yl)methyl)piperidine-4-carboxylate was obtained following the same procedure as ethyl 1-((5-(((trans-4-(trifluoromethyl)cyclohexyl)oxy)naphthalen-2-yl)methyl)piperidine-4-carboxylate as a yellow oil (30 mg, Y: 25%). ESI-MS (M+H)⁺: 424.3.

Step 2: 1-((5-(((4,4-dimethylcyclohexyl)oxy)naphthalen-2-yl)methyl)piperidine-4-carboxylic acid

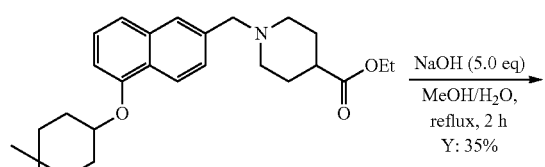

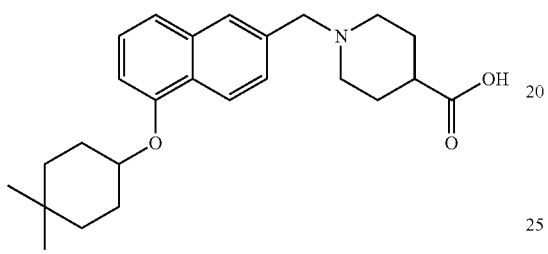

1-((5-(((4,4-dimethylcyclohexyl)oxy)naphthalen-2-yl)methyl)piperidine-4-carboxylic acid was obtained following the same procedure as 3-(((5-(((trans-4-(tert-butyl)cyclohexyl)oxy)naphthalen-2-yl)methyl)amino)-2,2-dimethylcyclobutanecarboxylic acid as a yellow oil (10 mg, Y: 35%).

$^1$H NMR (400 MHz, CD$_3$OD) δ: 8.20 (d, J=9.2 Hz, 1H), 7.80 (s, 1H), 7.40 (dd, J=1.6 Hz, 8.8 Hz, 1H), 7.36-7.30 (m, 2H), 6.91-6.86 (m, 1H), 4.49-4.45 (m, 1H), 4.16 (s, 2H), 3.24-3.22 (m, 2H), 2.82-2.76 (m, 2H), 2.28-2.23 (m, 1H), 1.96-1.69 (m, 8H), 1.53-1.47 (m, 2H), 1.28-1.21 (m, 2H), 0.90 (d, J=7.6 Hz, 6H); ESI-MS (M+H)⁺: 396.3.

Example 17: 1-((5-((trans-4-methylcyclohexyl)oxy)naphthalen-2-yl)methyl)azetidine-3-carboxylic acid Step 1: methyl 1-((5-hydroxynaphthalen-2-yl)methyl)azetidine-3-carboxylate

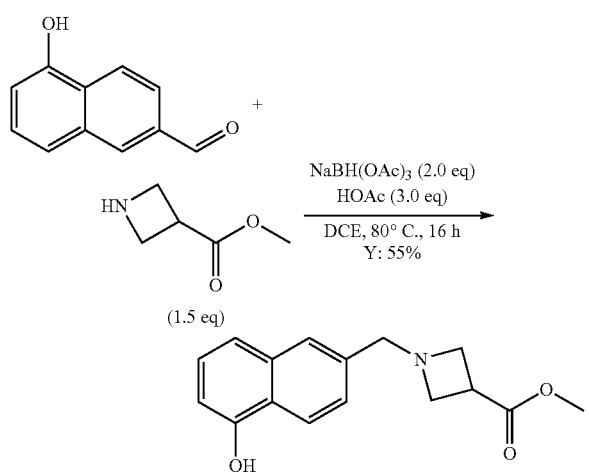

Methyl 1-((5-hydroxynaphthalen-2-yl)methyl)azetidine-3-carboxylate was obtained following the same procedure as ethyl 1-((5-hydroxynaphthalen-2-yl)methyl)piperidine-4-carboxylate as a yellow solid (350 mg, Y: 55%). ESI-MS (M+H)⁺: 272.1.

Step 2: methyl 1-((5-(((trans-4-methylcyclohexyl)oxy)naphthalen-2-yl)methyl)azetidine-3-carboxylate

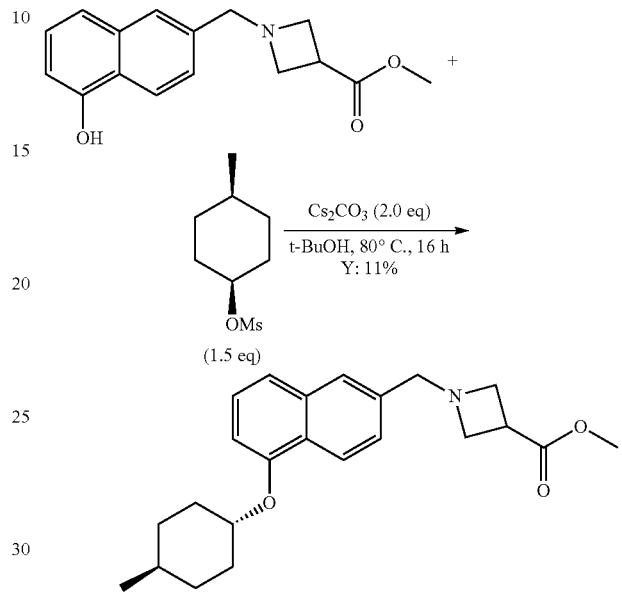

Methyl 1-((5-(((trans-4-methylcyclohexyl)oxy)naphthalen-2-yl)methyl)azetidine-3-carboxylate was obtained following the same procedure as ethyl 1-((5-(((trans-4-(trifluoromethyl)cyclohexyl)oxy)naphthalen-2-yl)methyl)piperidine-4-carboxylate as a yellow oil (15 mg, Y: 11%). ESI-MS (M+H)⁺: 368.3.

Step 3: 1-((5-(((trans-4-methylcyclohexyl)oxy)naphthalen-2-yl)methyl)azetidine-3-carboxylic acid

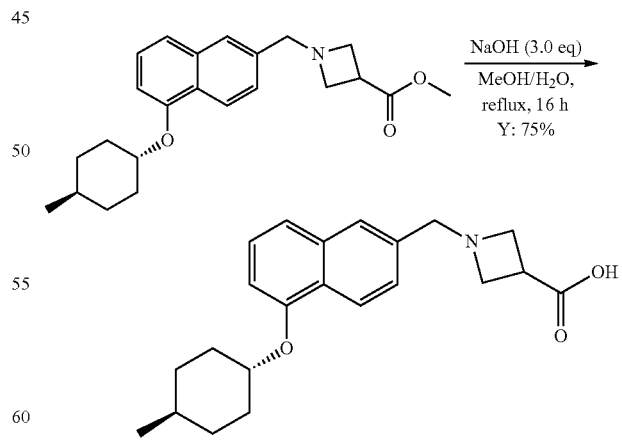

1-((5-(((trans-4-methylcyclohexyl)oxy)naphthalen-2-yl)methyl)azetidine-3-carboxylic acid was obtained following the same procedure as 3-(((5-(((trans-4-(tert-butyl)cyclohexyl)oxy)naphthalen-2-yl)methyl)amino)-2,2-dimethylcyclobutanecarboxylic acid as a yellow oil (10 mg, Y: 75%).

¹H NMR (400 MHz, CD₃OD) δ: 8.25 (d, J=8.8 Hz, 1H), 7.85 (s, 1H), 7.46-7.42 (m, 3H), 7.01-6.99 (m, 1H), 4.47-4.40 (m, 1H), 4.29 (s, 2H), 4.01-4.00 (m, 4H), 3.38-3.34 (m, 1H), 2.25-2.23 (m, 2H), 1.86-1.83 (m, 2H), 1.62-1.47 (m, 3H), 1.23-1.13 (m, 2H), 0.97 (d, J=6.4 Hz, 3H); ESI-MS (M+H)⁺: 354.2.

Example 18: 1-((5-((trans-4-phenylcyclohexyl)oxy)naphthalen-2-yl)methyl)azetidine-3-carboxylic acid Step 1: methyl 1-((5-((trans-4-phenylcyclohexyl)oxy)naphthalen-2-yl)methyl)azetidine-3-carboxylate

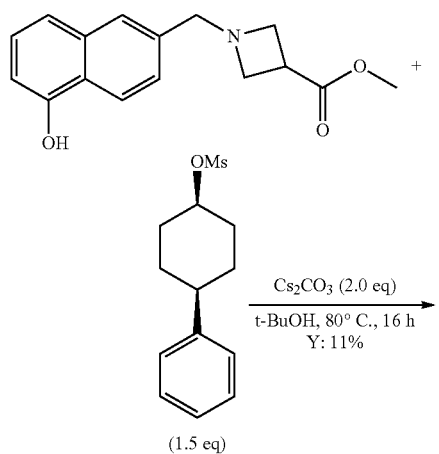

Methyl 1-((5-((trans-4-phenylcyclohexyl)oxy)naphthalen-2-yl)methyl)azetidine-3-carboxylate was obtained following the same procedure as ethyl 1-((5-((trans-4-(trifluoromethyl)cyclohexyl)oxy)naphthalen-2-yl)methyl)piperidine-4-carboxylate as a white solid (15 mg, Y: 11%). ESI-MS (M+H)⁺: 430.2.

Step 2: 1-((5-((trans-4-phenylcyclohexyl)oxy)naphthalen-2-yl)methyl)azetidine-3-carboxylic acid

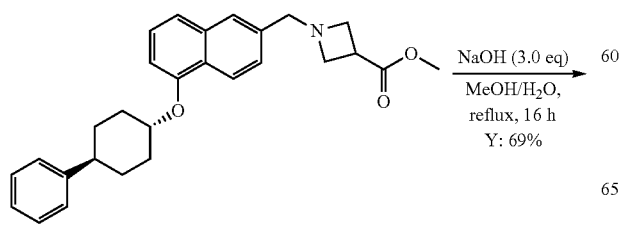

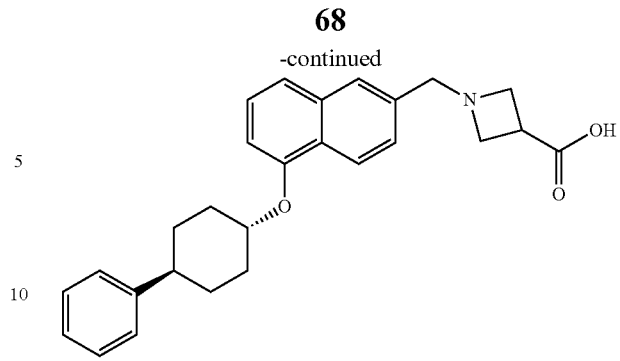

1-((5-((trans-4-phenylcyclohexyl)oxy)naphthalen-2-yl)methyl)azetidine-3-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a white solid (10 mg, Y: 69%).

¹H NMR (400 MHz, CD₃OD) δ: 8.30 (d, J=9.2 Hz, 1H), 7.88 (s, 1H), 7.48-7.45 (m, 3H), 7.31-7.27 (m, 4H), 7.20-7.17 (m, 1H), 7.10-7.07 (m, 1H), 4.61-4.59 (m, 1H), 4.36 (s, 2H), 4.09-4.04 (m, 4H), 3.43-3.36 (m, 1H), 2.70-2.63 (m, 1H), 2.41-2.40 (m, 2H), 2.03-2.00 (m, 2H), 1.78-1.69 (m, 4H); ESI-MS (M+H)⁺: 416.2.

Example 19: 1-((5-((trans-4-ethylcyclohexyl)oxy)naphthalen-2-yl)methyl)azetidine-3-carboxylic acid Step 1: methyl 1-((5-((trans-4-ethylcyclohexyl)oxy)naphthalen-2-yl)methyl)azetidine-3-carboxylate

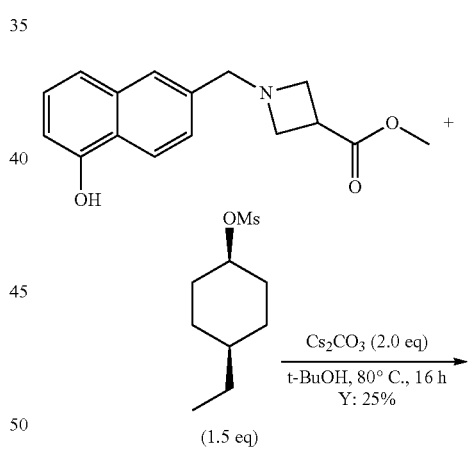

Methyl 1-((5-((trans-4-ethylcyclohexyl)oxy)naphthalen-2-yl)methyl)azetidine-3-carboxylate was obtained following the same procedure as ethyl 1-((5-((trans-4-(trifluoromethyl)cyclohexyl)oxy)naphthalen-2-yl)methyl)piperidine-4-carboxylate as a white solid (50 mg, Y: 25%). ESI-MS (M+H)⁺: 382.1.

Step 2: 1-((5-((trans-4-ethylcyclohexyl)oxy)naph-
thalen-2-yl)methyl)azetidine-3-carboxylic acid

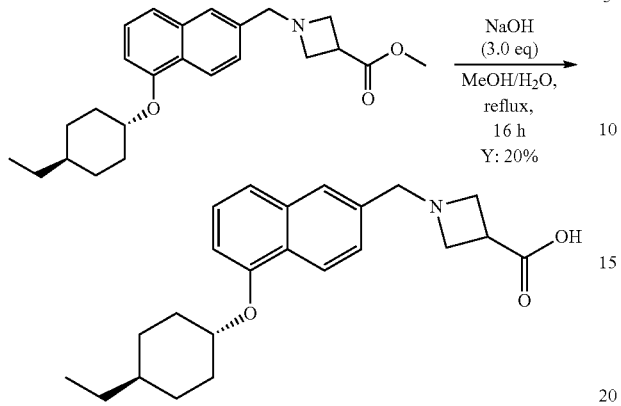

1-((5-((trans-4-ethylcyclohexyl)oxy)naphthalen-2-yl)
methyl)azetidine-3-carboxylic acid was obtained following
the same procedure as 3-(((5-((trans-4-(tert-butyl)cyclo-
hexyl)oxy)naphthalen-2-yl)methyl)amino)-2,2-dimethylcy-
clobutanecarboxylic acid as a white solid (10 mg, Y: 20%).
$^1$H NMR (400 MHz, CD$_3$OD) δ: 8.26 (d, J=8.8 Hz, 1H),
7.85 (s, 1H), 7.45-7.40 (m, 3H), 7.02-6.97 (m, 1H), 4.47-
4.40 (m, 1H), 4.31 (s, 2H), 4.07-3.98 (m, 4H), 3.41-3.35 (m,
1H), 2.28-2.25 (m, 2H), 1.93-1.90 (m, 2H), 1.60-1.50 (m,
2H), 1.35-1.09 (m, 5H), 0.95 (t, J=7.2 Hz, 3H); ESI-MS
(M+H)$^+$: 368.3.

Example 20: 1-((5-((trans-4-(trifluoromethyl)cyclo-
hexyl)oxy)naphthalen-2-yl)methyl)azetidine-3-car-
boxylic acid Step 1: methyl 1-((5-((trans-4-(trifluoromethyl)cy-
clohexyl)oxy)naphthalen-2-yl)methyl)azetidine-3-
carboxylate

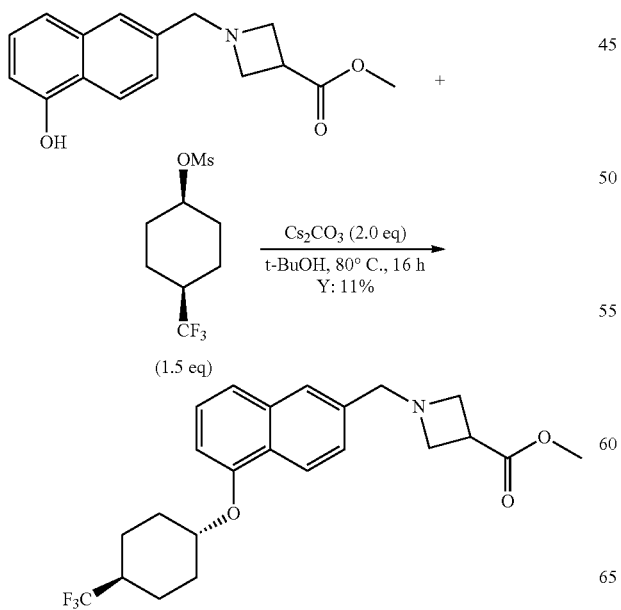

Methyl 1-((5-((trans-4-(trifluoromethyl)cyclohexyl)oxy)
naphthalen-2-yl)methyl)azetidine-3-carboxylate was
obtained following the same procedure as ethyl 1-((5-
((trans-4-(trifluoromethyl)cyclohexyl)oxy)naphthalen-2-yl)
methyl)piperidine-4-carboxylate as a white solid (15 mg, Y:
11%). ESI-MS (M+H)$^+$: 422.2.

Step 2: 1-((5-((trans-4-(trifluoromethyl)cyclohexyl)
oxy)naphthalen-2-yl)methyl)azetidine-3-carboxylic
acid

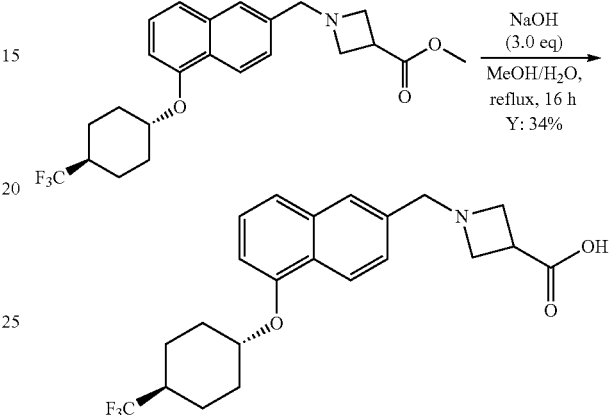

1-((5-((trans-4-(trifluoromethyl)cyclohexyl)oxy)naphtha-
len-2-yl)methyl)azetidine-3-carboxylic acid was obtained
following the same procedure as 3-(((5-((trans-4-(tert-butyl)
cyclohexyl)oxy)naphthalen-2-yl)methyl)amino)-2,2-dim-
ethylcyclobutanecarboxylic acid as a white solid (5 mg, Y:
34%).
$^1$H NMR (400 MHz, CD$_3$OD) δ: 8.16 (d, J=8.8 Hz, 1H),
7.72 (s, 1H), 7.41-7.35 (m, 3H), 6.97 (dd, J=1.6 Hz, 8.8 Hz,
1H), 4.48-4.43 (m, 1H), 3.89 (s, 2H), 3.66 (t, J=8.0 Hz, 2H),
3.55 (t, J=8.0 Hz, 2H), 3.26-3.22 (m, 1H), 2.38-2.23 (m,
3H), 2.07-2.04 (m, 2H), 1.65-1.50 (m, 4H); ESI-MS
(M+H)$^+$: 408.1.

Example 21: 1-((5-((trans-4-isopropylcyclohexyl)
oxy)naphthalen-2-yl)methyl)azetidine-3-carboxylic
acid Step 1: methyl 1-((5-((trans-4-isopropylcyclohexyl)
oxy)naphthalen-2-yl)methyl)azetidine-3-carboxylate

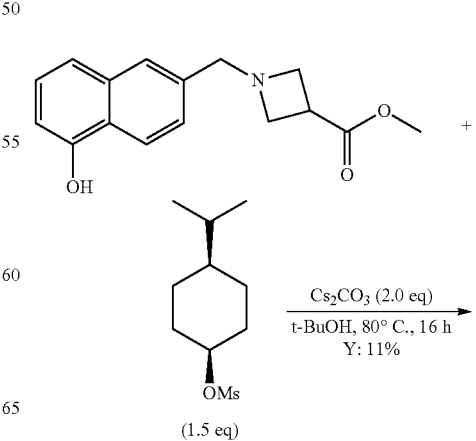

71

-continued

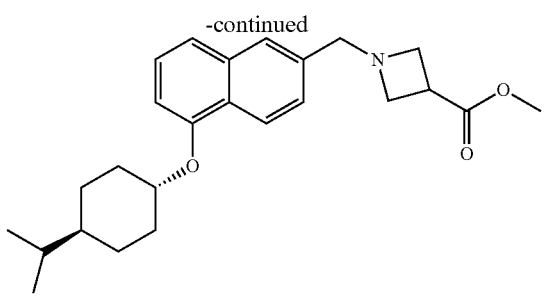

Methyl 1-((5-(((trans-4-isopropylcyclohexyl)oxy)naphthalen-2-yl)methyl)azetidine-3-carboxylate was obtained following the same procedure as ethyl 1-((5-(((trans-4-(trifluoromethyl)cyclohexyl)oxy)naphthalen-2-yl)methyl)piperidine-4-carboxylate as a white solid (13 mg, Y: 11%). ESI-MS (M+H)+: 396.3.

Step 2: 1-((5-(((trans-4-isopropylcyclohexyl)oxy)naphthalen-2-yl)methyl)azetidine-3-carboxylic acid

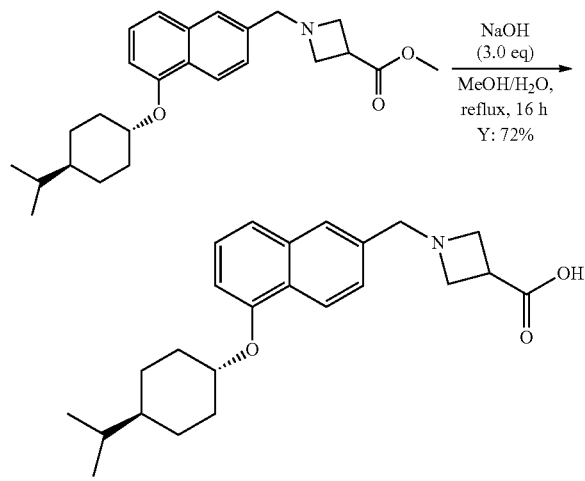

1-((5-(((trans-4-isopropylcyclohexyl)oxy)naphthalen-2-yl)methyl)azetidine-3-carboxylic acid was obtained following the same procedure as 3-(((5-(((trans-4-(tert-butyl)cyclohexyl)oxy)naphthalen-2-yl)methyl)amino)-2,2-dimethylcyclobutanecarboxylic acid as a white solid (9 mg, Y: 72%).

72

$^1$H NMR (400 MHz, CD$_3$OD) δ: 8.14 (d, J=8.8 Hz, 1H), 7.68 (s, 1H), 7.37-7.34 (m, 3H), 6.90 (dd, J=2.0 Hz, 6.4 Hz, 1H), 4.40-4.34 (m, 1H), 3.76 (s, 2H), 3.55 (t, J=8.0 Hz, 2H), 3.38 (t, J=8.0 Hz, 2H), 3.26-3.21 (m, 1H), 2.29-2.27 (m, 2H), 1.89-1.85 (m, 2H), 1.56-1.47 (m, 3H), 128-1.15 (m, 3H), 0.92 (d, J=6.8 Hz, 6H); ESI-MS (M+H)+: 382.3.

Example 22: 1-((5-(((trans-4-butylcyclohexyl)oxy)naphthalen-2-yl)methyl)azetidine-3-carboxylic acid Step 1: methyl 1-((5-(((trans-4-butylcyclohexyl)oxy)naphthalen-2-yl)methyl)azetidine-3-carboxylate

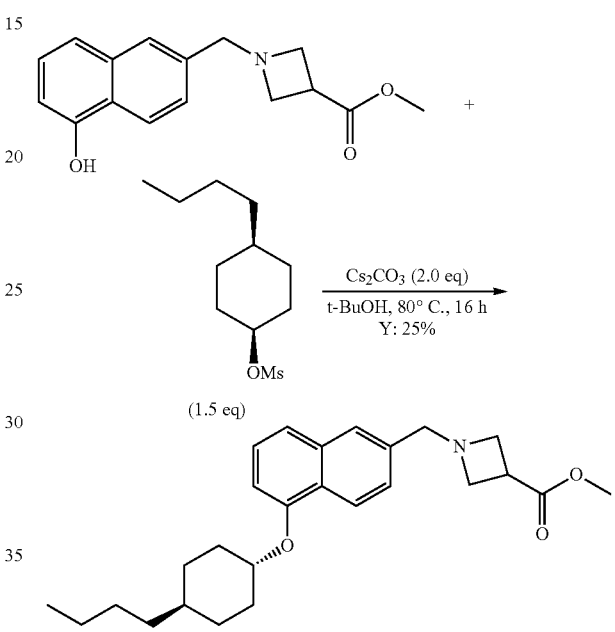

Methyl 1-((5-(((trans-4-butylcyclohexyl)oxy)naphthalen-2-yl)methyl)azetidine-3-carboxylate was obtained following the same procedure as ethyl 1-((5-(((trans-4-(trifluoromethyl)cyclohexyl)oxy)naphthalen-2-yl)methyl)piperidine-4-carboxylate as a yellow oil (30 mg, Y: 25%). ESI-MS (M+H)+: 410.2.

Step 2: 1-((5-(((trans-4-butylcyclohexyl)oxy)naphthalen-2-yl)methyl)azetidine-3-carboxylic acid

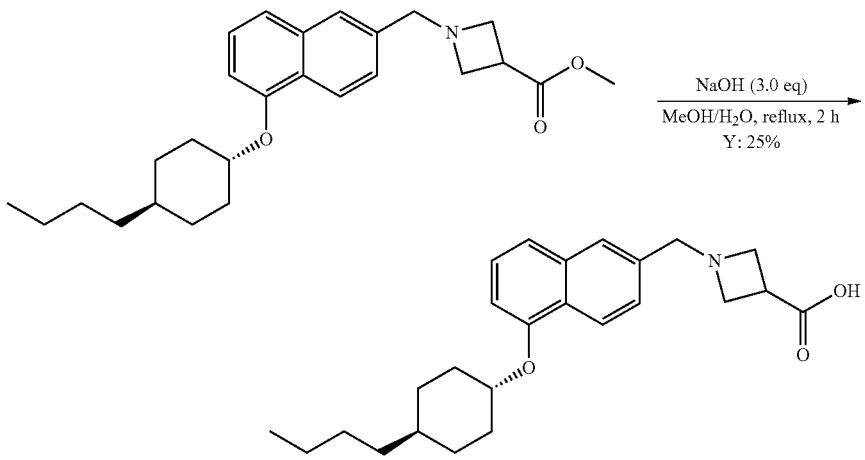

1-((5-((trans-4-butylcyclohexyl)oxy)naphthalen-2-yl)methyl)azetidine-3-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow oil (5 mg, Y: 25%).

$^1$H NMR (400 MHz, CD$_3$OD) δ: 8.04 (d, J=9.2 Hz, 1H), 7.58 (s, 1H), 7.28-7.22 (m, 3H), 6.80 (dd, J=2.0 Hz, 6.8 Hz, 1H), 4.34-4.26 (m, 1H), 3.66 (s, 2H), 3.47-3.43 (m, 2H), 3.30-3.25 (m, 4H), 3.16-3.07 (m, 1H), 2.18-2.14 (m, 2H), 1.81-1.78 (m, 2H), 1.49-1.39 (m, 2H), 1.27-1.22 (m, 5H), 1.08-0.98 (m, 2H), 0.83 (t, J=7.2 Hz, 3H); ESI-MS (M+H)$^+$: 396.3.

Example 23: 1-((5-(((trans-4-cyclopentylcyclohexyl)oxy)naphthalen-2-yl)methyl)azetidine-3-carboxylic acid Step 1: methyl 1-((5-((trans-4-cyclopentylcyclohexyl)oxy)naphthalen-2-yl)methyl)azetidine-3-carboxylate

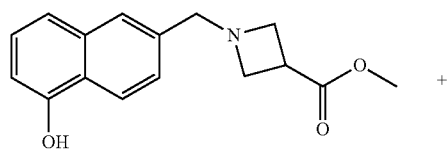

+

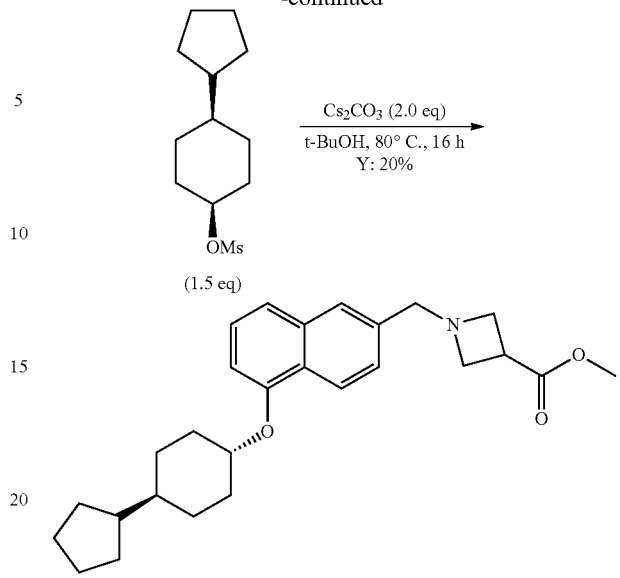

Methyl 1-((5-((trans-4-cyclopentylcyclohexyl)oxy)naphthalen-2-yl)methyl)azetidine-3-carboxylate was obtained following the same procedure as ethyl 1-((5-((trans-4-(trifluoromethyl)cyclohexyl)oxy)naphthalen-2-yl)methyl)piperidine-4-carboxylate as a yellow oil (25 mg, Y: 20%). ESI-MS (M+H)$^+$: 422.1.

Step 2: 1-((5-(((trans-4-cyclopentylcyclohexyl)oxy)naphthalen-2-yl)methyl)azetidine-3-carboxylic acid

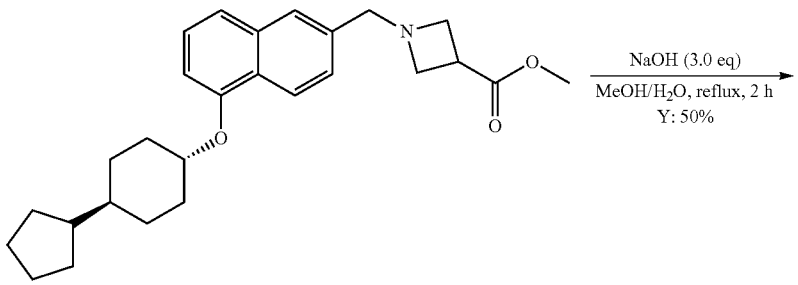

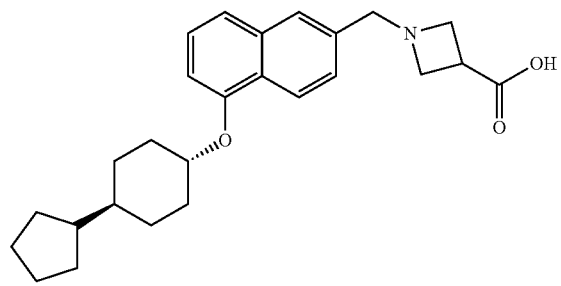

1-((5-(((trans-4-cyclopentylcyclohexyl)oxy)naphthalen-2-yl)methyl)azetidine-3-carboxylic acid was obtained following the same procedure as 3-(((5-((trans-4-(tert-butyl)cyclohexyl)oxy)naphthalen-2-yl)methyl)amino)-2,2-dimethylcyclobutanecarboxylic acid as a yellow oil (10 mg, Y: 50%).

$^1$H NMR (400 MHz, CD$_3$OD) δ: 8.04 (d, J=8.4 Hz, 1H), 7.57 (s, 1H), 7.27-7.22 (m, 3H), 6.80 (dd, J=1.6 Hz, 6.4 Hz, 1H), 4.32-4.25 (m, 1H), 3.66 (s, 2H), 3.47-3.43 (m, 2H), 3.28-3.26 (m, 2H), 3.15-3.07 (m, 1H), 2.16-2.13 (m, 2H), 1.85-1.83 (m, 2H), 1.74-1.67 (m, 2H), 1.55-1.37 (m, 8H), 1.09-1.04 (m, 4H); ESI-MS (M+H)$^+$: 408.3.

Example 24: 1-((5-((trans-4-(tert-butyl)cyclohexyl)oxy)naphthalen-2-yl)methyl)piperidine-4-carboxylic acid

Step 1: ethyl 1-((5-((trans-4-(tert-butyl)cyclohexyl)oxy)naphthalen-2-yl)methyl)piperidine-4-carboxylate

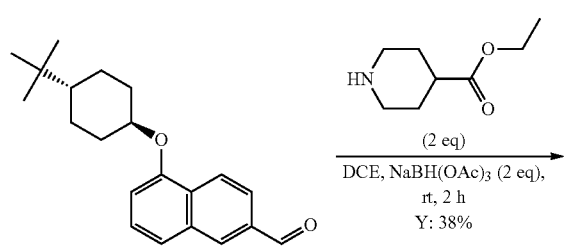

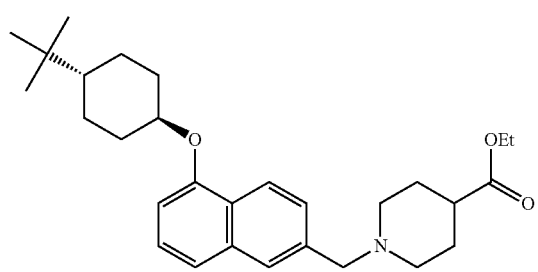

A mixture of 5-((trans-4-(tert-butyl)cyclohexyl)oxy)-2-naphthaldehyde (145 mg, 0.47 mmol), ethyl piperidine-4-carboxylate (147 mg, 0.94 mmol, 2 eq) and NaBH(OAc)$_3$ (198 mg, 0.94 mol, 2 eq) in DCE (10 mL) was stirred at rt for 2 h. Water (100 mL) was added to the mixture. The organic layer was washed with brine (100 mL), dried over Na$_2$SO$_4$ and concentrated to give ethyl 1-((5-((trans-4-(tert-butyl)cyclohexyl)oxy)naphthalen-2-yl)methyl)piperidine-4-carboxylate as a white solid (80 mg, Y: 38%). ESI-MS (M+H)$^+$: 452.3

$^1$H NMR (400 MHz, CDCl$_3$) δ: 8.20 (d, J=8.8 Hz, 1H), 7.66 (s, 1H), 7.44 (dd, J=8.8, 1.2 Hz, 1H), 7.37-7.31 (m, 2H), 6.83 (dd, J=6.8, 1.6 Hz, 1H), 4.31-4.27 (m, 1H), 4.18 (q, J=7.2 Hz, 2H), 3.64 (s, 2H), 2.90-2.88 (m, 2H), 2.33-2.25 (m, 3H), 2.09-2.04 (m, 2H), 1.90-1.87 (m, 5H), 1.28-1.08 (m, 9H), 0.89 (s, 9H).

Step 2: 1-((5-(((trans-4-(tert-butyl)cyclohexyl)oxy)naphthalen-2-yl)methyl)piperidine-4-carboxylic acid

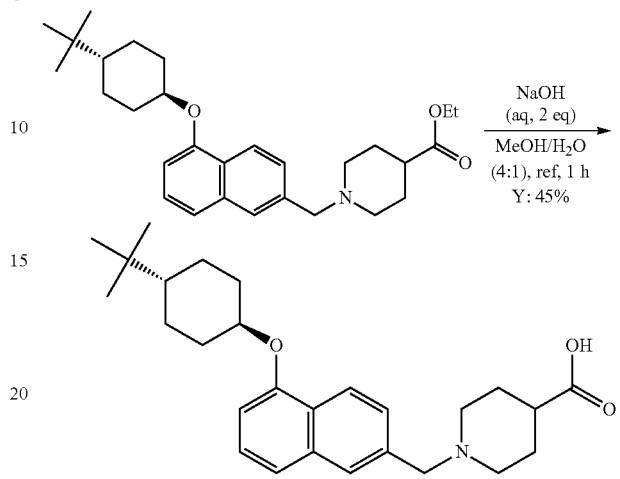

To a solution of ethyl 1-((5-((trans-4-(tert-butyl)cyclohexyl)oxy)naphthalen-2-yl)methyl)piperidine-4-carboxylate (80 mg, 0.18 mmol, 1.0 eq) in MeOH/H$_2$O (4:1, 10 mL) was added NaOH (14 mg, 0.35 mmol, 2.0 eq). The mixture was stirred at reflux for 1 h. After cooling down to rt, the mixture was concentrated and the residue was adjusted to pH=6 with 1 N HCl. The solid was collected by filtration and washed with water. After dried under vacuum, 1-((5-((trans-4-(tert-butyl)cyclohexyl)oxy)naphthalen-2-yl)methyl)piperidine-4-carboxylic acid was obtained as a light yellow solid (34 mg, Y: 45%). ESI-MS (M+H)$^+$: 424.3, HPLC: 100.00%-100.00%.

$^1$H NMR (400 MHz, CDCl$_3$) δ: 8.20 (d, J=8.0 Hz, 1H), 7.82 (s, 1H), 7.40 (dd, J=9.2, 1.6 Hz, 1H), 7.36-7.35 (m, 2H), 6.94 (q, J=4.4 Hz, 1H), 4.36-4.29 (m, 1H), 4.23 (s, 2H), 3.30-3.27 (m, 2H), 2.89-2.87 (m, 2H), 2.35-2.30 (m, 1H), 2.24-2.22 (m, 2H), 1.99-1.96 (m, 2H), 1.86-1.83 (m, 4H), 1.47-1.39 (m, 2H), 1.17-1.04 (m, 3H), 0.90 (s, 9H).

Example 25: 1-((5-(heptyloxy)naphthalen-2-yl)methyl)piperidine-4-carboxylic acid

Step 1: 6-bromonaphthalen-1-ol

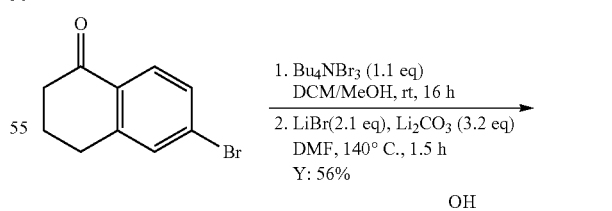

A solution of tetrabutylammonium tribromide (832 mg, 1.1 eq, 1.73 mmol) in DCM (4 mL) was added dropwise to a solution of 6-bromo-3,4-dihydronaphthalen-1(2H)-one (350 mg, 1.0 eq, 1.57 mmol) in dichloromethane (2 mL) and methanol (2 mL) at room temperature over 1 h. At completion of the addition, the mixture was stirred at rt for 15 hrs and was then concentrated. The residue was taken into DCM and was washed with saturated sodium bicarbonate three times. The organic layer was concentrated and the residue was dissolved in dimethylformamide (10 mL). Lithium carbonate (286 mg, 2.1 eq, 3.29 mmol) and lithium bromide (372 mg, 3.2 eq, 5.02 mmol) were added and the resulting mixture was stirred at 140° C. for 1.5 hrs. After cooling to rt, the solids were filtered and rinsed with ethyl acetate. The filtrate was washed with water four times and dried over sodium sulfate to give 6-bromonaphthalen-1-ol as a brown solid (195 mg, Y: 56%).

$^1$H NMR (400 MHz, CDCl$_3$) δ: 8.06 (d, J=9.2 Hz, 1H), 7.97 (d, J=2.4 Hz, 1H), 7.54 (dd, J=8.8 Hz, 2.0 Hz, 1H), 7.35-7.29 (m, 2H), 6.80 (dd, J=6.0 Hz, 1.6 Hz, 1H), 5.20 (s, 1H).

Step 2: 6-bromo-1-(heptyloxy)naphthalene

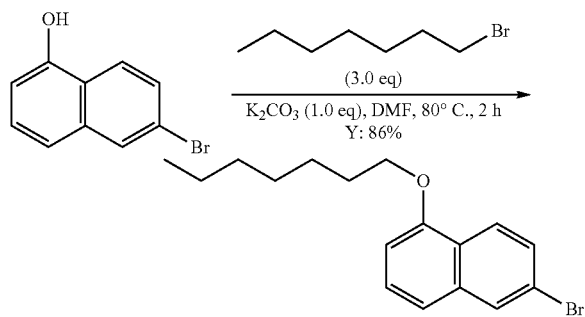

To a solution of 6-bromonaphthalen-1-ol (156 mg, 0.7 mmol, 1.0 eq) in DMF (5 mL) were added 1-bromoheptane (370 mg, 2.1 mmol, 3.0 eq) and K$_2$CO$_3$ (97 mg, 0.7 mmol, 1.0 eq). The mixture was stirred at 80° C. for 2 h. After cooling down to rt, the mixture was diluted with brine (50 mL) and extracted with EtOAc (60 mL×3). The combined organic phase was dried over Na$_2$SO$_4$ and concentrated under reduced pressure. The residue was purified by silica gel plate (EA:PE=1:10) to give 6-bromo-1-(heptyloxy)naphthalene as brown oil (180 mg, Y: 86%). ESI-MS (M+H)$^+$: 321.1.

$^1$H NMR (400 MHz, CDCl$_3$) δ: 8.14 (d, J=9.2 Hz, 1H), 7.93 (d, J=2.0 Hz, 1H), 7.51 (dd, J=8.8 Hz, 2.0 Hz, 1H), 7.37 (t, J=8.4 Hz, 1H), 7.30-7.28 (m, 1H), 6.79 (d, J=7.6 Hz, 1H), 4.11 (t, J=6.4 Hz, 2H), 1.95-1.88 (m, 2H), 1.58-1.51 (m, 2H), 1.44-1.34 (m, 6H), 0.92-0.89 (m, 3H).

Step 3: 5-(heptyloxy)-2-naphthaldehyde

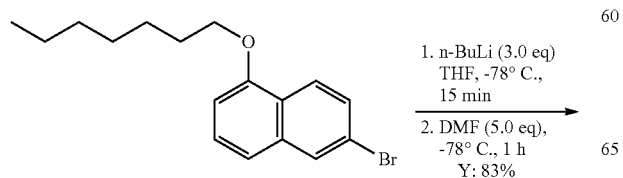

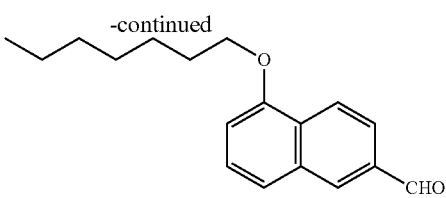

5-(heptyloxy)-2-naphthaldehyde was prepared following the same procedure as 5-((trans-4-(tert-butyl)cyclohexyl)oxy)-2-naphthaldehyde, as yellow oil, 130 mg, Y: 83%. ESI-MS (M+H)$^+$: 271.2.

$^1$H NMR (400 MHz, CDCl$_3$) δ: 10.16 (s, 1H), 8.39 (d, J=8.4 Hz, 1H), 8.28 (s, 1H), 7.92 (dd, J=9.2 Hz, 1.6 Hz, 1H), 7.57-7.55 (m, 1H), 7.47 (t, J=7.6 Hz, 1H), 6.95 (d, J=7.6 Hz, 1H), 4.15 (t, J=6.8 Hz, 2H), 1.97-1.90 (m, 2H), 1.60-1.53 (m, 2H), 1.45-1.38 (m, 2H), 1.35-1.32 (m, 4H), 0.90 (t, J=6.8 Hz, 3H).

Step 4: ethyl 1-((5-(heptyloxy)naphthalen-2-yl)methyl)piperidine-4-carboxylate

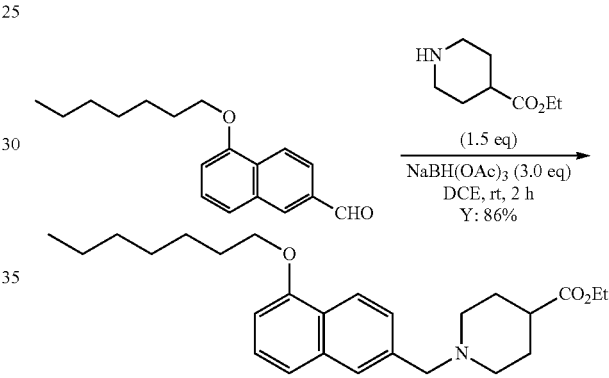

Ethyl 1-((5-(heptyloxy)naphthalen-2-yl)methyl)piperidine-4-carboxylate was prepared following the same procedure as ethyl 1-((5-((trans-4-(tert-butyl)cyclohexyl)oxy)naphthalen-2-yl)methyl)piperidine-4-carboxylate, as yellow oil, 170 mg, Y: 86%. ESI-MS (M+H)$^+$: 412.3.

$^1$H NMR (400 MHz, CDCl$_3$) δ: 8.22 (d, J=8.4 Hz, 1H), 7.68 (s, 1H), 7.46 (d, J=8.8 Hz, 1H), 7.37-7.32 (m, 2H), 6.77 (dd, J=6.8 Hz, 2.0 Hz, 1H), 4.15-4.09 (m, 4H), 3.65 (s, 2H), 2.91-2.88 (m, 2H), 2.34-2.26 (m, 1H), 2.10-2.06 (m, 2H), 1.93-1.80 (m, 6H), 1.59-1.52 (m, 2H), 1.44-1.39 (m, 2H), 1.34-1.31 (m, 4H), 1.24 (t, J=7.2 Hz, 3H), 0.90 (t, J=6.8 Hz, 3H).

Step 5: 1-((5-(heptyloxy)naphthalen-2-yl)methyl)piperidine-4-carboxylic acid

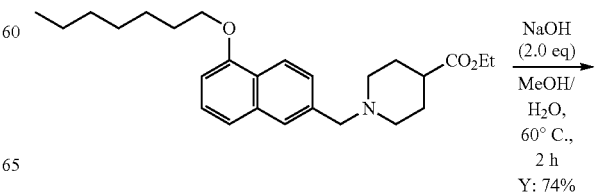

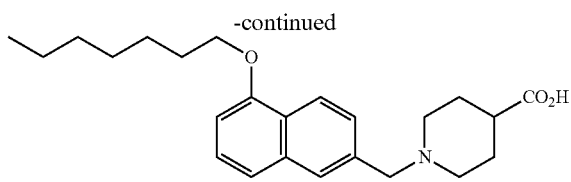

1-((5-(heptyloxy)naphthalen-2-yl)methyl)piperidine-4-carboxylic acid was prepared following the same procedure as 1-((5-(((trans-4-(tert-butyl)cyclohexyl)oxy)naphthalen-2-yl)methyl)piperidine-4-carboxylic acid, as yellow oil, 55 mg, Y: 74%. ESI-MS (M+H)+: 384.3. HPLC: 100.00%-100.00%.

¹H NMR (400 MHz, MeOD) δ: 8.30 (d, J=8.8 Hz, 1H), 7.89 (s, 1H), 7.50 (d, J=8.8 Hz, 1H), 7.44-7.43 (m, 2H), 6.92-6.91 (m, 1H), 4.26 (s, 2H), 4.15 (t, J=6.4 Hz, 2H), 3.35-3.34 (m, 2H), 2.92-2.85 (m, 2H), 2.40-2.35 (m, 1H), 2.06-2.01 (m, 2H), 1.95-1.89 (m, 4H), 1.61-1.54 (m, 2H), 1.46-1.41 (m, 2H), 1.36-1.34 (m, 4H), 0.91 (t, J=6.8 Hz, 3H).

Example 26: 9-((5-((cis-4-methylcyclohexyl)oxy)naphthalen-2-yl)methyl)-9-azabicyclo[3.3.1]nonane-3-carboxylic acid Step 1: (5-((cis-4-methylcyclohexyl)oxy)naphthalen-2-yl)methanol

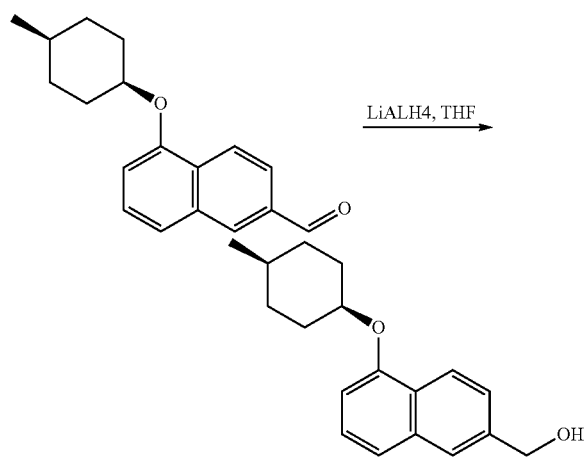

To a mixture of 5-(4-methyl-cyclohexyloxy)-naphthalene-2-carbaldehyde (400 mg, 1 mmol) in tetrahydrofuran (7.254 mL, 89.44 mmol) was added 1.00M of lithium tetrahydroaluminate in tetrahydrofuran (3.726 mL, 3.726 mmol). Gas evolution observed. The reaction was then stirred at rt for 30 min, LCMS showed complete conversion. EtOAc was added and rochele's salt was added and stirred for 30 min. The organic layer was washed with brine, dried and evaporated, and dried under high vacuum to give (5-((cis-4-methylcyclohexyl)oxy)naphthalen-2-yl)methanol (0.4 g). LCMS: RT 1.92 min; M m/z=271.10 M+1. It was used to next step as is.

Step 2: (5-((cis-4-methylcyclohexyl)oxy)naphthalen-2-yl)methyl methanesulfonate

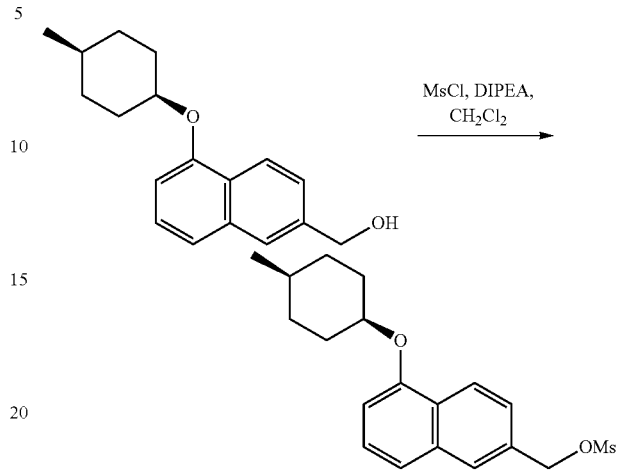

To a solution of [5-(4-methyl-cyclohexyloxy)-naphthalen-2-yl]-methanol (413 mg, 1.53 mmol) and N,N-diisopropylethylamine (0.79822 mL, 4.5827 mmol) in methylene chloride (7.1 mL, 110 mmol) was added methanesulfonyl chloride (0.23647 mL, 3.0551 mmol) dropwise. A white precipitate formed. The solution was stirred at rt for 5 h. LCMS showed no starting material left, and complete conversion to RT 2.39 min m/z=289.00. The mixture was diluted with DCM and washed with sodium bicarbonate aq solution and water, dried over MgSO₄, filtered, concentrated. The residue was used as in the next step.

Step 3: 9-((5-((cis-4-methylcyclohexyl)oxy)naphthalen-2-yl)methyl)-9-azabicyclo[3.3.1]nonane-3-carboxylic acid

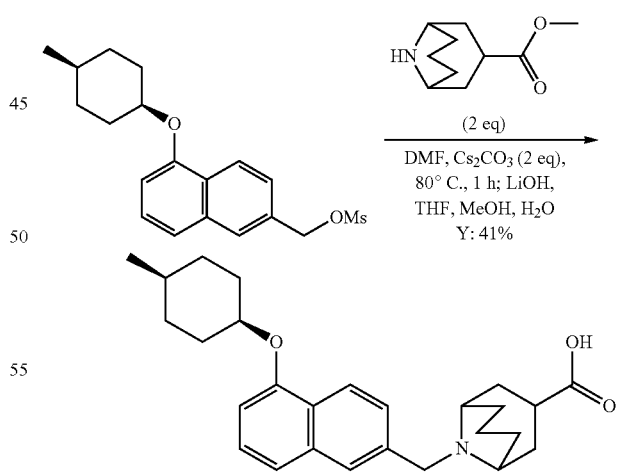

To a solution of methanesulfonic acid 5-(4-methyl-cyclohexyloxy)-naphthalen-2-ylmethyl ester (177 mg, 0.508 mmol) in DMF (1.9665 mL, 25.398 mmol), 9-aza-bicyclo[3.3.1]nonane-3-carboxylic acid methyl ester HCl salt (223.20 mg, 1.0159 mmol) was added, followed by cesium carbonate (496.50 mg, 1.5238 mmol). The reaction was then heated at 80° C. for 1 h. LCMS showed no SM left, and the completion of the reaction. After cooled down, the reaction mixture was diluted with EtOAc, washed with water (2×). The organic phase was then separated, dried and concentrated. The crude was purified by HPLC, removed the solvent, the ester was then dissolved in tetrahydrofuran (2.4 mL, 29 mmol), treated with 1.0 M of lithium hydroxide in water (3.5 mL, 3.5 mmol) at rt overnight. Acidified with 1NHCl, the organic layer was dried and concentrated. The crude was then purified by HLPC to give 9-((5-((cis-4-methylcyclohexyl)oxy)naphthalen-2-yl)methyl)-9-azabicyclo[3.3.1]nonane-3-carboxylic acid as a white powder (86.9 mg, 41%). LCMS: RT=1.43 min.; MH+ 422.10.

¹H NMR (400 MHz, METHANOL-d4) δ 8.42 (d, J=8.72 Hz, 1H), 8.07 (d, J=4.77 Hz, 1H), 7.65 (d, J=8.60 Hz, 1H), 7.49 (d, J=5.46 Hz, 2H), 6.95-7.10 (m, 1H), 4.61-4.81 (m, 2H), 3.40-3.79 (m, 2H), 1.35-2.75 (m, 20H), 1.00 (d, J=5.84 Hz, 3H).

Example 27: 8-((5-((cis-4-methylcyclohexyl)oxy)naphthalen-2-yl)methyl)-8-azabicyclo[3.2.1]octane-3-carboxylic acid

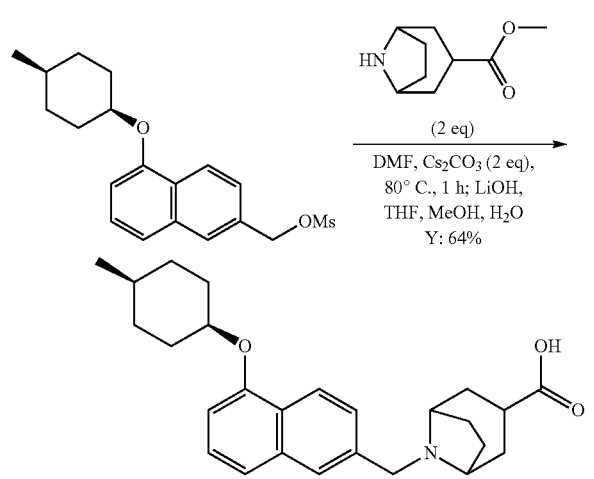

To a solution of methanesulfonic acid 5-(4-methyl-cyclohexyloxy)-naphthalen-2-ylmethyl ester (177 mg, 0.508 mmol) in DMF (2 mL), 8-aza-bicyclo[3.2.1]octane-3-carboxylic acid methyl ester HCl salt (208.38 mg, 1.0131 mmol) was added, followed by cesium carbonate (495.14 mg, 1.5197 mmol). The reaction was then heated at 80° C. for 1 h. After cooled down, the reaction mixture was diluted with EtOAc, washed with water (2×). The organic phase was then separated, dried and concentrated. The crude was purified by HPLC, removed the solvent, the ester was then dissolved in tetrahydrofuran (2.3 mL, 29 mmol), treated with 1.0 M of lithium hydroxide in Water (3.5 mL, 3.5 mmol) at rt overnight. Acidified with 1NHCl, the organic layer was dried and concentrated. The crude was then purified by HLPC to give 8-((5-((cis-4-methylcyclohexyl)oxy)naphthalen-2-yl)methyl)-8-azabicyclo[3.2.1]octane-3-carboxylic acid as a white powder (132.9 mg, 64%). LCMS: RT 1.40 min.; MH+ 408.1.

¹H NMR (400 MHz, METHANOL-d4) δ 8.38 (d, J=8.72 Hz, 1H), 7.98 (s, 1H), 7.60 (d, J=10.48 Hz, 1H), 7.46 (d, J=4.96 Hz, 2H), 6.92-7.08 (m, 1H), 4.85 (br. s., 1H), 3.80-4.45 (m, 2H), 3.37 (s, 2H), 1.35-2.81 (m, 18H), 1.00 (d, J=5.65 Hz, 3H).

Example 28: 1-((5-((cis-4-methylcyclohexyl)oxy)naphthalen-2-yl)methyl)piperidine-4-carboxylic acid

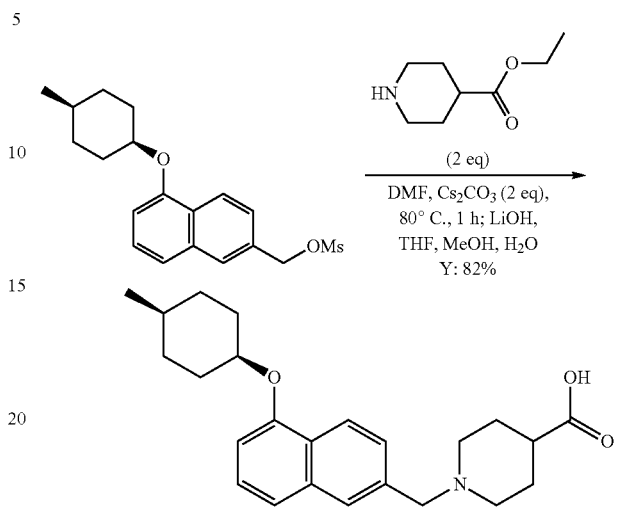

To a solution of methanesulfonic acid 5-(cis-4-methyl-cyclohexyloxy)-naphthalen-2-ylmethyl ester (177 mg, 0.508 mmol) in DMF (2 mL), ethyl piperidine-4-carboxylate (159.71 mg, 1.0159 mmol) was added, followed by cesium carbonate (496.50 mg, 1.5238 mmol).

The reaction was then heated at 80° C. for 1 h. After cooled down, the reaction mixture was diluted with EtOAc, washed with water (2×). The organic phase was then separated, dried and concentrated. The crude was purified by HPLC, removed the solvent, the ester was then dissolved in THF (2.4 mL, 29 mmol), treated with 1.0 M of lithium hydroxide in water (3.5 mL, 3.5 mmol) at rt overnight. Acidified with 1NHCl, the organic layer was dried and concentrated. The crude was then purified by HLPC to give 1-((5-((cis-4-methylcyclohexyl)oxy)naphthalen-2-yl)methyl)piperidine-4-carboxylic acid as a white powder (160 mg, 82%). LCMS: RT 1.46 min.; MH+ 382.10.

¹H NMR (400 MHz, METHANOL-d4) δ 8.41 (d, J=8.66 Hz, 1H), 7.98 (s, 1H), 7.56 (d, J=10.42 Hz, 1H), 7.49 (s, 2H), 6.92-7.10 (m, 1H), 4.83-4.85 (m, OH), 4.49 (s, 2H), 3.61 (d, J=12.61 Hz, 2H), 2.98-3.19 (m, 2H), 1.38-2.75 (m, 14H), 1.00 (d, J=5.84 Hz, 3H).

Example 29: 1-((5-(heptyloxy)naphthalen-1-yl)methyl)piperidine-4-carboxylic acid Step 1: of 5-iodonaphthalen-1-ol

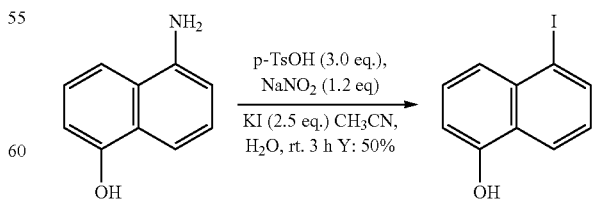

To a solution of 5-aminonaphthalen-1-ol (1.59 g, 10 mmol, 1.0 eq) in CH₃CN (100 mL) were added p-TsOH.H₂O (5.7 g, 30 mmol, 3.0 eq) and a solution of NaNO₂ (1.87 g, 27.5 mmol, 1.1 eq) in 10 mL water at 0° C.

After stirring at 0° C. for 1 h, KI (25 mmol, 4.15 g, 2.5 eq) was added and the mixture was stirred at rt for another 3 h. After diluted with EtOAc (200 mL), the mixture was washed with water (80 mL). The organic phase was dried over Na$_2$SO$_4$ and concentrated under reduced pressure. The residue was purified by silica gel plate (EA:PE=1:10) to give 5-iodonaphthalen-1-ol as a brown solid (1.35 g, yield: 50%). ESI-MS (M+H)$^+$: 271.1.

$^1$H NMR (400 MHz, CDCl$_3$) δ: 8.23 (d, J=8.4 Hz, 1H), 8.09 (dd, J=7.6, 1.2 Hz, 1H), 7.69 (d, J=8.4 Hz, 1H), 7.40 (dd, J=8.4, 8.0 Hz, 1H), 7.17 (dd, J=8.4, 7.2 Hz, 1H), 6.87 (d, J=7.2 Hz, 1H).

Step 2: 1-(heptyloxy)-5-iodonaphthalene

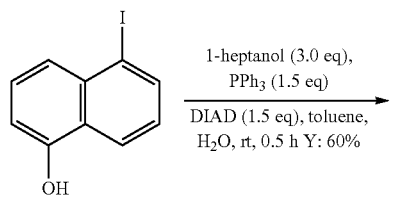
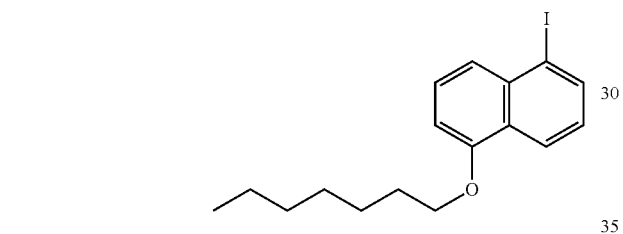

To a solution of 5-iodonaphthalen-1-ol (1.35 mg, 5 mmol, 1.0 eq) in toluene (10 mL) were added 1-heptanol (1.74 g, 15 mmol, 3.0 eq), PPh$_3$ (1.97 g, 7.5 mmol, 1.5 eq) and DIAD (1.52 g, 7.5 mmol, 1.5 eq) successively under N$_2$. The mixture was stirred at rt for 0.5 h and the solvent was removed under reduced pressure. The residue was purified by silica gel column (pure petroleum ether) to give 1-(heptyloxy)-5-iodonaphthalene as a slight yellow solid (1.1 g, yield: 60%). ESI-MS (M+H)$^+$: 369.1.

$^1$H NMR (400 MHz, CDCl$_3$) δ: 8.24 (d, J=8.4 Hz, 1H), 8.01 (dd, J=7.6, 1.2 Hz, 1H), 7.57 (d, J=8.8 Hz, 1H), 7.38 (t, J=8.0 Hz, 1H), 7.07 (dd, J=8.0, 7.2 Hz, 1H), 6.78 (d, J=7.6 Hz, 1H), 4.05 (t, J=6.4 Hz, 2H), 1.88-1.81 (m, 2H), 1.51-1.44 (m, 2H), 1.35-1.15 (m, 6H), 0.80 (t, J=7.2 Hz, 3H).

Step 3: 5-(heptyloxy)-1-naphthaldehyde

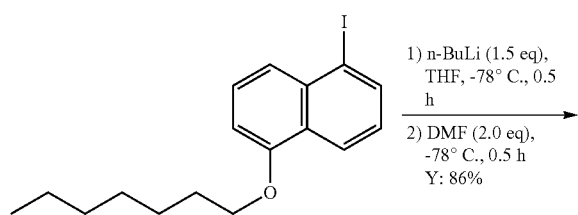
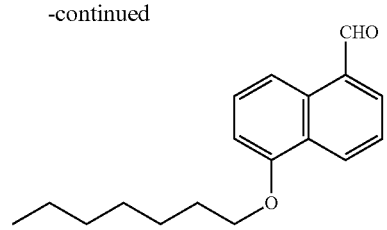

To a solution of 1-(heptyloxy)-5-iodonaphthalene (1.1 mg, 3.0 mmol, 1.0 eq) in dry THF (10 mL) was added n-BuLi (2.0 N in THF, 2.25 mL, 4.5 mmol, 1.3 eq) at −78° C. under N$_2$. The mixture was stirred at this temperature for 0.5 h and then DMF (5.0 mg, 6.9 mmol, 5.0 eq) was added. The resulting mixture was stirred at −78° C. for another 0.5 h. Water (20 mL) was added to quench the reaction and the mixture was extracted with EtOAc (100 mL×2). The combined organic phases were dried over Na$_2$SO$_4$, concentrated and the residue was purified by silica gel column (EA:PE=1:20) to give 5-(heptyloxy)-1-naphthaldehyde as a slight yellow solid (700 mg, yield: 86%). ESI-MS (M+H)$^+$: 311.1.

$^1$H NMR (400 MHz, CDCl$_3$) δ: 10.32 (s, 1H), 8.77 (d, J=8.4 Hz, 1H), 8.63 (d, J=8.4 Hz, 1H), 8.01 (dd, J=7.2, 1.2 Hz, 1H), 7.63-7.57 (m, 2H), 6.92 (d, J=8.0 Hz, 1H), 4.15 (t, J=6.4 Hz, 2H), 1.97-1.92 (m, 2H), 1.59-1.53 (m, 2H), 1.44-1.40 (m, 2H), 1.39-1.30 (m, 4H), 0.89 (t, J=6.8 Hz, 3H.

Step 4: ethyl 1-((5-(heptyloxy)naphthalen-1-yl) methyl)piperidine-4-carboxylate

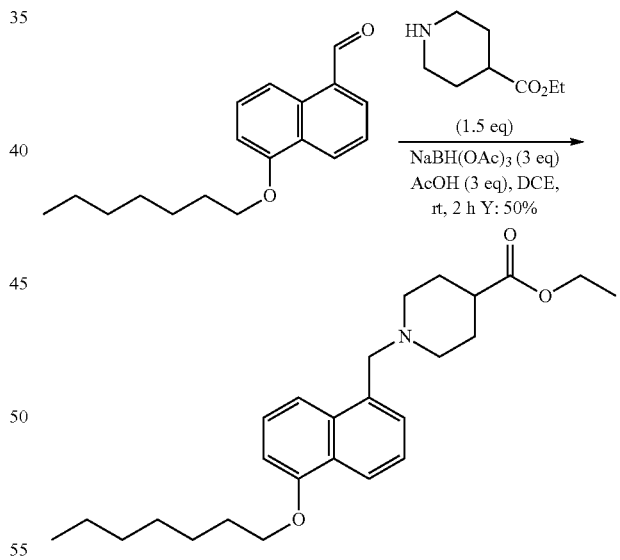

The preparation of ethyl 1-((5-(heptyloxy)naphthalen-1-yl)methyl)piperidine-4-carboxylate was the same as that of ethyl 1-((6-(((trans-4-(tert-butyl)cyclohexyl)oxy)naphthalen-1-yl)methyl)piperidine-4-carboxylate, 130 mg, as yellow oil, yield: 50%. ESI-MS (M+H)$^+$: 412.3.

$^1$H NMR (400 MHz, CDCl$_3$) δ: 8.27 (d, J=7.6 Hz, 1H), 7.82 (d, J=8.4 Hz, 1H), 7.44-7.38 (m, 3H), 6.82 (d, J=8.0 Hz, 1H), 4.07-4.01 (m, 4H), 3.78 (s, 2H), 2.86-2.83 (m, 2H), 2.23-2.19 (m, 1H), 2.04-2.00 (m, 2H), 1.87-1.68 (m, 6H), 1.52-1.45 (m, 2H), 1.35-1.24 (m, 6H), 1.16 (t, J=7.2 Hz, 3H), 0.83 (t, J=6.8 Hz, 3H).

Step 5: 1-((5-(heptyloxy)naphthalen-1-yl)methyl)piperidine-4-carboxylic acid

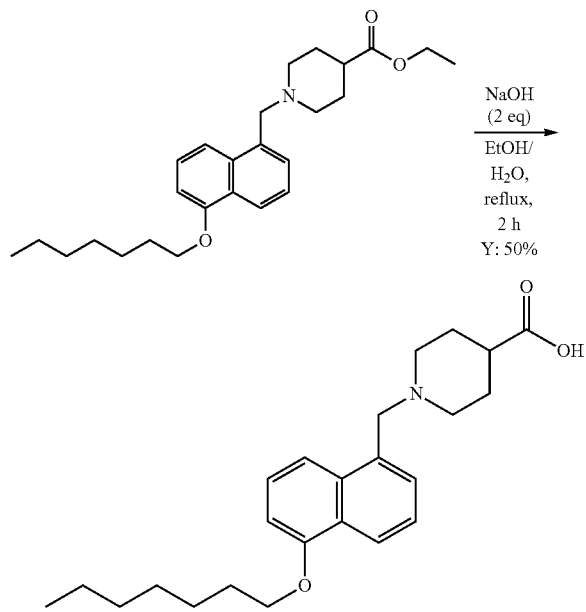

The preparation of 1-((5-(heptyloxy)naphthalen-1-yl)methyl)piperidine-4-carboxylic acid was the same as that of 1-((6-((trans-4-(tert-butyl)cyclohexyl)oxy)naphthalen-1-yl)methyl)piperidine-4-carboxylic acid, 13 mg, as white solid, yield: 50%. ESI-MS (M+H)$^+$: 384.2, HPLC: 100%-100%.

$^1$H NMR (400 MHz, CD$_3$OD) δ: 8.45 (d, J=8.4 Hz, 1H), 7.79 (s, 1H), 7.77 (d, J=2.0 Hz, 1H), 7.62-7.55 (m, 2H), 7.03 (d, J=8.0 Hz, 1H), 4.80 (s, 2H), 4.19 (t, J=6.4 Hz, 2H), 3.53-3.49 (m, 2H), 3.28-3.22 (m, 2H), 2.72-2.64 (m, 1H), 2.18-2.15 (m, 2H), 1.99-1.92 (m, 4H), 1.62-1.57 (m, 2H), 1.47-1.34 (m, 6H), 0.93 (t, J=6.8 Hz, 3H).

Example 30: 1-((5-((trans-4-(tert-butyl)cyclohexyl)oxy)naphthalen-1-yl)methyl)piperidine-4-carboxylic acid

Step 1: 1-((trans-4-(tert-butyl)cyclohexyl)oxy)-5-iodonaphthalene

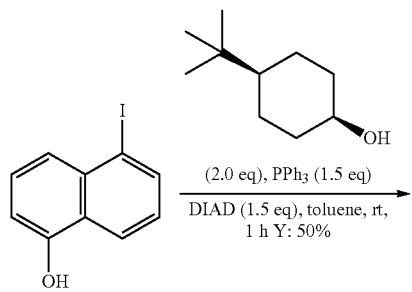

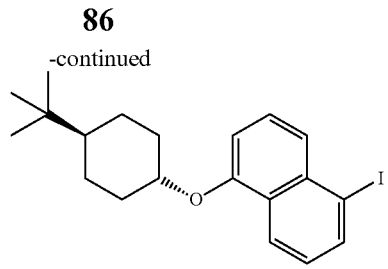

The preparation of 1-((trans-4-(tert-butyl)cyclohexyl)oxy)-5-iodonaphthalene was the same as that of 1-(heptyloxy)-5-iodonaphthalene. 1 g, as a slight solid, yield: 50%. ESI-MS (M+H)$^+$: 409.1

$^1$H NMR (400 MHz, CDCl$_3$) δ: 8.23 (d, J=8.4 Hz, 1H), 7.98 (dd, J=7.2, 0.8 Hz, 1H), 7.56 (d, J=8.4 Hz, 1H), 7.37 (t, J=8.0 Hz, 1H), 7.07-7.03 (m, 1H), 6.83 (d, J=8.4 Hz, 1H), 4.26-4.21 (m, 1H), 2.24-2.20 (m, 2H), 1.83-1.80 (m, 2H), 1.48-1.39 (m, 2H), 1.14-1.03 (m, 3H), 0.80 (s, 9H).

Step 2: 5-((trans-4-(tert-butyl)cyclohexyl)oxy)-1-naphthaldehyde

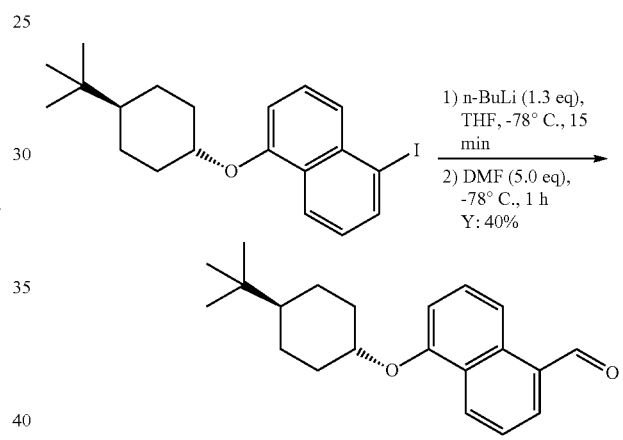

The preparation of 5-((trans-4-(tert-butyl)cyclohexyl)oxy)-1-naphthaldehyde was the same as that of 5-(heptyloxy)-1-naphthaldehyde. 400 mg, as a yellow solid, yield: 40%. ESI-MS (M+H)$^+$: 311.2.

$^1$H NMR (400 MHz, CDCl$_3$) δ: 10.40 (s, 1H), 8.75 (d, J=8.8 Hz, 1H), 8.64 (d, J=8.4 Hz, 1H), 7.99 (dd, J=6.8, 1.2 Hz, 1H), 7.60-7.55 (m, 2H), 6.97 (d, J=8.0 Hz, 1H), 4.38-4.32 (m, 1H), 2.34-2.30 (m, 2H), 1.93-1.89 (m, 2H), 1.58-1.49 (m, 2H), 1.25-0.92 (m, 3H), 0.89 (s, 9H).

Step 3: ethyl 1-((5-((trans-4-(tert-butyl)cyclohexyl)oxy)naphthalen-1-yl)methyl)piperidine-4-carboxylate

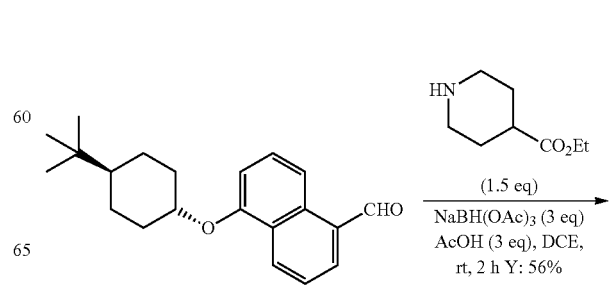

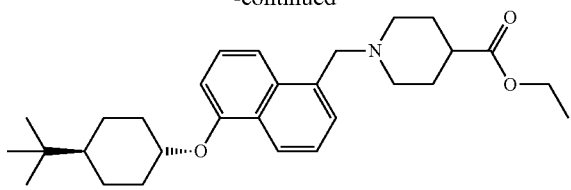

The preparation of ethyl 1-((5-((trans-4-(tert-butyl)cyclohexyl)oxy)naphthalen-1-yl)methyl)piperidine-4-carboxylate was the same as that of ethyl 1-((6-((trans-4-(tert-butyl)cyclohexyl)oxy)naphthalen-1-yl)methyl)piperidine-4-carboxylate. 200 mg, as a white solid, yield: 56%. ESI-MS (M+H)$^+$: 452.3.

$^1$H NMR (400 MHz, CDCl$_3$) δ: 8.24 (d, J=7.6 Hz, 1H), 7.81 (d, J=8.4 Hz, 1H), 7.43-7.36 (m, 3H), 6.87 (d, J=7.6 Hz, 1H), 4.33-4.28 (m, 1H), 4.11 (q, J=7.2 Hz, 2H), 3.84 (s, 2H), 2.93-2.89 (m, 2H), 2.33-2.30 (m, 3H), 2.12-2.07 (m, 2H), 1.91-1.74 (m, 6H), 1.27-1.13 (m, 5H), 1.25 (t, J=7.2 Hz, 3H), 0.86 (s, 9H).

Step 4: 1-((5-((trans-4-(tert-butyl)cyclohexyl)oxy)naphthalen-1-yl)methyl)piperidine-4-carboxylic acid

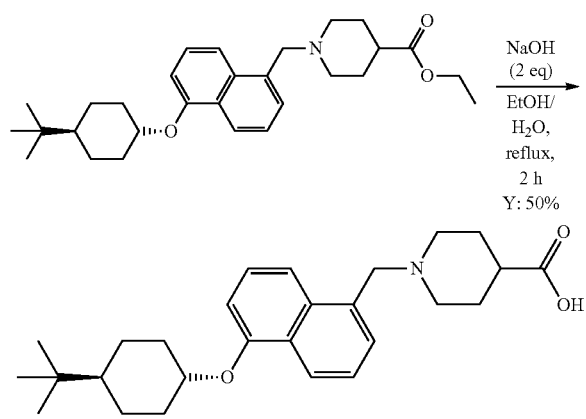

The preparation of 1-((5-((trans-4-(tert-butyl)cyclohexyl)oxy)naphthalen-1-yl)methyl)piperidine-4-carboxylic acid was the same as that of 1-((6-((trans-4-(tert-butyl)cyclohexyl)oxy)naphthalen-1-yl)methyl)piperidine-4-carboxylic acid. 70 mg, as a white solid, yield: 50%. ESI-MS (M+H)$^+$: 424.3. HPLC: 98.54%-100%.

$^1$H NMR (400 MHz, CD$_3$OD) δ: 8.37 (d, J=8.4 Hz, 1H), 7.72 (d, J=8.8 Hz, 1H), 7.65 (d, J=7.2 Hz, 1H), 7.52-7.44 (m, 2H), 6.98 (d, J=8.0 Hz, 1H), 4.52 (s, 2H), 4.39-4.16 (m, 1H), 3.35-3.31 (m, 2H), 2.94-2.85 (m, 2H), 2.37-2.30 (m, 3H), 2.02-1.89 (m, 6H), 1.55-1.49 (m, 2H), 1.27-1.13 (m, 3H), 0.91 (s, 9H).

Example 31: S1P Receptor Activity Assays

Compounds that are not specific for a particular S1P receptor can cause undesirable side effects. Accordingly, compounds are tested to identify those that are specific. Accordingly, the test compounds are tested in a calcium mobilization assay/S1P receptor activity assay. The procedure is essentially as described in Davis et al. (2005) *Journal of Biological Chemistry*, vol. 280, pp. 9833-9841, which is incorporated by reference in its entirety with the following modifications. Calcium mobilization assays are performed in recombinant CHEM cells expressing human S1P$_1$, S1P$_2$, S1P$_3$, S1P$_4$, or S1P$_5$ purchased from Millipore (Billerica, Mass.). To detect free intracellular calcium, S1P$_1$, S1P$_2$, S1P$_3$, S1P$_4$, or S1P$_5$ cells are loaded with FLIPR Calcium 4 dye from Molecular Devices (Sunnyvale, Calif.). Cells are imaged for calcium mobilization using a FLIPR$^{TETRA}$ equipped with a 96-well dispense head.

Agonist percentage activation determinations were obtained by assaying sample compounds and referencing the E$_{max}$ control for each receptor profiled. Antagonist percentage inhibition determinations were obtained by assaying sample compounds and referencing the control EC$_{80}$ wells for each receptor profiled.

Calcium Flux Assay: Agonist Assay Format

Sample compounds were plated in an eight-point, four-fold dilution series in duplicate with a top concentration of 10 μM. The concentrations described here reflect the final concentration of the compounds during the antagonist assay. During the agonist assay the compound concentrations were 1.25 fold higher to allow for the final desired concentration to be achieved with further dilution by EC$_{80}$ of reference agonists during the antagonist assay.

Reference agonists were handled as mentioned above serving as assay control. The reference agonists were handled as described above for E$_{max}$.

Assay was read for 180 seconds using the FLIPR$^{TETRA}$ (This assay run added sample compounds and reference agonist to respective wells). At the completion of the first "Single Addition" assay run, assay plate was removed from the FLIPR$^{TETRA}$ and placed at 25° C. for seven (7) minutes.

Calcium Flux Assay: Antagonist Assay Format

Using the EC$_{80}$ values determined during the agonist assay, stimulated all pre-incubated sample compound and reference antagonist (if applicable) wells with EC$_{80}$ of reference agonist. Read for 180 seconds using the FLIPR$^{TETRA}$ (This assay added reference agonist to respective wells—then fluorescence measurements were collected to calculate percentage inhibition values).

With regard to S1P4 antagonist activity, the compound of example 30 had an IC$_{50}$ value of no greater than 250 nM.

Example 32: ATX Activity Measurements

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in H$_2$O, stored at 4° C.

2×ATX assay buffer: 100 mM Tris, 280 mM NaCl, 10 mM KCl, 2 mM CaCl$_2$, 2 mM MgCl$_2$, pH 7.4.

Human ATX protein: expressed and purified in house. Stored at −80° C.

Substrate FS-3 (Echelon, L-2000): 100 μg in 77.74 μL H$_2$O (1 mM stock), stored at −20° C.

384-well flat bottom plates—Corning #3575.

Assay

Compound dilution—All compounds were provided at 10 mM in 100% DMSO. In the first well, 2 μL of 10 mM compound was added to 78 μL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and ddH$_2$O.

ATX protein was diluted with 1×ATX assay buffer to a concentration of 1.32 μg/mL (1.32×). 38 μL was added per well to the assay plate. The final concentration of ATX in the reaction as 1.0 μg/mL.

2 μL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 μM (5×). Then, 10 μL was added per well to the assay plate. The final concentration of FS-3 in the reaction was 2 μM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

With regard to ATX activity, compounds of the invention had the following IC$_{50}$ values:

| IC50 (μM) | Example No. |
|---|---|
| Less than 0.5 μM | 4, 24 |
| 0.5 μM to 5 μM | 1, 3, 5, 7, 9, 12, 13, 14, 15, 19, 20, 26, 27 |
| Greater than 5 μM | 2, 8, 10, 11, 17, 18, 21, 22, 23, 25, 28 |

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 μg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B5$^+$ OPCs were collected by shaking the flask overnight at 200 rpm and 37° C., resulting in a 95% pure population.

For the differentiation assay, 2 μM and 20 μM antagonist or the same concentrations of vehicle (DMSO) were applied to OPCs cultured in CNTF/T3 containing media. After a 3-day incubation, cells were lysed in 80 μL lysis buffer (50 mM HEPES [4-(2-hydroxyethyl)-1-piperazineethanesulfonic acid], pH 7.5, 150 mM NaCl, 1.5 mM MgCl$_2$, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 μg/mL)-coated cover slips and grown in neurobasal medium supplemented with B27 (Invitrogen) for one week. A2B5$^+$ OPCs are prepared as described above and then added into the cultured neocortical neurons. One day later, different concentrations of an S1P4 receptor antagonist or ATX inhibitor and control reagents are applied into the co-cultures. Fresh media containing the different concentrations of an S1P4 receptor antagonist or ATX inhibitor or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 μm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an S1P4 receptor antagonist or ATX inhibitor or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 μL of 1% Lysolecithin (LPC, Sigma# L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administered subcutaneously (s.c.) twice a day for additional two days following operation.

Three days following the primary surgery, treatments with an S1P4 receptor antagonist or ATX inhibitor (30 pmol), LPA (30 pmol) or control (0.1% DMSO in saline) are injected at the primary injection region in a volume of 1.5 μL with the same infusion speed as indicated above. Nine days following the primary surgery, the animals are anesthetized and perfused trans-cardially with heparin (10 iu/mL) in saline followed by 4% PFA in PBS. The spinal cords are removed and post fixed in PFA overnight. Then the cords are cut into 100 µM thickness longitudinally and then 1% loxuol fast blue is stained and histological evaluation for remyelination and repair is assessed under microscope.

For systemic treatment, the animals are administered once daily intraperitoneally with either an S1P4 receptor antagonist or ATX inhibitor (10 mg/kg) or control (15% HPCD (hydroxypropyl-β-cyclodextrin)) 2 days following the primary surgery. Nine days after the primary surgery, animals are sacrificed and the spinal cords were processed as indicated above.

In Vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVET™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of the invention can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 µl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or test compound, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4"×6"×10") having a wire grid (1 cm$^2$ spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, *Pain,* 1989, which is incorporated by reference in its entirety), adult male SD (250-275 g) rats are anesthetized with isoflurane inhalation (4.5% induction/ 2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or test compound post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat.#37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6" long×3" wide×4" tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Other embodiments are within the scope of the following claims.

What is claimed is:

1. A compound represented by formula (I):

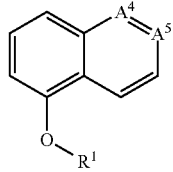

or a pharmaceutically acceptable salt thereof, wherein:

one of $A^4$ and $A^5$ is CH and the other is $CR^4$;

$R^1$ is a $C_{6-20}$alkyl, or a cyclohexyl which is optionally substituted with one $R^6$;

$R^4$ is a group represented by the following formula:

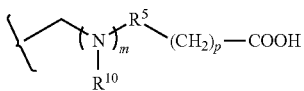

"⋮" represents the point of attachment;

$R^6$, for each occurrence, is independently selected from the group consisting of $C_{1-6}$alkyl, $C_{1-6}$haloalkyl, $C_{3-8}$cycloalkyl and phenyl;

$R^{10}$ is hydrogen or a $C_{1-6}$alkyl;

p is 0 or an integer from 1 to 6; and (i) m is 0; and $R^5$ is selected from the group consisting of:

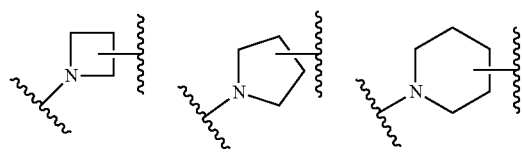

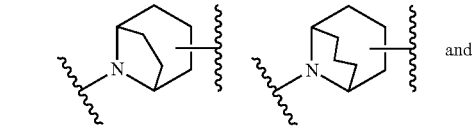

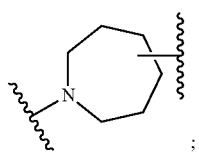

;

or (ii) m is 1; and $R^5$ is cyclobutylene, cyclopentylene or cyclohexylene.

2. The compound of claim 1, or a pharmaceutically acceptable salt thereof, wherein the compound is represented by structural formula (II):

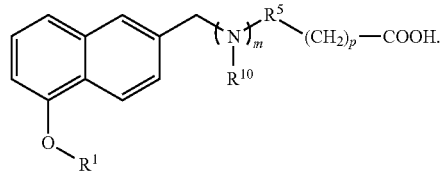

3. The compound of claim 1, or a pharmaceutically acceptable salt thereof, wherein the compound is represented by structural formula (III):

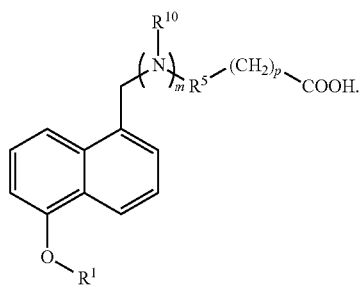

4. The compound of claim 1, or a pharmaceutically acceptable salt thereof, wherein:

m is 0; and $R^5$ is selected from the group consisting of:

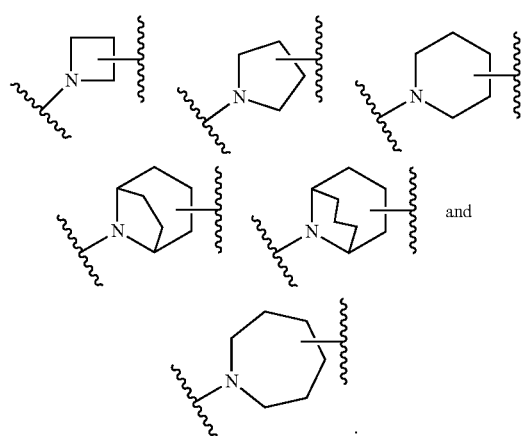

and

5. The compound of claim 1, or a pharmaceutically acceptable salt thereof, wherein:

m is 1; and $R^5$ is cyclobutylene, cyclopentylene or cyclohexylene.

6. A compound selected from the group consisting of:

8-((5-(((trans-4-(tert-butyl)cyclohexyl)oxy)naphthalen-2-yl)methyl)-8-azabicyclo[30.2.1]octane-3-carboxylic acid;

9-((5-(((trans-4-(tert-butyl)cyclohexyl)oxy)naphthalen-2-yl)methyl)-9-azabicyclo[30.3.1]nonane-3-carboxylic acid;

3-(((5-((trans-4-(tert-butyl)cyclohexyl)oxy)naphthalen-2-yl)methyl)amino)-2,2-dimethylcyclobutanecarboxylic acid;

1-((5-((trans-4-(tert-butyl)cyclohexyl)oxy)naphthalen-2-yl)methyl)azetidine-3-carboxylic acid;
2-((5-((trans-4-(tert-butyl)cyclohexyl)oxy)naphthalen-2-yl)methyl)octahydrocyclopenta[c]pyrrole-5-carboxylic acid;
1-((5-((trans-4-(tert-butyl)cyclohexyl)oxy)naphthalen-2-yl)methyl)pyrrolidine-3-carboxylic acid;
3-(((5-((trans-4-(tert-butyl)cyclohexyl)oxy)naphthalen-2-yl)methyl)amino)cyclobutanecarboxylic acid;
1-((5-((trans-4-(tert-butyl)cyclohexyl)oxy)naphthalen-2-yl)methyl)azepane-4-carboxylic acid;
1-((5-((trans-4-(trifluoromethyl)cyclohexyl)oxy)naphthalen-2-yl)methyl)piperidine-4-carboxylic acid;
1-((5-((cis-4-(trifluoromethyl)cyclohexyl)oxy)naphthalen-2-yl)methyl)piperidine-4-carboxylic acid;
1-((5-((cis-4-isopropylcyclohexyl)oxy)naphthalen-2-yl)methyl)piperidine-4-carboxylic acid;
1-((5-((cis-4-ethylcyclohexyl)oxy)naphthalen-2-yl)methyl)piperidine-4-carboxylic acid;
1-((5-((trans-4-isopropylcyclohexyl)oxy)naphthalen-2-yl)methyl)piperidine-4-carboxylic acid;
1-((5-((trans-4-ethylcyclohexyl)oxy)naphthalen-2-yl)methyl)piperidine-4-carboxylic acid;
1-((5-((trans-4-methylcyclohexyl)oxy)naphthalen-2-yl)methyl)piperidine-4-carboxylic acid;
1-((5-((4,4-dimethylcyclohexyl)oxy)naphthalen-2-yl)methyl)piperidine-4-carboxylic acid;
1-((5-((trans-4-methylcyclohexyl)oxy)naphthalen-2-yl)methyl)azetidine-3-carboxylic acid;
1-((5-((trans-4-phenylcyclohexyl)oxy)naphthalen-2-yl)methyl)azetidine-3-carboxylic acid;
1-((5-((trans-4-ethylcyclohexyl)oxy)naphthalen-2-yl)methyl)azetidine-3-carboxylic acid;
1-((5-((trans-4-(trifluoromethyl)cyclohexyl)oxy)naphthalen-2-yl)methyl)azetidine-3-carboxylic acid;
1-((5-((trans-4-isopropylcyclohexyl)oxy)naphthalen-2-yl)methyl)azetidine-3-carboxylic acid;
1-((5-((trans-4-butylcyclohexyl)oxy)naphthalen-2-yl)methyl)azetidine-3-carboxylic acid;
1-((5-((trans-4-cyclopentylcyclohexyl)oxy)naphthalen-2-yl)methyl)azetidine-3-carboxylic acid;
1-((5-((trans-4-(tert-butyl)cyclohexyl)oxy)naphthalen-2-yl)methyl)piperidine-4-carboxylic acid;
1-((5-(heptyloxy)naphthalen-2-yl)methyl)piperidine-4-carboxylic acid;
9-((5-((cis-4-methylcyclohexyl)oxy)naphthalen-2-yl)methyl)-9-azabicyclo[3.3.1]nonane-3-carboxylic acid;
8-((5-((cis-4-methylcyclohexyl)oxy)naphthalen-2-yl)methyl)-8-azabicyclo[3.2.1]octane-3-carboxylic acid;
1-((5-((cis-4-methylcyclohexyl)oxy)naphthalen-2-yl)methyl)piperidine-4-carboxylic acid;
1-((5-(heptyloxy)naphthalen-1-yl)methyl)piperidine-4-carboxylic acid; and
1-((5-((trans-4-(tert-butyl)cyclohexyl)oxy)naphthalen-1-yl)methyl)piperidine-4-carboxylic acid;
or a pharmaceutically acceptable salt thereof.

7. A pharmaceutical composition comprising a pharmaceutically acceptable carrier or excipient and a compound according to claim 1, or a pharmaceutically acceptable salt thereof.

8. A method of treating or reducing symptoms of a condition selected from the group consisting of multiple sclerosis, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a vascular disease, a pain condition, an acute viral disease, an inflammatory bowel condition, insulin-dependent diabetes, non-insulin dependent diabetes, a fibrosis of the lung, and a malignancy of the lung in a mammal comprising administering to said mammal an effective amount of a compound according to claim 1, or a pharmaceutically acceptable salt thereof.

9. The method of claim 8, wherein the condition is multiple sclerosis.

10. The method of claim 8, wherein the condition is rheumatoid arthritis.

11. The method of claim 8, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

12. A method of treating or reducing chronic pain in a mammal comprising administering to said mammal an effective amount of a compound according to claim 1, or a pharmaceutically acceptable salt thereof.

13. The method of claim 12, wherein the chronic pain is inflammatory pain.

14. The method of claim 13, wherein the chronic pain is neuropathic pain.

* * * * *